US012736481B2

(12) United States Patent
Kurs et al.

(10) Patent No.: US 12,736,481 B2
(45) Date of Patent: Sep. 15, 2026

(54) DETECTING AND IMAGING USING DIELECTRIC TOMOGRAPHY

(71) Applicant: OMNIZARE IMAGING INC., Waltham, MA (US)

(72) Inventors: Andre Botelho Kurs, Ayer, MA (US); Eric Roger Giler, Boston, MA (US); Katherine Lavin Hall, Arlington, MA (US)

(73) Assignee: OmniZare Imaging Inc., Waltham, MA (US)

( * ) Notice: Subject to any disclaimer, the term of this patent is extended or adjusted under 35 U.S.C. 154(b) by 309 days.

(21) Appl. No.: 18/505,488

(22) Filed: Nov. 9, 2023

(65) Prior Publication Data

US 2024/0302293 A1 Sep. 12, 2024

Related U.S. Application Data

(63) Continuation-in-part of application No. 18/180,969, filed on Mar. 9, 2023.

(51) Int. Cl.
*G01N 22/00* (2006.01)
*A61B 5/00* (2006.01)
(Continued)

(52) U.S. Cl.
CPC .......... *G01N 22/00* (2013.01); *A61B 5/0033* (2013.01); *A61B 5/0507* (2013.01);
(Continued)

(58) Field of Classification Search
CPC .... G01N 22/00; G01N 27/221; A61B 5/0507; A61B 5/0033; A61B 5/6888; A61B 2562/02; A61B 2576/00; G01S 13/89
(Continued)

(56) References Cited

U.S. PATENT DOCUMENTS 5,363,050 A 11/1994 Guo et al.
6,448,788 B1 9/2002 Meaney et al.
(Continued)

FOREIGN PATENT DOCUMENTS

KR 20090011160 A 2/2009
KR 20170007674 A 1/2017
(Continued)

OTHER PUBLICATIONS

Origlia, C. et al., "Review of Microwave Near-Field Sensing and Imaging Devices in Medical Applications," Sensors 2024, 24, No. 14:4515, https://doi.org/10.3390/s24144515.
(Continued)

*Primary Examiner* — Raul J Rios Russo
(74) *Attorney, Agent, or Firm* — Nutter McClennen & Fish LLP

(57) ABSTRACT

Techniques are provided for sensing, detecting, characterizing, and imaging dielectric objects using microwave signals. An example of a method for obtaining an image with a dielectric tomography system includes positioning an object in at least a portion of an electromagnetic field of a characterized sensor including at least one transmit antenna configured to transmit a radio frequency signal within 10 MHz and 300 GHz, positioning one or more receive antennas configured to receive one or more radio frequency signals scattered by the object, determining permittivity information associated with the object based at least in part on phase and magnitude measurements of the one or more radio frequency signals received by the one or more receive antennas, and computing one or more images based on the permittivity information and calibration information associated with the characterized sensor.

29 Claims, 43 Drawing Sheets

(51) Int. Cl.
*A61B 5/0507* (2021.01)
*G01N 27/22* (2006.01)

(52) U.S. Cl.
CPC ......... *A61B 5/6888* (2013.01); *G01N 27/221* (2013.01); *A61B 2562/02* (2013.01); *A61B 2576/00* (2013.01)

(58) Field of Classification Search
USPC .......................................................... 324/644
See application file for complete search history.

(56) References Cited

U.S. PATENT DOCUMENTS

| | | | | |
|---|---|---|---|---|
| 7,164,105 | B2 | 1/2007 | Godshalk et al. | |
| 7,825,667 | B2 | 11/2010 | Fang et al. | |
| 12,002,584 | B2 | 6/2024 | Alon et al. | |
| 12,567,503 | B2 | 3/2026 | Alon et al. | |
| 2003/0088180 | A1 | 5/2003 | Van Veen et al. | |
| 2005/0203387 | A1 | 9/2005 | Godshalk et al. | |
| 2008/0157765 | A1* | 7/2008 | Fontius | G01R 33/3415 324/309 |
| 2008/0288024 | A1* | 11/2008 | Abrahamson | H01Q 1/22 607/60 |
| 2009/0027288 | A1 | 1/2009 | Lee et al. | |
| 2012/0062408 | A1 | 3/2012 | Bausov et al. | |
| 2014/0155740 | A1 | 6/2014 | Semenov | |
| 2014/0218230 | A1 | 8/2014 | Ostadrahimi et al. | |
| 2015/0355110 | A1* | 12/2015 | Sappok | G01N 1/44 324/639 |
| 2016/0266051 | A1 | 9/2016 | Lee et al. | |
| 2019/0021626 | A1 | 1/2019 | Cano Garcia et al. | |
| 2020/0187793 | A1* | 6/2020 | Leabman | A61B 5/6898 |
| 2022/0192511 | A1* | 6/2022 | Leabman | H01Q 1/273 |
| 2024/0298914 | A1 | 9/2024 | Kurs et al. | |

FOREIGN PATENT DOCUMENTS

| | | | |
|---|---|---|---|
| WO | 2013/005134 | A2 | 1/2013 |
| WO | 2014/015238 | A1 | 1/2014 |
| WO | 2018/098387 | A1 | 5/2018 |
| WO | 2020/076371 | A1 | 4/2020 |
| WO | 2022/029685 | A1 | 2/2022 |

OTHER PUBLICATIONS

European Patent Office, International Search Report and Written Opinion of the International Searching Authority, Application No. PCT/US2024/017827, dated Jun. 21, 2024, 18 pages.
A. Mase et al., "Development and application of radar reflectometer using micro to infrared waves," Advances in Physics: X, vol. 3, No. 1, Jan. 1, 2018, p. 1472529, XP093172381, ISSN: 2375-6149; DOI: 10.1080/23746149.2018.1472529.
I. Hieda et al., "Electric Field Measurement of the Living Human Body for Biomedical Applications: Phase Measurement of the Electric Field Intensity," International Journal of Antennas and Propagation, vol. 2013, Jan. 1, 2013, pp. 1-6; XP093171416, ISSN: 1687-5869, DOI: 10.1155/2013/305362.
I. Hieda et al., "Electric Field Measurement for Biomedical Application—Characteristics of Raw Measurement Data," 2012 International Conference on Biomedical Engineering and Biotechnology, May 1, 2012, pp. 789-792, XP093171429, DOI: 10.1109/ICBEB.2012.191.
F. Thiel et al., "Combining magnetic resonance imaging and ultrawideband radar: A new concept for multimodal biomedical imaging," Review of Scientific Instruments, American Institute of Physics, vol. 80, No. 1, Jan. 9, 2009, pp. 14302-1-14302-10, XP012127887, ISSN: 0034-6748, DOI: 10.1063/1.3065095.
J. Bourqui et al., "System for Bulk Dielectric Permittivity Estimation of Breast Tissues at Microwave Frequencies," IEEE Transactions on Microwave Theory and Techniques, IEEE, USA, Vo. 64, No. 9, Sep. 1, 2016, pp. 3001-3009, XP011621501, ISSN: 0018-9480, DOI: 10.1109/TMTT.2016.2586486.
W. Shao et al., "Advances in Microwave Near-Field Imaging: Prototypes, Systems, and Applications," IEEE Microw Mag. May 2020, vol. 21, Nov. 5, pp. 94-119; doi: 10.1109/mmm.2020.2971375.
M. Aldhaeebi et al., "Review of Microwaves Techniques for Breast Cancer Detection," Sensors, 2020, vol. 20, No. 8, 2390, https://doi.org/10.3390/s20082390.
R. Benny et al., "An Overview of Microwave Imaging for Breast Tumor Detection," Progress in Electromagnetics Research B, vol. 87, 2020, pp. 61-91.
I. Saied et al., "Dielectric Measurements of Brain Tissues with Alzheimer's Disease Pathology in the Microwave Region," 2019 IEEE International Symposium on Medical Measurements and Applications, Istanbul, Turkey, 2019, pp. 1-6, doi: 10.1109/MeMeA.2019.8802179.
R. Ullah et al., "Detecting Pathological Changes in the Brain Due to Alzheimer Disease Using Numerical Microwave Signal Analysis," 2020 IEEE International RF and Microwave Conference, Kuala Lumpur, Malaysia, 2020, pp. 1-4, doi: 10.1109/RFM50841.2020.9344758.
I. Saied et al., "Noninvasive Wearable RF Device Towards Monitoring Brain Atrophy and Lateral Ventricle Enlargement," IEEE Journal of Electromagnetics, RF, and Microwaves in Medicine and Biology, vol. 4, No. 1, Mar. 2020, pp. 61-68.
L.Guo et al., "Stroke Diagnosis Using Microwave Techniques: Review of Systems and Algorithms," IEEE Journal Electromagnetics, RF and Microwaves in Medicine and Biology, Jun. 2023, vol. 7, No. 2, pp. 122-135, doi: 10.1109/JERM.2022.3227724.
International Preliminary Report on Patentability for International Patent Application No. PCT/US024/017827, issued May 12, 2025, 29 pages.
International Search Report for International Patent Application No. PCT/US024/017827, issued Jun. 21, 2024, 6 pages.

* cited by examiner

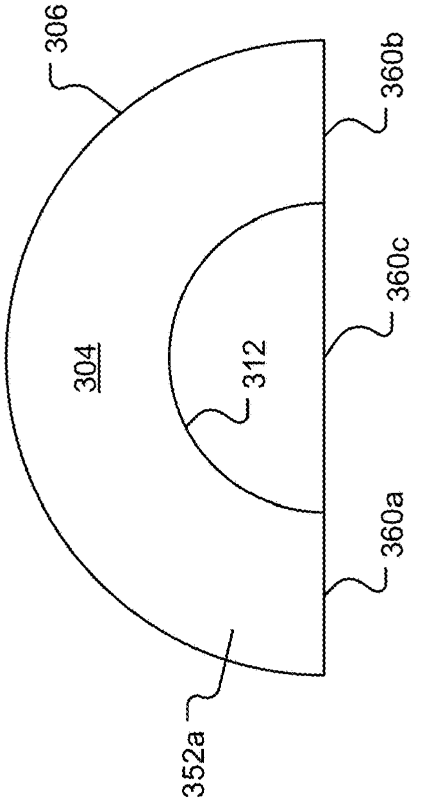
FIG. 5E
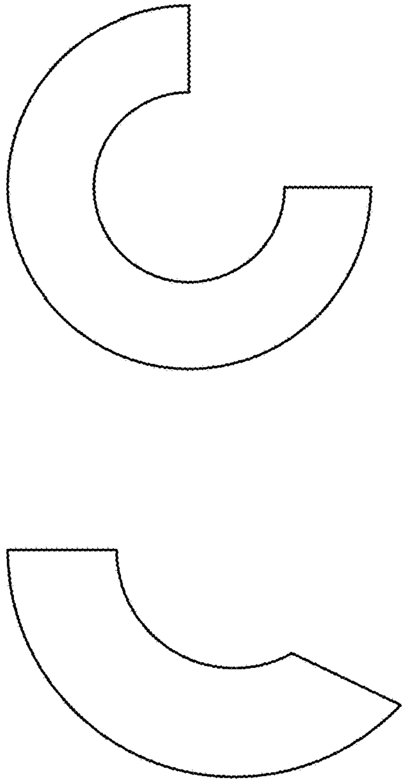
FIG. 5F
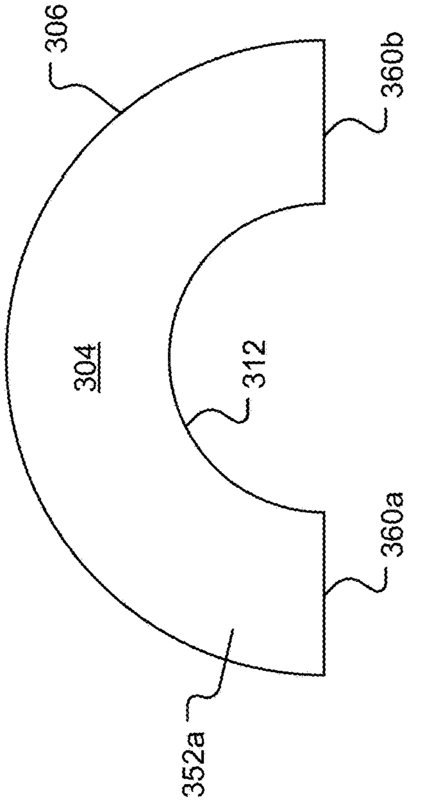
FIG. 5D
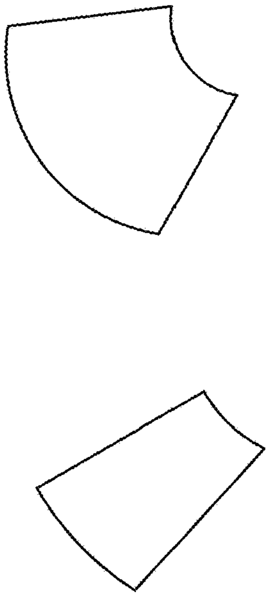

DETECTING AND IMAGING USING DIELECTRIC TOMOGRAPHY

CROSS-REFERENCE TO RELATED APPLICATION

This application is a continuation-in-part of U.S. patent application Ser. No. 18/180,969, filed Mar. 9, 2023, entitled "DETECTING AND IMAGING USING DIELECTRIC TOMOGRAPHY," which is assigned to the assignee hereof, and the entire contents of which are hereby incorporated herein by reference for all purposes.

BACKGROUND

Dielectric tomography (DT) may be applied to a wide range of imaging and detection applications. In one example, it is an emerging medical imaging modality which may provide advantages over existing medical imaging technologies. Dielectric tomography uses electromagnetic fields in the microwave radiofrequency range (typically 10 MHz to 300 GHz) to probe and image body tissue, although many other applications exist and are within the scope of this disclosure. In contrast to X-rays used in computerized tomography (CT) scans, microwave electromagnetic fields are non-ionizing and do not require lead shielding for safety. The power levels of non-ionizing electromagnetic fields that DT exposes the human, patient, and or body tissue or tissues to are lower than those emitted by mobile phones operating at similar frequencies.

Dielectric tomography may allow for three-dimensional millimeter-scale or sub-millimeter scale resolution of the ultra-wideband dielectric properties of biological tissue. Characterizing these physical properties using dielectric tomography may complement measurements and/or characterizations performed by existing medical imaging techniques. Research shows that these dielectric properties correlate with several clinically relevant conditions and could enable applications such as accurately differentiating between healthy and cancerous tissues for cancer screening, detecting, diagnosing, and monitoring strokes and concussions, monitoring internal bleeding and deep contusions, and measuring bone density to detect degenerative diseases and infections, to name a few applications.

SUMMARY

An example of a method for obtaining an image with a dielectric tomography system according to the disclosure includes positioning an object under test in at least a portion of an electromagnetic field of a characterized sensor including at least one transmit antenna configured to transmit a radio frequency signal within a frequency range from approximately 10 MHz to 300 GHz, positioning one or more receive antennas configured to receive one or more radio frequency signals transmitted and/or scattered by at least the object under test, determining permittivity information associated with the object under test based at least in part on phase and magnitude measurements of the one or more radio frequency signals received by the one or more receive antennas, and computing one or more images based on the permittivity information and calibration information associated with the characterized sensor.

Implementations of such a method may include one or more of the following features. The calibration and/or characterization information for the characterized sensor may be based at least in part on phase and magnitude measurements obtained when a known scattering device or object is disposed within the electromagnetic field emitted by the at least one transmit antenna of the sensor. An electromagnetic scattering device may be disposed in the electromagnetic field generated by the transmit antenna, such that the one or more receive antennas are configured to receive one or more radio frequency signals transmitted and/or scattered at least by the electromagnetic scattering device. The electromagnetic scattering device may be moved relative to at least one antenna while the one or more receive antennas are receiving the one or more radio frequency signals scattered at least by the electromagnetic scattering device. In embodiments, the electromagnetic scattering device may be moved before or after or while any of the transmit or receive antennas are transmitting or receiving electromagnetic fields. The method may include transmitting at least a first signal at a first radio frequency and transmitting at least a second signal at a second radio frequency that is different from the first radio frequency, and determining the permittivity information associated with an object under test based at least in part on phase and magnitude measurements of one or more radio frequency signals at the first radio frequency received by the one or more receive antennas, one or more radio frequency signals at the second radio frequency received by the one or more receive antennas, and the calibration and/or characterization information associated with the characterized sensor. A coupling medium may be disposed in the region proximate to the transmit antenna and the one or more receive antennas, and at least one of a temperature, pressure, and volume of the coupling medium may be controlled. A pliable membrane may be disposed between the coupling medium and the object under test. A conducting surface may be disposed at least partially along at least one side and/or one portion of the volume of the coupling medium. A location of the object under test may be changed relative to the locations of the at least one transmit antenna and the one or more receive antennas. Changing the location of the object under test may include moving the object under test relative to stationary locations of the at least one transmit antenna and the one or more receive antennas. Changing the location of the object under test may include moving the transmit antenna or the one or more receive antennas relative to a stationary object under test. At least one of the one or more receive antennas may be configured to transmit a radio frequency signal within 10 MHz and 300 GHz, and the transmit antenna may be configured to receive one or more radio signals scattered by the electromagnetic scattering device and/or the object under test.

An example of a method for calibrating and/or characterizing a dielectric tomography system according to the disclosure includes positioning a scattering device at a first location within at least a portion of an electromagnetic field generated by a transmit antenna and proximate to one or more receive antennas configured to receive one or more radio frequency signals transmitted and/or scattered by the scattering device, measuring the phase and magnitude of the one or more radio frequency signals received by the one or more receive antennas, and determining electromagnetic fields in a region proximate to the transmit and receive antennas, based at least in part on the first location of the scattering device and the phase and magnitude measurements. The electromagnetic fields of the current invention may be electromagnetic near-fields, electromagnetic far-fields, or both. In this disclosure, we may use the singular and plural forms of the terms field and/or electromagnetic field. One of ordinary skill in the art will understand that the singular or plural form of these terms does not constitute a limitation.

Implementations of such a method may include one or more of the following features. The electromagnetic scattering device may be moved, including by translation and/or rotation, to a second location within the electromagnetic field of the transmit antenna. Moving the electromagnetic scattering device may include moving along a linear path between the first location and the second location. Moving the scattering device may include moving along a circular path including the first location and the second location. The electromagnetic scattering device may be an extended object such as a cylinder or plane with electromagnetic features on its surface (such as a metallic cylinder with a hole of any shape and dimension, multiple holes of similar or different shapes and dimensions, and/or patterns of shapes of any size and dimension etched or cut into its surface). Such an extended object may be moved relative to the transmit and receive antennas through a combination of rotations and/or translations.

An example of a dielectric tomography system according to the disclosure includes a memory, at least one transmit antenna configured to transmit a radio frequency signal within 10 MHz and 300 GHz, one or more receive antennas configured to receive one or more radio frequency signals scattered by at least an object under test disposed in an electromagnetic field generated by the at least one transmit antenna, a measurement apparatus that measure magnitudes and phases of at least some of the transmitted and reflected fields, such as a vector network analyzer or a direct RF-instrument or a customized analyzer, communicatively coupled to the at least one transmit antenna and the one or more receive antennas, at least one processor communicatively coupled to the memory and a measurement apparatus that measures magnitude and phase of the incident and reflected fields, such as a vector network analyzer or a direct-RF instrument or a customized analyzer, and configured to determine permittivity information associated with the object under test based at least in part on phase and magnitude measurements of the one or more radio frequency signals received by the one or more receive antennas, and compute one or more images based on the permittivity information and calibration and/or characterization information associated with the dielectric tomography system.

Items and/or techniques described herein may provide one or more of the following capabilities, as well as other capabilities not mentioned. A dielectric tomography system may include one or more transmit antennas configured to transmit at least one radio frequency signal from what may be referred to as a sensor domain into an observation area, sometimes referred to as an object domain, and one or more receive antennas configured to receive the radio frequency signals transmitted through and or scattered from the observation or object domain back into the sensor domain. A scattering device with known electrical properties may be disposed in the observation area and/or at the interface between the sensor domain and the object domain to obtain calibration and/or characterization data for the dielectric tomography system. An object under test may be disposed in the object domain and/or at the interface between the sensor domain and the object domain and permittivity information associated with the object under test may be obtained based at least in part on the phase and magnitude of the received radio frequency signals. Image reconstruction algorithms may utilize the permittivity information and the calibration and/or characterization data to generate images of the object under test. The calibration and/or characterization data may reduce the processing required to obtain the images. The processing time and/or processing power required to obtain tomographic images may be reduced. Other capabilities may be provided and not every implementation according to the disclosure must provide any, let alone all, of the capabilities discussed. Further, it may be possible for an effect noted above to be achieved by means other than that noted, and a noted item/technique may not necessarily yield the noted effect.

BRIEF DESCRIPTION OF THE DRAWINGS

FIGS. 5A-5F are respective side, top, and perspective views of an example annular sensor in a dielectric tomography system.

DETAILED DESCRIPTION

Figure 1:
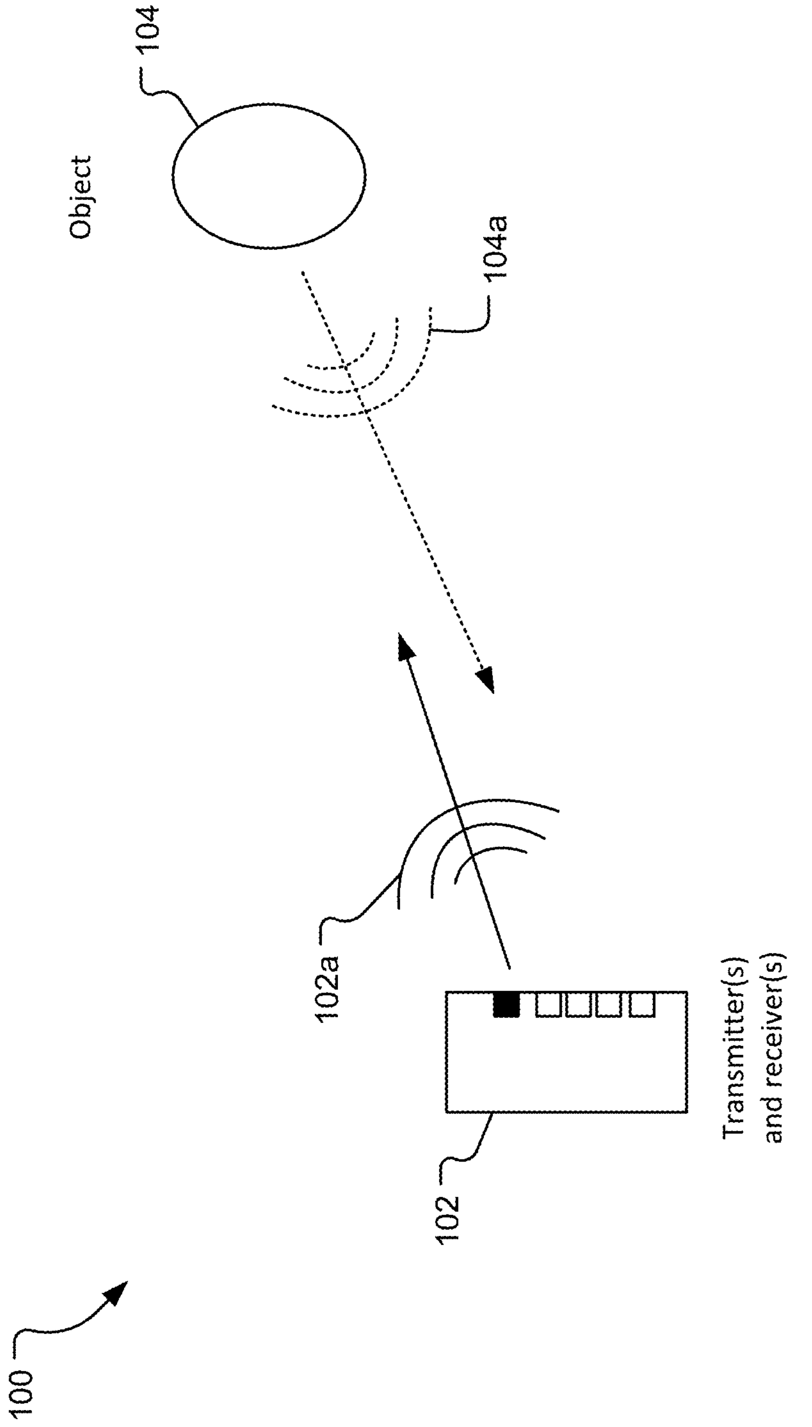
FIG. 1 is a diagram of an example radio frequency (RF) sensing use case.

Techniques are discussed herein for sensing, detecting, characterizing, and imaging dielectric objects using microwave signals for applications in object detection, object identification, imaging, medical imaging, non-invasive characterization, and non-destructive testing. In particular, the disclosure relates to dielectric tomography (DT), microwave imaging (MWI), microwave tomography (MWT), microwave holography, and using microwave imaging techniques to detect certain medical conditions and objects related to the human body such as tissues, tumors, clots, swelling, bleeding, cysts, fractures, lesions, plaques, organ abnormalities, and the like. Techniques are also discussed for imaging biological tissues to discern both structural and functional properties of the tissue, and for using DT as a stand-alone system and/or as a complement to other imaging modalities such as x-ray imaging, magnetic resonance imaging (MRI), ultrasonography, computed tomography (CT), optical coherence tomography (OCT), positron emission tomography (PET), and the like. In addition, DT may be used in therapeutic applications and may provide information on the efficacy of one-time, periodic, continuous, and/or on-going therapeutic treatments. DT may be administered by human beings or may be computer controlled, robotically controlled, and/or may be controlled by machine learning, artificial intelligence, or neural network type algorithms. Information determined by DT may inform patient treatment plans, drug dispensing plans, and the like and may be used in treatment algorithms and procedures. The techniques discussed are not restricted to certain medical conditions or objects related to the human body, and one of ordinary skill in the art will understand that the methods and apparatuses described herein may be used to sense, detect and image the dielectric properties of materials and objects generally. One of ordinary skill in the art will also understand that the magnetic or permeability properties of materials and objects generally may be sensed, detected, and imaged using the methods and apparatuses disclosed herein. In certain medical applications, magnetic imaging may be enhanced by the use of ingestible and/or injectable magnetic materials, dyes, tracers and the like.

The DT hardware, software, methods, and system designs for sensing systems described herein may comprise sensors that transmit and receive microwave signals. In an example, some microwave signals may be processed and analyzed for use in sensing, detecting, identifying, and/or imaging objects with certain electromagnetic properties. The various hardware architectures and characterization techniques described herein may enable improved sensing times with accuracy sufficient for quantitative sensor, detection, identification, and imaging applications. The hardware architecture utilizes microwave radiofrequency technology and numerical modeling techniques for reconstruction of three-dimensional images from radiofrequency measurements. An example dielectric tomography system may be used to sense, detect, identify, and/or characterize an object(s) in the body such as shrapnel, glass, clots, tumors, lesions, swelling, tracers, and the like, but a similar or the same embodiments may be used to sense, detect, identify and/or characterize a range of other objects under test (OUT) such as objects within clothing and/or enclosures, objects behind walls or obstructions, magnetic objects, objects comprising magnetic materials, objects of unknown or partially known composition, and the like. In an example, a dielectric tomography system may be used to distinguish regions of different electromagnetic permittivity and/or conductivity and/or permeability within an OUT.

In an example, a dielectric tomography system may include one or more sensors comprising one or more transmitting and receiving antenna systems configured to transmit or receive electromagnetic energy into and/or from a coupling medium. An OUT may be disposed in or proximate to the coupling medium such that the electromagnetic energy may couple to and propagate towards, through and/or be reflected and/or scattered by the OUT. The electromagnetic energy may be at least partially transmitted, reflected, diffracted, refracted, and/or scattered by the OUT. One or more processors may be configured to analyze the electromagnetic signals that are at least partially transmitted, reflected, diffracted, refracted and/or scattered by the OUT to sense, detect, identify, and/or characterize the OUT. One of ordinary skill in the art will understand that scattered signals may comprise at least partially transmitted, and/or reflected, and/or refracted, and/or diffracted signals. Scattered signals may travel through a scattering object and/or they may be redirected from their incident path. In this disclosure we may refer to electromagnetic signals that are at least partially transmitted and/or at least partially redirected from their incident paths as scattered signals, and/or refracted signals, and/or diffracted signals, and/or reflected signals. These terms may be used individually and/or in combination and are not intended to limit the scope of the invention in any way. The processors may be configured to construct an image based on the electromagnetic signals. Various sensor configurations may be used based on the nature and shape of the OUT. For example, an OUT may be inserted into an annulus sensor configuration, a sensor configuration may be movable and configured to traverse over a portion of the OUT, and/or a linear sensor configuration may be disposed on a portion of the OUT. Other sensor configurations may also be used. A fluid, gel, and/or emulsion coupling medium may be used to improve the propagation of the electromagnetic signals into the OUT and fluid pressure control and filtration systems may be used to control the properties of the coupling medium. Flexible surfaces may be used to increase the effectiveness of the coupling medium with the OUT. Laminated materials may be utilized to house the microwave sensors to reduce the impact of external signals. Scattering devices may be used to calibrate different sensor configurations. These techniques are examples only, and not exhaustive.

In an example, sensor and/or imaging data may be collected on time scales that are short enough to resolve the time behavior of certain medical processes. For example, images of and/or data signals related to a heart may be collected often enough to observe the expansion and contraction of heart chambers, vessels, and valves. Images of and/or data signals related to a lung may be collected often enough to resolve the expansion and contraction of the lung. Images of and/or data related to an artery and/or vein may be collected often enough to observe the efficacy of a clotting agent. Images of and/or data to the brain may be collected often enough to monitor the progression of a disease such as Alzheimer's and/or traumatic brain injuries such as concussions and/or chronic traumatic encephalopathy (CTE). Images may be collected often enough to characterize drug and/or therapy induced changes, such as when a brain is exposed to photobiomodulation (PBM) treatments. Images and/or data signals may be collected at least once a microsecond, once a millisecond, once a second, once a minute, once an hour, once a day, once a week, once a month, once a year and the like.

The sensors described herein may measure the naturally predominant dielectric properties of biological tissue at microwave frequencies and may also measure magnetic or permeability properties of tissues. In an example, a test subject or patient may be injected with a ferromagnetic contrast agent and/or may ingest ferromagnetic liquids, capsules, and/or particles, and the sensor may measure the resulting 3D magnetic properties, in addition to the naturally occurring dielectric properties. The injectable or ingestible contrast agents may have dielectric and magnetic properties that are substantially different than those naturally occurring in biological tissue or in the OUT.

One or more sensors may be configured to capture a single 3D image or series of 2D images at a substantially single point in time. The sensors may capture a time-series of such images at regular or semi-regular points in time. The interval between images may be sufficiently short to track phenomena such as metabolic processes and therapeutic responses and the like. The interval may be sufficiently long to help in monitoring and diagnosing conditions such as bone health, wound healing, tumor growth, disease progression, and the like. Supporting computer systems and software may be configured to perform additional processing of the time-series images to aid in monitoring and diagnostics, including differential diagnosis. In an example, a relatively lower quality image of the OUT may be presented first to the operator or user of the sensor (e.g., as a preliminary check), with higher quality images requiring more processing time. A user or operator may have the option of terminating the processing of the higher quality output upon inspection of the lower quality output. The user or operator may have to explicitly trigger the processing of the higher quality image after inspecting the preliminary lower quality image. A user or operator may have the option of selecting one or more portions of the reconstructed image and request that additional post-processing be done to resolve more detail in those selected areas. These techniques are examples only, and not exhaustive.

Referring to FIG. 1, an example radio frequency (RF) sensing use case 100 is shown. In general, an RF sensing system 102 may be configured to transmit electromagnetic wave signals 102*a* that are scattered by an object 104 in the signal path. The RF sensing system 102 is configured to capture one or more scattered signals 104*a* and may determine characteristics about the object 104. For example, the range, velocity, and angle of the object 104 may be determined. Other properties such as size, physical composition, and pose may be determined. Properties may be determined based on time and phase and frequency information (e.g., Doppler) and amplitude information extracted from the RF signals. The RF sensing system 102 may include multiple transmit and/or receive antennas or antenna arrays (and corresponding transmit and/or receive chains) to improve phase analysis and actual or virtual beamforming. For example, phase shifting techniques (e.g., a Butler matrix) may be used to improve transmit and receive beam directivity gain. Other analog components such as power amplifiers (PAs) and low noise amplifiers (LNAs) may be used to enhance the transmit and receive gain in the RF sensing system 102.

Figure 2:
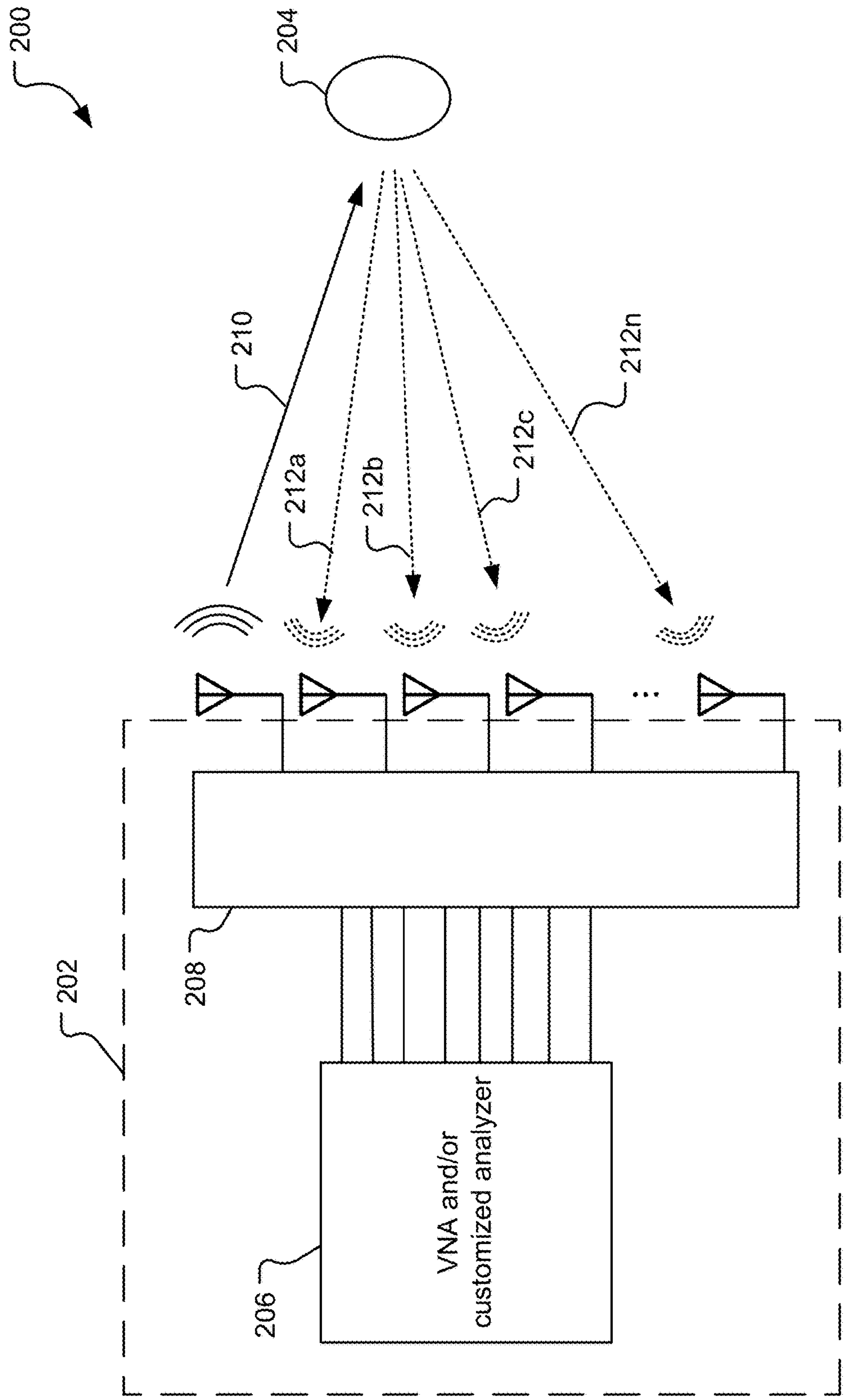
FIG. 2 is a block diagram of an example RF imaging system.

Referring to FIG. 2, a block diagram 200 of an example RF sensing system 202 is shown. The sensing system 202 includes one or more antennas configured to transmit RF signals 210 towards an object 204 and one or more antennas configured to receive scattered signals 212*a-n* from the object 204. The antennas may be operably coupled to an apparatus capable of determining the magnitude and phase of the transmitted and received signals such as a vector network analyzer (VNA) 206 and/or a customized analyzer 206 via a switching network 208. A transmit antenna may be excited at a time while the other antennas are configured to receive. In an example, the VNA 206 may be a commercial eight-port VNA configured to operate at frequencies of 8 GHz and higher to obtain scattering parameter measurements (i.e., S-parameter measurements). Other VNA, customized analyzer, and switching network configurations may also be used. In an example, a customized analyzer may be able to analyze received signals at the transmit antenna. Example VNAs may have different port configurations (e.g., 2, 3, 4, 8, 24, etc.) and a switching network may be configured to increase the number of ports the VNA may utilize. The transmitting and receiving antennas with the VNA 206 form the sensing system 202. In operation, the sensing system 202 may include N antennas and the VNA 206 (and potentially the switching network 208) will include N ports to which the antennas are connected. The VNA 206 may be configured to measure one frequency at a time and determine a subset of S-parameter data at each frequency. The S-parameter data may include phase and magnitude information for the transmitted and received signals. For example, since one port (e.g., one antenna) is transmitting at a time for each frequency, this enables the acquisition of respective transmission S-parameters and the reflection S-parameters at the receiving ports. In another example, the transmission S-parameters may be determined at a different position along the RF signal path than the reflection S-parameters. This may be repeated at each port to generate a scattering matrix (e.g., S-matrix) including N×N parameters at each frequency. In an example, scattering matrices may be larger or smaller than N×N, and may be represented by a vector when the diagonal components of the matrix are sufficient to achieve the desired performance. The RF sensing system 202 is an example, and not a limitation, as other RF sensing and radar system configurations may be used. For example, direct-RF technology may yield the magnitude and phase information for the transmitted and received signals of the RF sensing system 202. In another example, a customized analyzer comprising partial reflectometers may yield the magnitude and phase information for the transmitted and received signals of the RF sensing system 202.

One of ordinary skill in the art will recognize that VNA 206 may be a commercially available VNA and that not all the functions associated with a commercial VNA 206 may be used in a DT system. In an example, a subset of capabilities provided by a commercial VNA 206 are utilized in a DT system. In an example, a customized analyzer 206 may be utilized that includes a subset of the capabilities provided by a commercial VNA 206. In another example, a subset of capabilities of a customized analyzer 206 may be designed for improved performance in a DT system. In an example, the dynamic range of the transmit and receive signals may be improved in a customized analyzer 206. Improved dynamic range may improve the acquisition speed and/or the spatial and/or permittivity and/or permeability resolutions of the DT system.

An example dielectric tomography system described herein may include at least one processor and at least one sensor configured to perform RF sensing as described in FIGS. 1 and 2. The at least one processor and at least one sensor may be integrated into a single physical structure or unit, or the processor and the sensor may be distributed across multiple physical structures or units. The functions associated with the processor and sensor described here are for illustrative purposes. The functions ascribed to the processor and/or the sensor may be performed by either the processor or the sensor or both and the combination of the functions described herein may be performed by components in the processor and/or the sensor or both.

In general, a dielectric tomography system may comprise, generate and/or receive electrical signals, sometimes also referred to as signals and/or communication signals and/or data signals and/or data, that may be conveyed between the processor part and the sensor part, and/or the sensor part and the processor part, using communication protocols that include wired protocols, wireless protocols, optical protocols, and the like. By way of example, but not a limitation, signals may be conveyed between the system parts using Ethernet, Bluetooth, Bluetooth-LE, WiFi, IEEE 802.11, WiFi-ah, ZigBee, Z-wave, 6LoWPAN, Thread, RFID, Cellular, NB-IoT, 2G (GSM), 3G, 4G, 5G, NFC, LTE Cat 0,1, & 3, LTE-M1, LoRaWAN, LTE-M, SigFox, Ingenu, Weightless-N, Weightless-P, Weightless-W, ANT, ANT+, DigiMesh, EnOcean, Dash7, WirelessHART, ATM, TCP/IP, UDP/IP, PNNI, signaling protocols and/or the signals may be conveyed using new and/or proprietary signaling protocols.

In an example, optical signals may be conveyed between the processor part and the sensor part, and/or the sensor part and the processor part, using communication protocols that include protocols used for fiber optic communications and/or free space optical communications. The electrical signal protocols may be used to modulate and decode an optical signal. As an example, and not a limitation, optical signals may be conveyed between the system parts using SDH, SONET, WDM, OTN, ATM, TCP/IP, UDP/IP, MPLS, OSRP, FSFP, PNNI signaling protocols and/or the optical signals may be conveyed using new and/or proprietary signaling protocols.

Signals may be conveyed between the components of the dielectric tomography system using optical communication protocols, electrical communication protocols, or a combination of electrical and optical communication protocols. Electrical and optical signals may be transmitted over wires, traces, backplanes, connectors, cables, fibers, waveguides, and the like and/or they may be transmitted over free space or wirelessly for at least some portion of their path.

The signals in the dielectric tomography system may be coded or encrypted. As an example, and not a limitation, signals may be encoded using error correction codes, privacy codes, routing codes, and/or to be compliant with signal and data formats identified in standards, and the like. The signals in the dielectric tomography system may be coded to comply with standards set by standards development organizations such as Health Level 7 International (HL7), National Council for Prescription Drug Programs (NCDPD), International Health Terminology Standards Development Organizations (IHTSO), DirectTrust Standards, Clinical Data Interchange, the World Health Organization (WHO), and the like.

In an example, the signals in the dielectric tomography system may be coded to be compliant with the DICOM (Digital Imaging and Communications in Medicine) protocol. The signals in the dielectric tomography system may be coded to meet HIPAA, GDPR, DICOM, FHIR, SCRIPT, and/or CDISC standards. The signals in a dielectric tomography system may be coded to meet C-CDA, HL7 v2 and v3, and/or USCDI standards. New standards and protocols may be introduced and/or older standards may evolve over time, and it is the intent of this description to cover all signaling standards and protocols that may apply to a dielectric tomography system.

The processor and sensor may be relatively close to each other such as in the same housing, the same room, and/or the same building. In an example, the processor and/or some portion of the processing functions of the dielectric tomography system may be performed at a distance from the sensor. For example, the processing functions of the dielectric tomography system may utilize cloud resources (e.g., edge servers) and/or may be performed on remote servers and/or clusters and/or computer processing units (CPUs) and/or graphics processing units (GPUs).

Data obtained by a sensor may be processed and transformed into one dimensional (1D) and/or two dimensional (2D) and/or three dimensional (3D) images by a processor collocated with the sensor. For example, microwave signals may be transmitted and received by the RF sensing system 202 with the image processing performed by an applications processor (not shown in FIG. 2). The images may show permittivity and/or relative permittivity values of the regions and/or components of the object 204. In an example, the application processor may be a remote resource, such as a remote server or similar computing device that is communicatively coupled to the RF sensing system 202. Other processing configurations may also be used. For example, processing may be done partly on one or more local computers and partly on one or more remote computers or resources. The processing may be carried out on and/or the signals may be transmitted through a distributed network of computers.

A dielectric tomography system may be configured to illuminate an object and/or an object under test (OUT) with microwave electromagnetic fields, collect and process scattered electromagnetic fields into data signals, process data signals based on one or more reconstruction algorithms (e.g., solve the "inverse problem"), and record and/or display imaging data to be interpreted by a user and/or an analysis tool.

Referring to FIGS. 3A-3D, diagrams of example sensors in dielectric tomography systems are shown. In general, a sensor in a dielectric tomography system may include at least one microwave transmitter and receiver and/or transceiver for transmitting and receiving microwave signals. As used herein, microwave signals may refer to electromagnetic fields, near-fields, far-fields, or both, in the frequency range between 10 MHz and 300 GHz of the electromagnetic spectrum. The frequencies may vary and in some examples the microwave or RF signals may have frequencies in the range between 10 MHz and 10 GHz.

Microwave or RF electromagnetic fields generated by at least one microwave transmitter and/or transceiver may interact with components and/or objects and/or scattering devices within the sensor and may interact with at least one object under test (OUT) placed within the sensor. The RF electromagnetic fields may be scattered as a function of the complex permittivity of any components and/or objects and/or scattering devices and/or OUTs that they encounter. RF signals that are transmitted, reflected, scattered, diffracted, back-scattered, forward-scattered and the like may be referred to as "scattered" signals in this disclosure.

As described in FIGS. 1 and 2, for example, the scattered RF electromagnetic fields may be received by at least one microwave receiver and/or transceiver and processed to recover the phase and magnitude information of the scattered signal as it is received at that receiver location. The phase and magnitude information of the scattered microwave electromagnetic fields, sometimes referred to as the data, may be used to determine the complex permittivity of any components and/or objects and/or scattering devices and/or OUTs within the sensor. One or more reconstruction algorithms may be used to determine and provide an image of the permittivity distribution that most likely generated the scattered signals. Differences in permittivity may be associated with different normal tissue types and/or with unhealthy and/or damaged and/or abnormal tissue types. In a medical imaging example for human tissue, the OUT may be some portion of the body disposed within a sensor that may be imaged in a substantially normal operating state without the addition or insertion of any tracers or materials injected to increase the contrast in permittivity of different tissues. In an example, tracers may be used to improve the permittivity contrast between different tissues. In another example, tracers may be used to detect permeability differences between tissues. The tracers may comprise magnetic materials, ferromagnetic materials, paramagnetic materials, and the like.

Figure 3A:
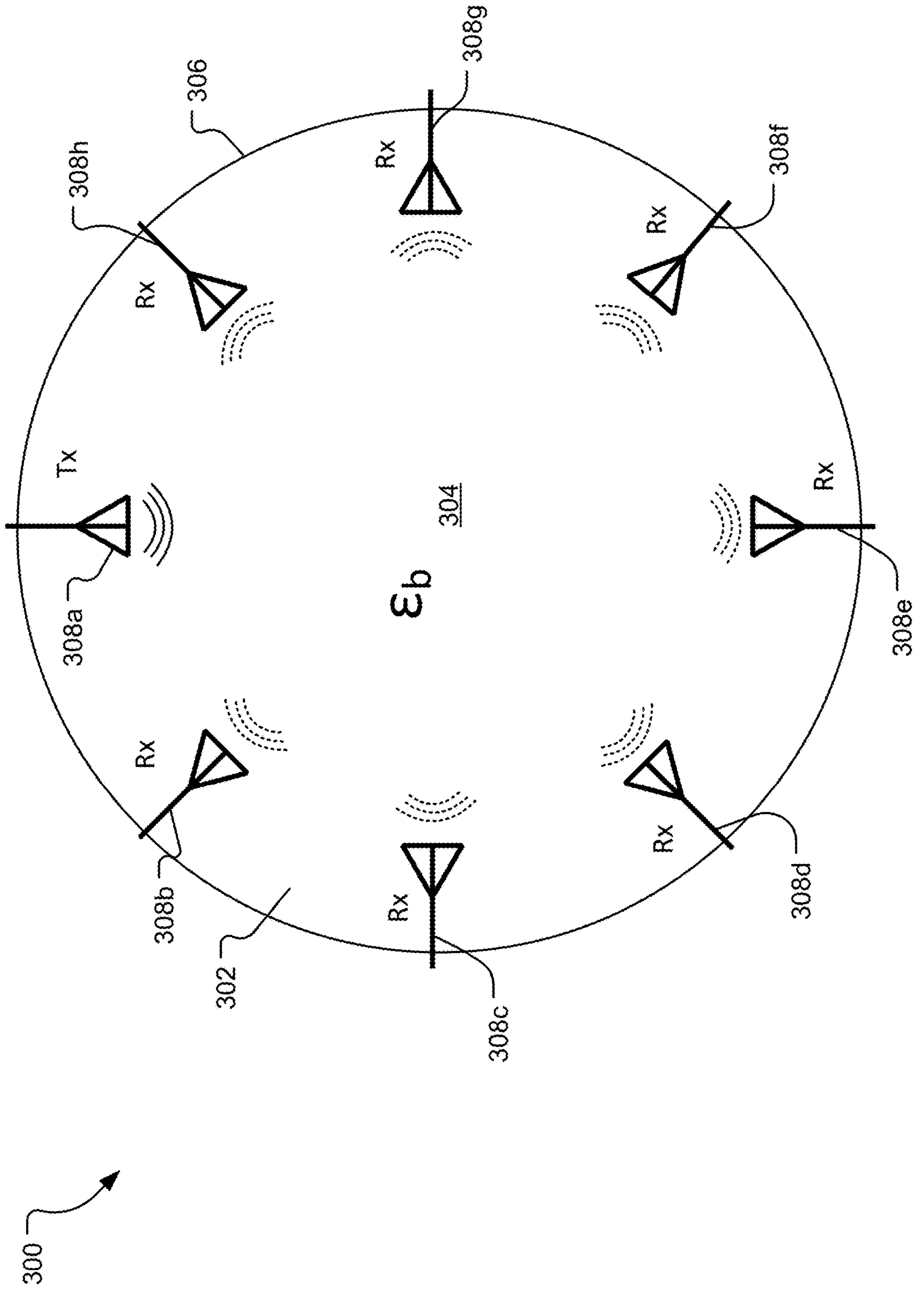
FIGS. 3A-3D are top-down diagrams of example sensors in dielectric tomography systems.
Figure 3B:
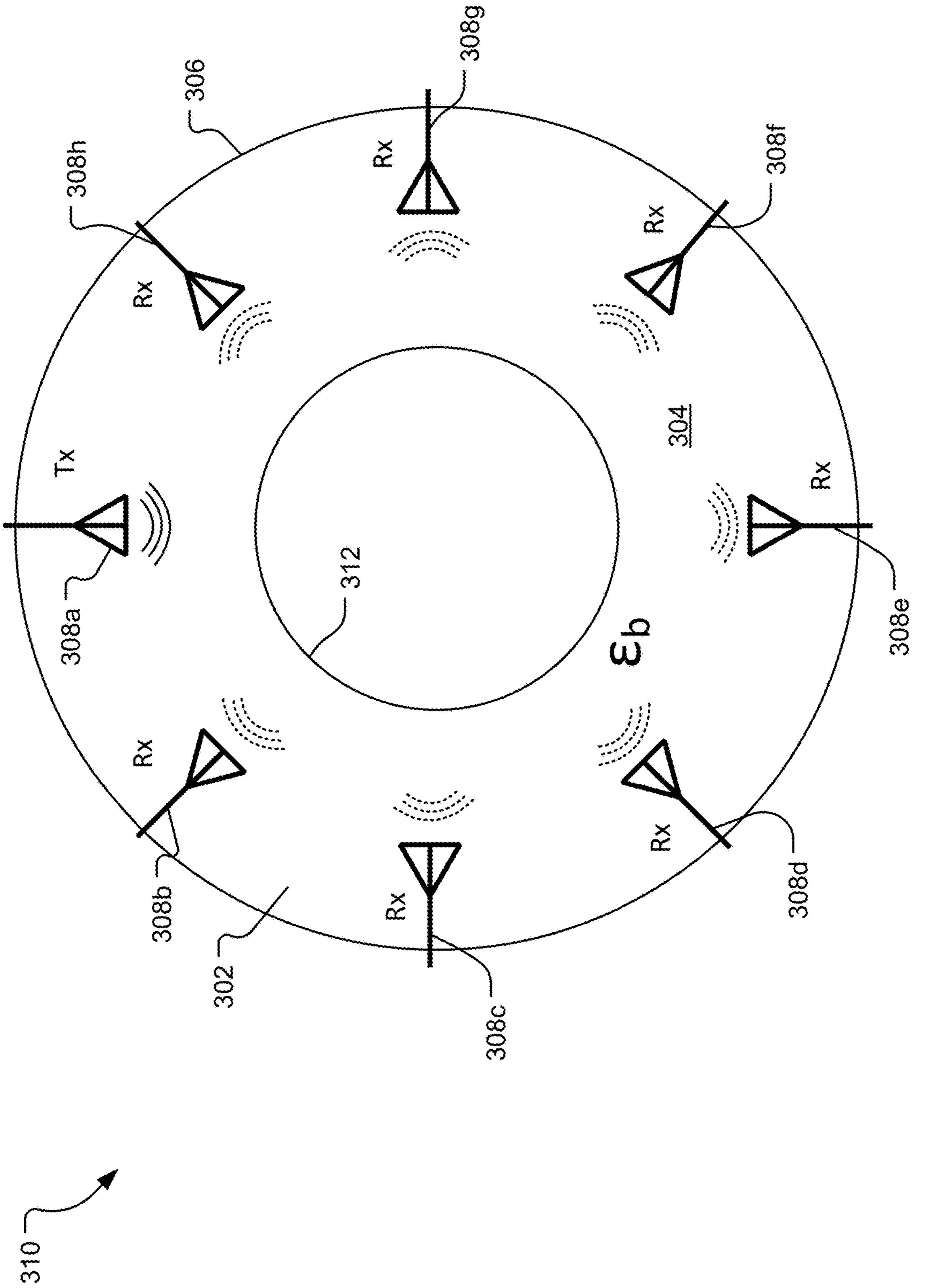

Referring to FIG. 3A, a sensor 300 includes a sensing region or domain 302 with an outer wall 306 (e.g., edge) that is substantially cylindrical in shape. Other sensor shapes may also be used. For example, a sensor may be shaped as a cube, box, sphere, dome, ellipsoid, annulus, and/or may have a cross-sectional area that is shaped as a circle, square, hexagon, ring, disk, oval, or some combination of straight and curved edges, and the like. A coupling medium 304 is disposed within the outer wall 306. The coupling medium 304 may be solid, gel, liquid, foam, emulsion, or gas, and may be a mixture of solids and/or gels and/or liquids, and/or gasses and/or combinations of materials in various phases and may be characterized by a local or average or effective permittivity, eb. In an example, the coupling medium 304 may be air or comprise at least a portion of air (e.g., the sensor 300 is partially filled or is filled with aerated material). Referring to FIG. 3B, a sensor 310 may include an inner wall 312 in the sensing region 302 and coupling medium 304 may be disposed between the inner wall 312 and the outer wall 306. The inner wall 312 may be configured to form a compartment or other region enclosed by a bounded area. In general, an OUT may be positioned within the volume created by the inner wall 312. For example, for a annular shaped sensor such as depicted in FIG. 3B, an OUT may be positioned in the cylinder shaped volume formed by the inner wall 312. In an example, the inner wall 312 may be configured to hold or align or guide a cup and/or vessel and/or container and/or compartment and/or volume and/or insert, that comprises a scattering device or an object to be sensed or an OUT to be sensed by the system. A region nearest to a scattering device or an object being sensed and/or an OUT may be referred to as the imaging region and/or the object domain. Regions closer to transceivers may be referred to as sensor domains.

In an example, the sensors 300, 310 include the sensing region 302 which may be described as a cylinder, a sphere, a dome, a half sphere, an annulus, a half-annulus, a donut, a spheroid, an ellipsoid, a cube, a box, a tank, an enclosure, and the like. In an example, the sensing region 302 may include one or more compartments (e.g., multiple inside walls 312) forming shapes such as cylinders, cups, spheres, domes, half spheres, annulus', half-annulus', donuts, spheroids, boxes, triangles, diamonds, and the like configured to accommodate an object to be imaged. The coupling medium 304 may be disposed around the compartments, such as around the inner wall 312 in the sensor 310. The compartments may extend for the entire length or height of the sensing region 302, or they may be taller or shorter than the length or height of the sensing region 302. (See for example, FIG. 4, for a side view diagram 400 of the example sensor 300 with an outer wall 306 of height "h".) The cross-sectional shape and/or area of the compartments may change as a function of height and/or depth of the coupling region. The compartments may be open or closed, empty or full or partially full of some material. In an example, the compartments may enclose at least some amount of air and/or other gas, water, oil, kerosene, gelatin, glycerin, metal, alcohol, emulsion, plastic, patterned material, gelatin, silicone rubber, aluminum oxide, polysorbate, surfactants, coupling medium, or any combination thereof, and the like. The sensing region 302 may include an inner wall 312 or edge that may be described as a compartment enclosing air or another compartment. The volume between the outer wall 306 and the inner wall 312 of the sensing region 302 may be referred to as the sensor domain.

The sensor 300 may include one or more microwave transmitter and/or receiver and/or transceiver antennas 308*a*-308*h*. Some or all the antennas 308*a*-308*h*, with or without their associated electronics, may be integrated into and/or placed flush against the outer wall 306 or edge of the sensor 300. The antennas 308*a*-308*h* may be directional antennas configured to emit electromagnetic fields into the sensing region 302. In an example, the antennas 308*a*-308*h* may be configured and disposed to conform to the outer wall 306 of the sensor 300 and may be backed with a cavity and/or a conducting material and/or an electromagnetic absorbing material and/or and electromagnetic absorbing surface. The antennas 308*a*-308*h* may be configured to radiate substantially linearly polarized electromagnetic fields, circularly polarized electromagnetic fields, elliptically polarized electromagnetic fields, variable polarized electromagnetic fields, and/or other combinations of polarizations. The antennas 308*a*-308*h* may comprise crosspolarized antennas and/or may generate signals whose polarizations are orthogonal, or nearly orthogonal relative to each other.

Figure 3C:
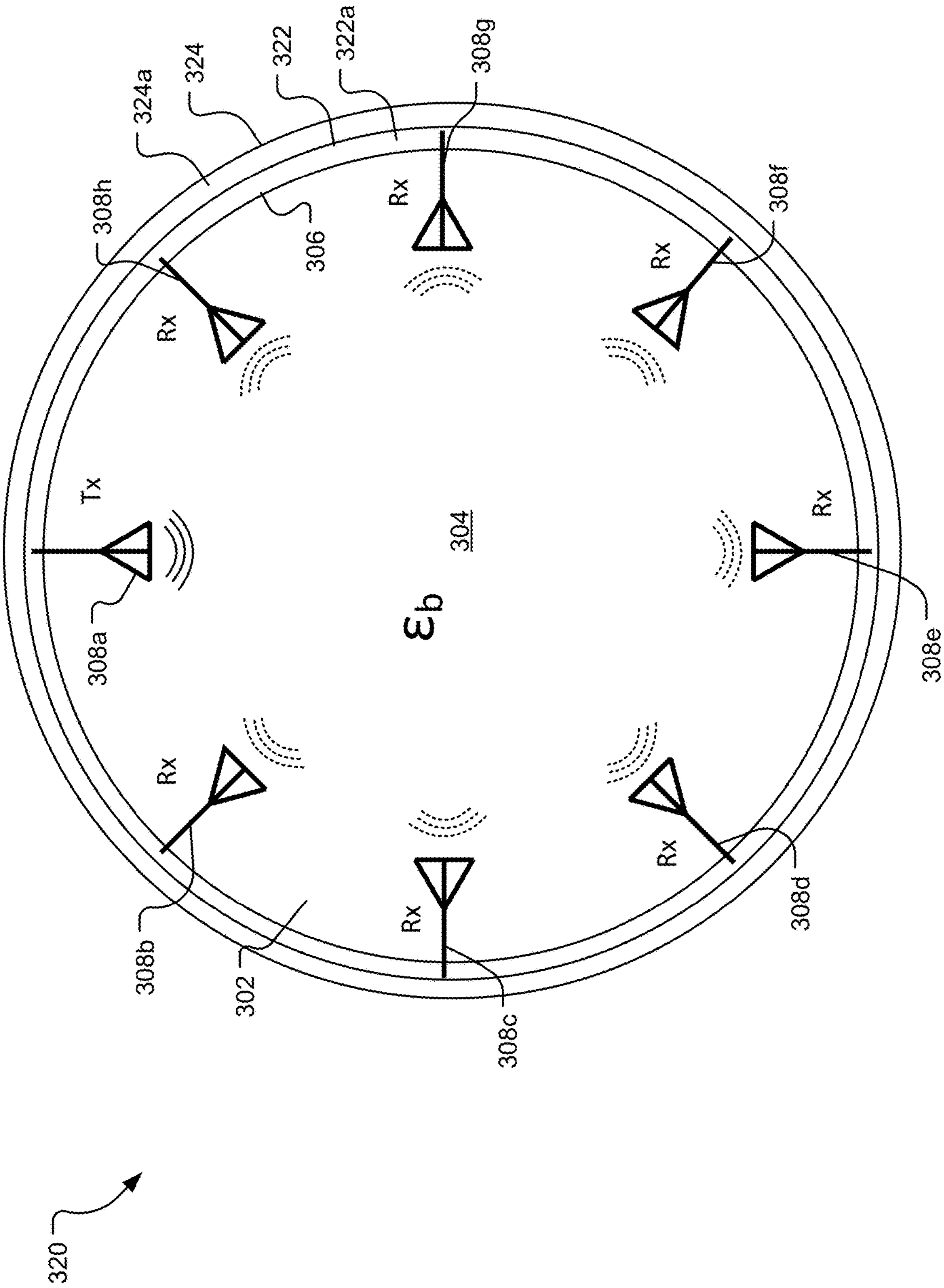

The outer wall 306 of the sensor 300 may also define the edge of the sensing region 302 and/or the sensor domain. In an example, the outer wall 306 may be comprised of a conductor such as copper, aluminum, tin, conducting foils, and the like. Referring to FIG. 3C, the outer wall in a sensor 320 may further comprise multiple layers of materials 322, 324 such that some or all the layers may be materials that are poor reflectors of electromagnetic fields. The layers of materials 322, 324 may comprise anti-reflection materials, absorptive materials, and the like. The layers of materials 322, 324 may be designed to behave as “matched” and/or “perfectly matched” layers and/or boundaries, as would be understood by a person of ordinary skill in the art. The layers of materials 322, 324 may comprise solid, liquid, gel, foam, emulsion, gas, rigid, semi-rigid and/or flexible materials. These materials may be layered or structured to present certain impedances to the electromagnetic fields of the system. The layers of materials 322, 324 may consist of concentric layers of materials and, in an example, may include compartments 322*a*, 324*a* filled with different materials (including air). In another example, the outer wall in a sensor 320 may further comprise at least one layer of material 322 or 324 that is a good conductor and that may substantially reflect electromagnetic fields. In another example, the outer wall in the sensor 320 may comprise acrylic.

Figure 3D:
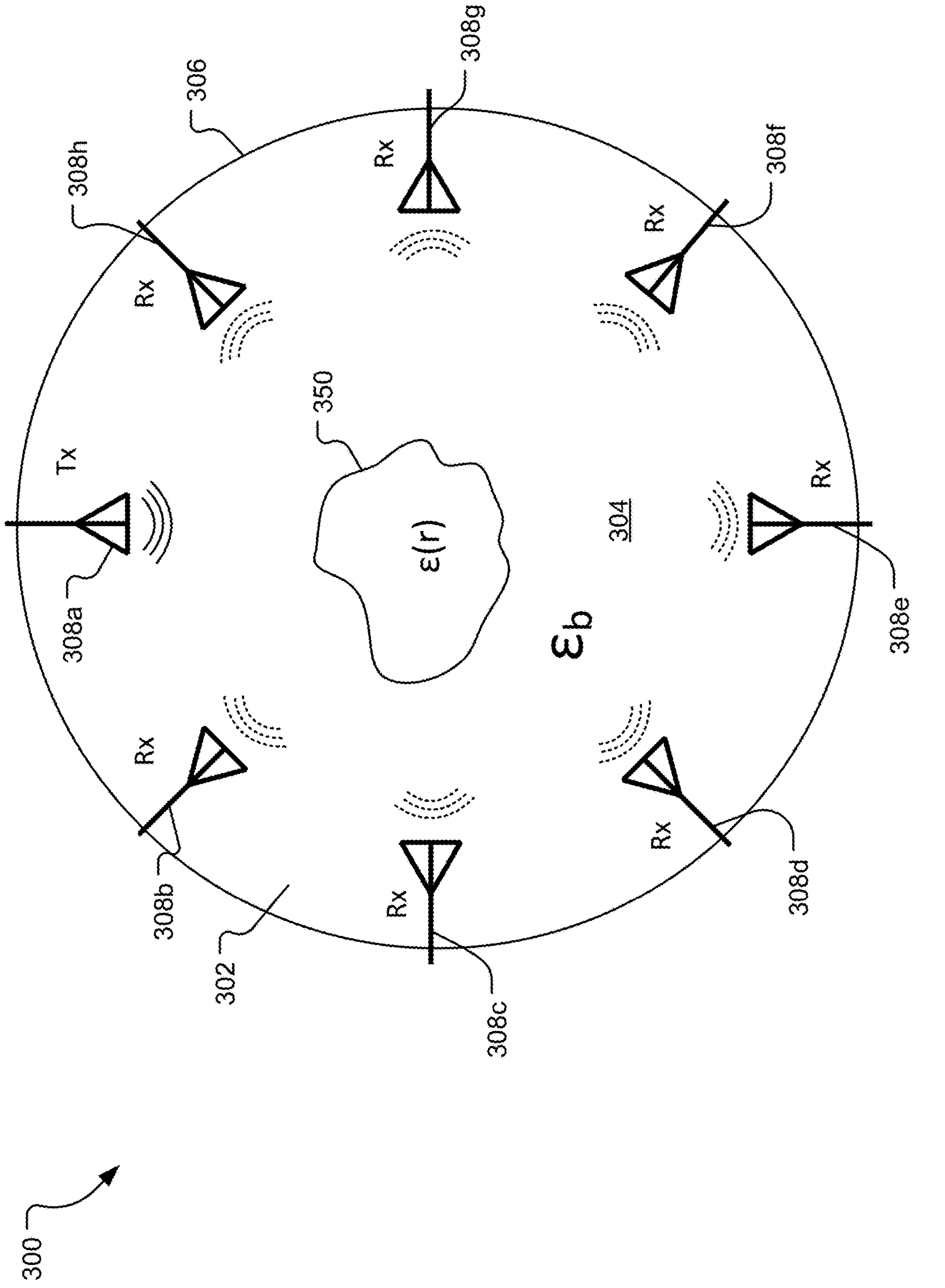

In an example, referring to FIG. 3D, the sensor 300 may be configured to move around a position where an object 350 (e.g., OUT) may be placed. For example, the sensor 300 may be configured to translate along any axis; the x-axis, the y-axis and/or the z-axis (up and down, side-to-side, etc.). The sensor 300 may be configured to tilt along any axis, and to rotate around an axis. The sensor 300 may be configured to move, translate, tilt and/or rotate in one or more directions, simultaneously or in a succession of steps. In an example, the sensor 300 may be configured to rotate 360 degrees around the object 350, in 5-degree steps. In another example, the sensor 300 may be configured to rotate 360 degrees around an object 350 in 5-degree steps and then translate up or down 5 mm relative to the object 350 and repeat the rotation. In yet another example, the sensor 300 may be repeatably rotated by a fixed and/or variable angle and translated by a fixed and/or variable distance, over a range appropriate to achieve the desired imaging. Scattered electromagnetic fields may be transmitted and received for each relative position of the sensor 300 and the object 350 and/or at each frequency of the transmitted signals. The examples above are not a limitation, as other rotations, translations, tilts, step sizes, and the like may be used.

In an example, referring to FIG. 3D, the object 350 may be configured to move within the sensing region 302. For example, the object 350 may be configured to translate along any axis; the x-axis, the y-axis and/or the z-axis (up and down, side-to-side, etc.). The object 350 may be configured to tilt along any axis, and to rotate around an axis. The object 350 may be configured to move, translate, tilt and/or rotate in one or more directions, simultaneously or in a succession of steps. In an example, the object 350 may be configured to rotate 360 degrees within the sensing region 302, in 5-degree steps. In another example, the object 350 may be configured to rotate 360 degrees within the sensing region 302 in 5-degree steps and then translate up or down 5 mm relative to the sensing region 302 and repeat the rotation. In yet another example, the object 350 may be repeatably rotated by a fixed and/or variable angle and translated by a fixed and/or variable distance, over a range appropriate to achieve the desired imaging. Scattered electromagnetic fields may be transmitted and received for each relative position of the sensor 300 and the object 350 and/or at each frequency of the transmitted signals. The examples above are not a limitation, as other rotations, translations, tilts, step sizes, and the like may be used.

In general, the generation and measurement of radiofrequency signals may be accomplished with a plurality of transmitters and/or receivers and/or transceivers, all of which may be referred to as transceivers within this disclosure. In an example, each antenna in the example sensors provided herein may have its own dedicated transceiver. In other examples, one or more of the antennas in the example sensor may be connected to a transceiver (or to a dedicated transmitter and a dedicated receiver, possibly collocated on a single circuit board) through a radiofrequency (RF) switch matrix such as a crossbar switch. Example switch matrices include and may comprise, but are not limited to blocking switches, non-blocking switches, super non-blocking switches, absorbing switches, single pole double throw switches, single pole quadruple throw switches, electromechanical switches, solid state switches, including those based on PIN junctions, diodes, transistors, and the like, multiplexers, demultiplexers, crossbar switches, cross-point switches, micro-electromechanical (MEMs) switches, combinations of these switches, and the like. In an example, the antennas may be grouped into sets, each connected to a transceiver through a switch matrix. In this disclosure, transceivers may be understood to include at least one antenna.

In an example, RF transceivers may be connected to a central processing unit in a star topology. A central processing unit may be implemented as a microcontroller and/or a field programmable gate array (FPGA) and/or an application specific integrated circuit (ASIC) and/or other programmable logic device. In an example, a central processing unit may be implemented directly on a personal computer or similar device. In another example, transceivers may be grouped together and driven and/or controlled by a processor that may communicate with a central processing unit that communicates with the multiple groups of transceivers. In embodiments, groups of transceivers may receive their clock, local oscillator, and source signals from a local processing board that is connected to a central processing unit that communicates with multiple groups of transceivers.

In an example, an RF source signal may be generated and shared amongst multiple antennas and/or electronic paths feeding various antennas and/or transceivers by one or more couplers or switches. A local oscillator (LO) signal may be generated and shared amongst various mixers and other components in the transmit, receive, and measurement/characterization paths of the electronic signals and/or transceivers. A clock signal may be generated and shared amongst various transceivers and/or transceiver components. In an example, transceivers in a dielectric tomography system may transmit and receive RF, LO, and/or clock signals that have been generated with the intent of being distributed to various antennas via switches, passive splitters, resistive splitters, couplers, and the like.

The antennas in the sensors may be bowtie, wired bowtie, dipole, Vivaldi, half-ellipse, disk, planar disk, planar half-ellipse, spiral, loaded dipole, tapered slot, eye-shaped slot, cavity-backed wide-slot, tapered slot, slot, horn, and/or fractal horn antennas, and the like. In an example, the antennas may be hexagonal horn antennas and/or may be a hexagonal horn antenna with an abrupt radiator. The antennas may comprise an array of antennas such as an aperture array and/or a MIMO (multiple input multiple output) array and/or a shielded array. The arrays may be linear arrays, one-dimensional, two-dimensional, or three-dimensional arrays. The antennas may be substantially two-dimensional such as when they are formed using planar circuit board technology. In an example, the antennas may be substantially one-dimensional such as straight wire antennas, or substantially three-dimensional such as traditional horn antennas. The antennas may be printed using substantially copper traces, platinum traces, and the like, and may be manufactured using printed circuit board techniques. The antennas may be printed using flexible circuit technologies. The antennas may be planar and may be planar printed circuit board (PCB) antennas. The antennas may be of an ultra-wideband design with high front-to-back ratio such as a folded bowtie, cavity-backed or reflector-backed bowtie. The antennas may be installed in cavities along the perimeter of a sensor, such as aligned with opening along an outer wall 306 of a sensing region and may be backed with RF absorbing materials to prevent unwanted interference paths with other antennas and interference with external signals. In an example, the antennas may be installed in cavities along the perimeter of a sensor, such as aligned with an opening along an outer wall 306 of a sensing region and may be backed with conducting materials to prevent unwanted interference from signals outside the sensor. In another example, the antennas may be installed in cavities along the perimeter of a sensor with an outer wall 306 of a sensing region comprising acrylic and allowing electromagnetic signals to be launched into the sensor from any radial position.

In an example, the antennas may radiate substantially sinusoidal signals. These signals may be referred to as single frequency signals and/or narrow band signals. The antennas may radiate sinusoidal signals at different frequencies, either one at a time or more than one frequency simultaneously. The antennas may radiate signals that may be described as a pulse, or an impulse waveform and such signals may be understood to have a defined time duration. The antennas and/or transceivers may be configured to radiate relatively broad bandwidth signals. Broad bandwidth signals may include arbitrary waveforms that may be reconfigurable and may be chosen to preferentially identity certain types of permittivity and/or permeability discontinuities. The antennas may be designed to be wide-band or ultra-wideband so that a large range of sinusoidal signals and/or a wide-band signals, such as an amplitude modulated, frequency modulated, phase modulated, and/or pulse position modulated signals may be efficiently emitted and received by the antennas. The required efficiency of the antennas may be different for different sensor applications and designs.

The antennas and their associated circuitry may operate as transmit antennas, receive antennas, and/or both transmit and receive antennas. The antennas may transmit during certain periods of time, may receive during certain periods of time, may transmit and receive at the same time for certain periods of time, and they may switch operation amongst any of these modes, or combinations of modes, under electronic control. The antennas and/or antenna circuits may comprise impedance matching circuits and/or similar tunable impedance matching networks. The impedance matching network may be varied or tuned to account for variable distances between the antennas and the sensing region, the antennas and the OUT, the electric parameters of the coupling medium, the presence or absence of additional objects and/or compartments within the sensing region and the like. The impedance of an impedance matching network in the antenna and/or antenna circuits may be controlled. The control may be manual and/or automatic, and/or a combination of manual and automatic. Automatic control may be implemented via open loop and/or closed loop techniques. Closed loop techniques may be used to vary the impedance of an impedance matching network in response to a measured parameter in the sensor and/or system. The measured parameters may include distances and/or spacings such as distances between the antennas and the sensing region, distances between the antennas and a compartment in the sensor, distances between the antennas and an object, distances between the antennas and an OUT, distances between antennas and inner and/or outer walls of the compartment and distances between the antennas themselves. Resistive loading techniques may be used in the antenna and/or antenna circuit designs. The antennas may be configured with a high pulse fidelity. Antenna designs may be configured to reduce group delay. Group delay of the antennas may be characterized during sensor and/or system operation and/or calibration. The measured group delay may be a system parameter that may be stored in the system and/or may be a system value and may be used in some portion of the operation software of the system. In an example, the measured group-delay may be used to alter and/or process signals received from the antenna. In an example, matching components to substantially 50 ohms, such as (50-ohm) transmission lines and/or (50-ohm) terminations, and/or 50-ohm input and/or output impedances, and the like, may provide sufficient impedance matching.

The associated circuitry of the antenna may include a reflectometer. In an example, the reflectometer may be a partial reflectometer or a non-complete reflectometer. Signals generated and received in and by a reflectometer may be used to calibrate and/or characterize the sensor in a manner similar to those known in the art for calibrating vector network analyzers (see, for example, IEEE Trans. Microw, Theory Tech., 56.3, pp. 693-699, (2008) and IEEE Trans. Microw, Theory Tech. 60.12, pp. 3844-3855, (2012).) In an example, a partial reflectometer may be used to determine the error coefficients for the transceivers of the sensor. In an example, a new type of partial reflectometer includes two high-isolation switches to switch between transmitting the signal and using the reflectometer in receive mode of the transceiver to measure the magnitude and phase of received signals to determine the error coefficients for the transceivers when a characterization scatterer is disposed in the sensor and to provide data signals when an OUT is disposed in the sensor. This new type of reflectometer may provide improved signal-to-noise performance and/or dynamic range in determining the amplitude and phase of transmitted and received RF signals. In an example, characterization coefficients for the model of the measurement domain may be determined using the dual-gain partial reflectometer and a known and/or characterization scatterer. The dual-gain reflectometer is a new type of partial reflectometer whose performance may be controlled. The control may be manual and/or automatic, and/or a combination of manual and automatic. Automatic control may be implemented via open loop and/or closed loop techniques. Closed loop techniques may be used to vary at least one switch position of an dual-gain partial reflectometer in response to a measured parameter in the sensor and/or system.

In an example, some or all the radiofrequency circuits associated with each transceiver antenna may be located in close proximity to their respective antennas. Such embodiments may be advantageous when minimizing the length of RF cabling and/or reducing crosstalk between different sensing circuits is desirable. In another example, multiple transceivers may be driven and/or controlled by circuitry located in close proximity to the group of multiple transceivers that may communicate with a central processing unit that communicates with the multiple groups of transceivers. Such embodiments may be advantageous when minimizing the size of circuit boards, or taking advantage of cost advantages of multi-device chips is desirable. These are some not all examples and are not meant to be limiting.

The antennas may be operated in a manner similar to time-domain and/or frequency domain ground penetrating radar systems. In an example, the antennas may radiate shaped and/or time limited waveforms that may be referred to as pulse or impulse or arbitrary waveforms. The antennas may be configured to radiate signals whose amplitude, and/or phase, and/or frequency and/or time characteristics and/or frequency characteristics and/or pulse positions have been modulated in discrete and/or digital formats and/or in continuous and/or analog formats. The antennas may radiate waveforms that may be described as carrier free, stepped frequency continuous wave (SFCW), frequency modulated continuous wave (FMCW), frequency modulated interrupted continuous wave (FMICW), noise modulated continuous wave (NMCW), or any combination of the above.

The transceiver antennas, coupling medium and compartments may be designed as a single "guided wave" assembly. The electromagnetic properties of this assembly may be configured such that microwave signals are substantially guided by the coupling medium/media and its enclosures and/or compartments. The guided wave assembly may at least partially surround a scattering device and/or an object and/or an object under test. In an example, the guided wave assembly may be an annular compartment that holds some amount of coupling media. The annular compartment may include a top 352*a* and/or a bottom 352*b* ring-shaped and/or disk-shaped wall or plate that is comprised of conducting material such as copper, aluminum, silver, gold, platinum, a metal alloy, or any type of conducting material. (See FIGS. 5A-5C for example.) The outer wall 306 of the annular compartment may comprise a conducting material with holes or cutouts (see FIG. 9) or discontinuities where the transceivers are located so that the transceivers may emit and receive signals from the guided wave assembly. The inner wall 312 of the annular compartment may comprise a material with a known and/or constant and/or measurable dielectric constant. The material of the inner wall 312 may be chosen so that the electromagnetic fields emitted and received by the transceivers may at least partially pass through the wall and interact with materials placed within the inside opening of the annular compartment.

In an example, the thickness and/or flatness and/or roughness and/or regularity of the top 352*a* and/or a bottom 352*b* ring-shaped and/or disk-shaped walls or plates may be specified to a tolerance. In an example, specifying the thickness may improve dimensional estimates of the sensor compartment and the ability to create an accurate electromagnetic model of the sensor domain. In an example, the top and/or bottom plates 352*a*, 352*b* may be ⅜" inches thick and their thickness tolerance may be specified to be +0.005 to −0.005 inches. In an example, the plates may comprise aluminum and may comprise specially heat-treated and stressed-relieved aluminum sheets. In an example, the aluminum plates may be MIC6 aluminum or a similar aluminum. In an example, specifying the flatness may improve dimensional estimates of the sensor compartment and the ability to create an accurate electromagnetic model of the sensor domain. In an example, the top and/or bottom plates 352*a*, 352*b* may be ⅜" inches thick and their flatness tolerance may be specified to be 0.015". In an example, the aluminum plates may be polished and/or sanded and/or treated in ways known in the art to improve the thickness tolerance, the flatness, the roughness, and the like of the conductive sheets that comprise any portion of the sensor.

A sensor may comprise one or more transceiver modules that may be operated either as microwave transmitters or microwave receivers or both, simultaneously, or at different times. The transceivers may be controlled to act as transmitters for a period of time, Ttx, and receivers for a period of time, Trx. In embodiments, there may be periods of time when the transceiver is neither transmitting nor receiving microwave signals, Td. In an example, the transceivers may operate in half-duplex mode (e.g., configured to transmit and receive but not both simultaneously). In an example, the transceivers may operate in full-duplex mode (e.g., transmit and receive simultaneously). A single transceiver may operate as a transmitter at a given time, and other transceivers may each transmit in turn following a time-division multiplexing (TDM) method. More than a single transceiver may operate as a transmitter at a given time. The relative gain and phase of such simultaneous transmitters may be determined ahead of time, or adaptively in real time, so as to more effectively focus the signal to and/or to preferentially probe particular regions of an object and/or an OUT. In an example, error coefficients for at least one of the transceivers may be determined ahead of time, or adaptively in real time, to calibrate and/or characterize the at least one transceiver in the sensor. In an example, the error coefficients may be at least partially determined by using a dual-gain partial reflectometer.

A transceiver module may be configured to transmit a continuous wave (CW) (e.g., sine or nearly single frequency) signal. In an example, the transceiver module may transmit a signal composed of several sinusoidal components substantially equally spaced in frequency space, either one at a time or transmitting multiple components at a time. The spectral content of this signal may be such that, in frequency space, a number of high-amplitude sine waves may be separated by a larger number of lower amplitude sine waves. This may be utilized to supplement the high-SNR signals required for quantitative reconstruction with a lower-SNR time-domain qualitative reconstruction method that provides an initial guess for the quantitative method, as well as additional consistency checks. The time domain pulse can be obtained by Fourier transforming the lower-SNR spectral content.

A transceiver or transmitter module may transmit a set of simultaneous CW tones distributed within a frequency band around a center frequency. In embodiments, each transmitting module may transmit such a signal around a center frequency F_{m} for a given amount of time T_{m}, then repeat the procedure for a frequency F_{m+1} with respective duration T_{m+1}, for a set of frequencies and durations denoted respectively by {F_{m} n=1, 2, . . . , M} and {T_{m} n=1, 2, . . . , M} for some number M. In embodiments, each interval T_{m} may be determined based on signal-to-noise ratio (SNR) requirements specific to its corresponding frequency range. The SNR may be determined dynamically during data acquisition.

In an example, as depicted in FIGS. 3A-3D, the transmitter/receiver modules including the antennas 308*a*-308*h* may be arranged to be equidistant or nearly equidistant from each other in a single plane (at a certain height from the top) of the sensor. In an example, the transmitter/receiver modules and antennas 308*a*-308*h* may be arranged to be equidistant or nearly equidistant from each other in multiple planes (at certain heights from the top) of the sensor. The transmitter/receiver modules and antennas 308*a*-308*h* may be arranged to be different distances from each other in a single plane or in multiple planes of the sensor.

Figure 4:
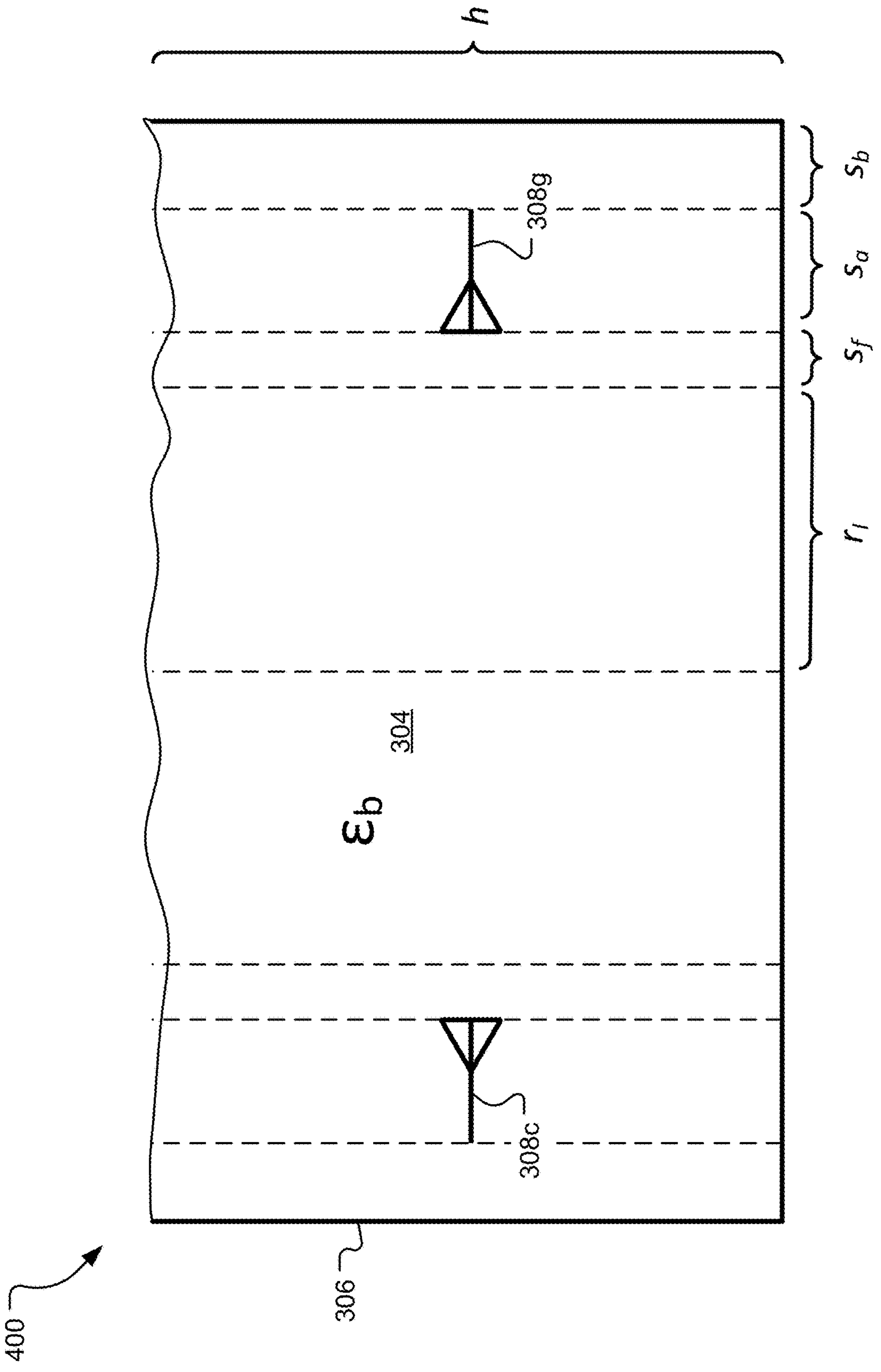
FIG. 4 is a side view diagram of an example sensor in a dielectric tomography system.

Referring to FIG. 4, a side view diagram 400 of the example sensor 300 is shown. The diagram 400 depicts two of the antennas 308*c* and 308*g* of the plurality of antennas 308*a*-308*h*. In this diagram, h is the height of the sensor, Sb is the gap between the back of the antennas and the container walls. In some systems, Sb is zero or not specified, such as when the antennas are mounted outside, or within a hole or a cut-out in, the outer wall 306 of the sensor. Sa is the length of the antennas and Sf is the distance between the object domain and the antennas. In an example, Sa may be close to zero and/or may be close to the thickness of sheet and/or board upon which an antenna has been printed. In an example, Sf may be the distance from the antenna to the inner wall 312 of the sensor 300. For sensors with cylindrical geometries, such as those depicted in FIGS. 3A-D, RI is the radius of the object domain. RI may be similar to the radius of a center compartment of the sensor, or it may be smaller or larger than the radius of any compartments. The antennas depicted 308*c*, 308*g* can be any antenna type.

Figure 5B:
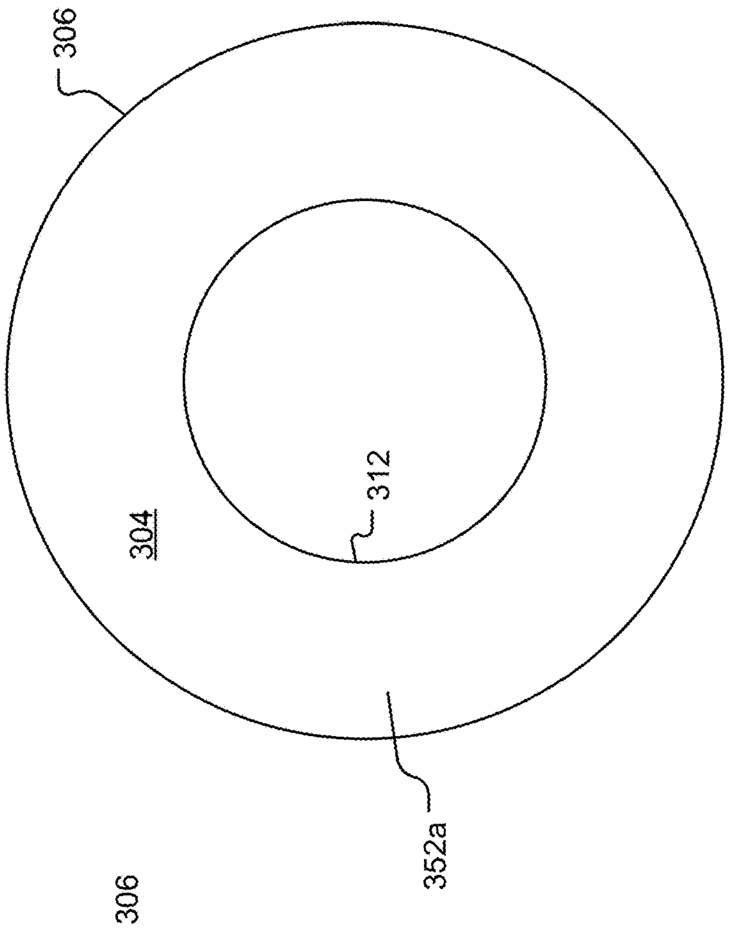
Figure 5A:
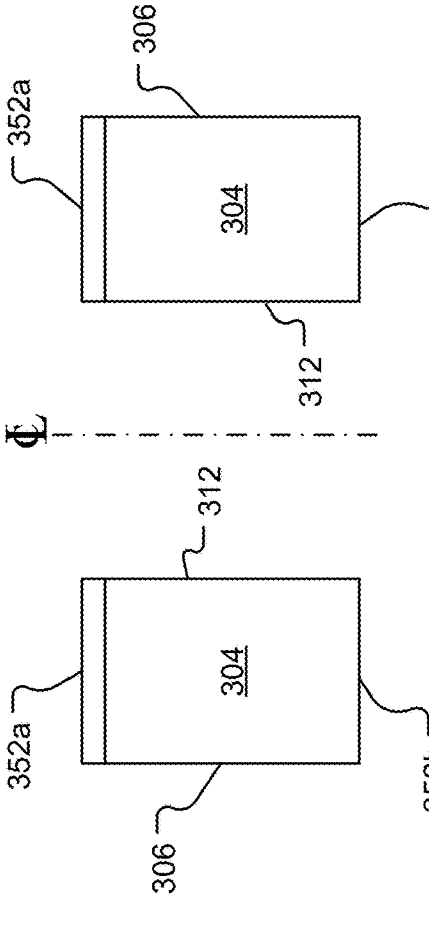
Figure 5C:
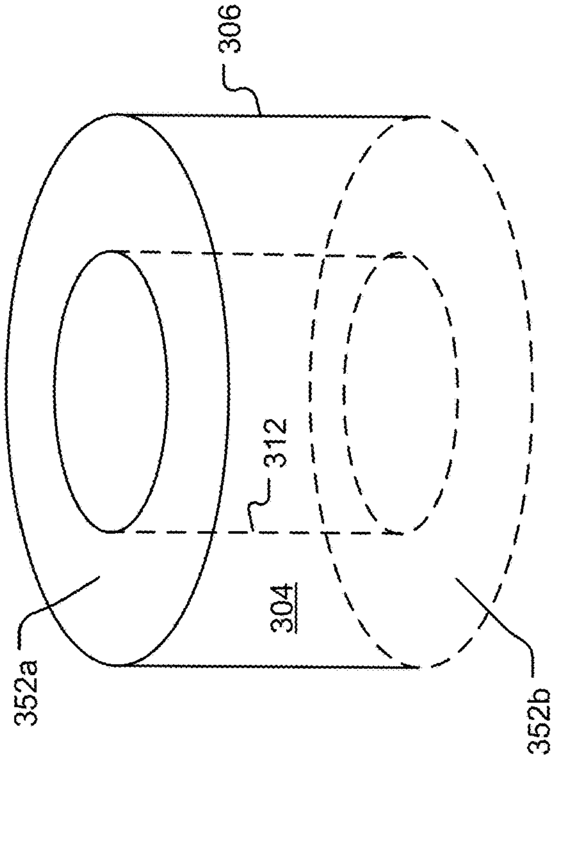

Referring to FIGS. 5A-5C, respective side, top and perspective views of the example sensor 310 are shown. The antennas 308*a*-308*h* are not shown in FIGS. 5A-5C. The sensor 310 forms an annular compartment including the at least one rigid or semi-rigid outer wall 306, that may be the same material or different materials from a bottom wall (or plate) 352*b*. The sensor 310 may include a top wall 352*a* (or plate). In an example, the sensor 310 may have an open top. The walls 306, 312, 352*a*, 352*b* may be flexible materials and/or they may comprise conducting materials. In an example, the walls 306, 352*a* and 352*b* may comprise conducting materials and the inner wall 312 may comprise a material that at least partially transmits the RF source and scattered signals. In an example, the inner wall 312 may comprise acrylic, polycarbonate, glass, plastic, an emulsion-to-air interface, and the like. In an example, the outer wall 306 may comprise acrylic, polycarbonate, glass, plastic, an emulsion-to-air interface, and the like. The coupling medium 304 may comprise a solid, liquid, gas, foam, gel, emulsion, and the like. The annular compartment may be fully or partially filled with coupling medium. In an example, the sensor 310 may be the annular shape depicted in FIGS. 5A-5C, but other compartments may also be formed.

Figure 6A:
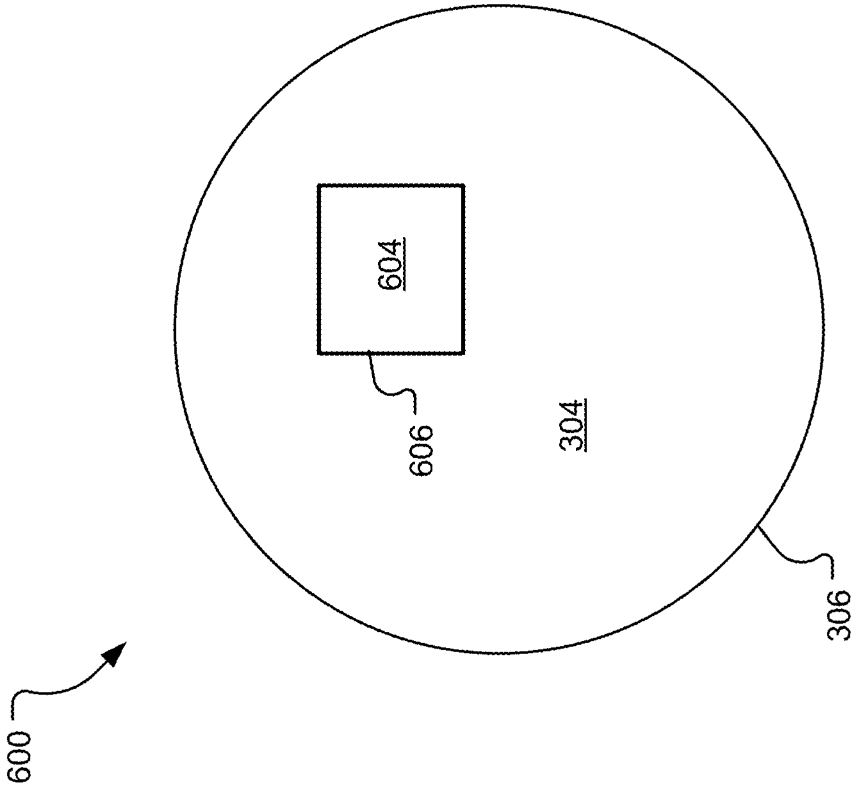
FIG. 6A is a top view of an example annular sensor in a dielectric tomography system with an offset chamber representing the object domain.

For example, referring to FIG. 6A, a sensor 600 with a square compartment 604 is formed with a square shaped inner wall 606. The square compartment 604 may be used as an object chamber and configured to accommodate an OUT. The square compartment 604 may be configured to move, for example by translation and/or rotation, within the area defined by the outer wall 306. Other shaped compartments may also be formed. For example, triangular, circular, oval, annular, half-annular, and other polygons and free formed shapes may be used to form one or more compartments. The compartments may be disposed in non-symmetric and/or offset from center positions within a sensor. In an example, the cross-sectional dimensions of the hole in the annular compartment may not be constant as a function of height, h, along the annular compartment.

Referring to FIGS. 5D-5E, top views of the example sensor 310 are shown. The antennas 308*a*-308*h* are not shown in FIGS. 5D-5E. The sensor 310 forms a half-annular compartment including the at least one rigid or semi-rigid outer wall 306, that may be the same material or different materials from a bottom wall (or plate) 352*b* (not shown). The sensor 310 may include atop wall 352*a* (or plate). In an example, the sensor 310 may have an open top. The sensor may include side walls 360*a*, 360*b*. The walls 306, 312, 352*a*, 352*b*, 360*a*, 360*b*, may be flexible materials and/or they may comprise conducting materials. The coupling medium 304 may comprise a solid, liquid, gas, foam, gel, emulsion, and the like. The half-annular compartment may be fully or partially filled with coupling medium. In an example, the sensor 310 may be the half annular shape depicted in FIGS. 5D-5E, but other compartments may also be formed. FIG. 5E shows a wall 360*c* extending between side walls 360*a*, 360*b* and forming a half-cylindrical inner opening in the sensor 310. In an example, all three walls 360*a*, 360*b*, 360*c* may be formed from a single conducting plate. In another example, the three ways are formed by individual conducting plates. In yet another example, at least one of the walls 360*a*, 360*b*, 360*c* may be comprise absorbing materials and/or layers as described in reference to materials and layers 322, 322*a*, 324, 324*a*, the outer wall 306 in FIG. 3C. As described for the annular compartment, a half-annular sensor 310 may include a square compartment 604 (not shown) that is formed with a square shaped inside wall 606. The square compartment 604 may be used as an object chamber and configured to accommodate an OUT. The square compartment 604 may be configured to move, for example by translation and/or rotation, within the area defined by the outer wall 306, the inner wall 312, and the side walls 360*a*, 360*b* and/or by the outer wall 306, the inner wall 312, and the side walls 360*a*, 360*b* and 360*c*. Other shaped compartments may also be formed. For example, triangular, circular, oval, annular, half-annular, and other polygons and free formed shapes may be used to form one or more compartments. The compartments may be disposed in non-symmetric and/or offset from symmetry positions within a sensor. In an example, the cross-sectional dimensions of the hole in the half-annular compartment may not be constant as a function of height, h, along the half-annular compartment.

Referring to FIG. 5F, top views of other example sensors 310 are shown. In general, these sensor compartments may be described as partial annuluses, and may be described as having at least some cylindrical symmetry. Cylindrical or partial cylindrical sensors 310 and/or sensor compartments may be analyzed, modeled, characterized, calibrated, and the like in cylindrical coordinates as part of the characterization and/or calibration and/or data analysis and/or reconstruction processes of the sensor system.

In an example, the compartment 604 within the sensor 600 may be movable around a position where an object and/or OUT may be placed. In another example, an object and/or OUT may move along with the compartment 604. Example movements include the compartment 604 being able to be translated along any axis; the x-axis, the y-axis and/or the z-axis (up and down, side-to-side, etc.). The compartment 604 may be able to be tilted along any axis, and to be rotated around any axis. In an example, the antennas 308*a*-308*h* (not shown in FIG. 6A) may be movable around a position where an object and/or OUT may be placed. Example movements include the antennas 308*a*-308*h* being able to be translated along any axis; the x-axis, the y-axis and/or the z-axis (up and down, side-to-side, etc.), as well as rotations around an axis of the sensor. The antennas may be moved all in tandem, in subgroups, or completely independently. The sensor 600, the compartment 604, and the antennas 308*a*-308*h* may be moved manually by a person (such as the person being imaged) or by a person (such as a technician) operating a system of levers, pulleys, jacks, belts, screw stages, rotation stages, gear boxes, planetary gear systems, and the like. The sensor 600 and the compartment 604 may be moved by a motor and/or levers, pulleys, jacks, belts, screw stages, hydraulic lifts, rotation stages, gear boxes, planetary gear systems, and the like. The movement may be based on electronic control with electronic signals being sent to and/or received from the sensor 600 and/or the compartment 604, to actuate and/or cease movement. The sensor 600 may be equipped with a motion encoder and/or position sensor (such as accelerometers, gyroscopes, inside out and/or outside in positioning systems, and other inertial sensors) and/or similar systems to assist with motion control and/or feedback and/or determining the position of an object being imaged. The position of the sensor 600 relative to the patient or OUT may be determined by and/or relative to conducting materials, meshes, patterned patches and the like positioned on the inner wall of the sensor 600, the outer and/or inner wall of the compartment, 604, and/or on a garment, flexible material, and/or coating at least partially covering or positioned over the outside surface of an object being imaged. The position of the sensor 600 relative to the patient or OUT may be determined by or with the assistance of external base stations. These base stations may employ methods such as optical or infrared cameras, lidar, ultrasound, inside out, outside in, and other position detection methods familiar to those skilled in the art.

In an example, the sensor 600 or compartment 604 may be moved to follow a certain path relative to where an OUT may be placed. The movement may follow a certain path before, after, or while the OUT is in the sensing domain. The movement may traverse along a single axis such as the x-axis, the y-axis or the z-axis. The movement may follow a path or paths that traverse the x-y plane, the x-z plane, the y-z plane, and/or the xyz volume. The sensor 600 or compartment 604 may be configured to tilt and/or rotate around any axis at different positions along the path. The compartment 604 may be configured to rotate within the open space inside the annulus and may be configured to be raised up and down in that region while the compartment is rotating, or the rotating may be initiated once the compartment 604 is at a desired height.

In an example, the sensor 600 or the compartment 604 may be configured to follow a certain path defined in relation to the eventual position of an object and/or the OUT. The movement may follow a single or multiple circular paths in the x-y plane. The sensor 600 or the compartment 604 may be paused to remain in a certain position along the path for a specified period of time. In an example, the sensor 600 or the compartment 604 may remain still in a position while a measurement is or multiple measurements are performed. The sensor 600 or the compartment 604 may be moved, stopped and moved again any number of times as it follows the paths described herein. The movement may follow circular paths in the x-y plane while the sensor 600 or the compartment 604 are translated along the z-axis.

For example, the path followed by the sensor 600 or the compartment 604 may be described as following the surface of a cylinder. Other paths are contemplated such as lines, ovals, ellipsoids, squares, rectangles, concentric ovals, concentric ellipsoids, concentric squares, concentric rectangles, concentric cylinders, at least partially overlapping lines, ovals, ellipsoids, squares, rectangles, nearby lines, ovals, ellipsoids, squares, rectangles, and any combinations of these paths. Other paths contemplated may be described as passing through points on the two-dimensional surface of a three-dimensional object such as a cylinder, sphere, half sphere, box, cone, pyramid, diamond, prism (triangular, hexagonal), hollow cylinder and the line. Other paths may include multiple two-dimensional surfaces of three-dimensional objects that may or may not intersect, may or may not overlap, and may or may not be symmetric (e.g., concentric) with respect to one another. Other paths may include rotations of compartments or objects or volumes and the like.

In an example, the sensor 600 and/or the compartment 604 may return to certain positions along a path and pause while additional measurements are taken that may be compared with previous measurements taken at other times. While the sensor 600 includes the one compartment (e.g., the compartment 604), a sensor may have multiple compartments and each compartment may be configured to move independently as described above. The sensor 600 may be configured to follow a well-defined linear path relative to and object or the OUT, or to a separate volume or container substantially enclosing an object or the OUT. The inner surface of the sensor and/or the outer surface of the inner container may comprise structures such as guide rails or slots to ensure the motion remains substantially linear along a well-defined axis. The inner surface of the sensor and/or the inner and/or outer surface of the inner container may comprise materials such as conducting materials or materials with known electromagnetic properties that partially or wholly cover the surfaces. In embodiments, patterns, cut-outs, and the like of conducting or other materials may be used to calibrate and/or characterize the sensor and/or to determine calibration and/or positioning and/or object specific information and may be used to generate additional or corrective signals that may be used to model the sensor and/or improve system performance. In embodiments, the inside of the inner container 624 may comprise reflecting or absorbing materials or both and may comprise electromagnetic transmitters and/or receivers and/or transceivers, and/or anisotropic scatterers that may be used to generate calibration signals and/or characterization signals and/or signals and/or sensor model parameters that can be used in the reconstruction algorithm.

Figure 6B:
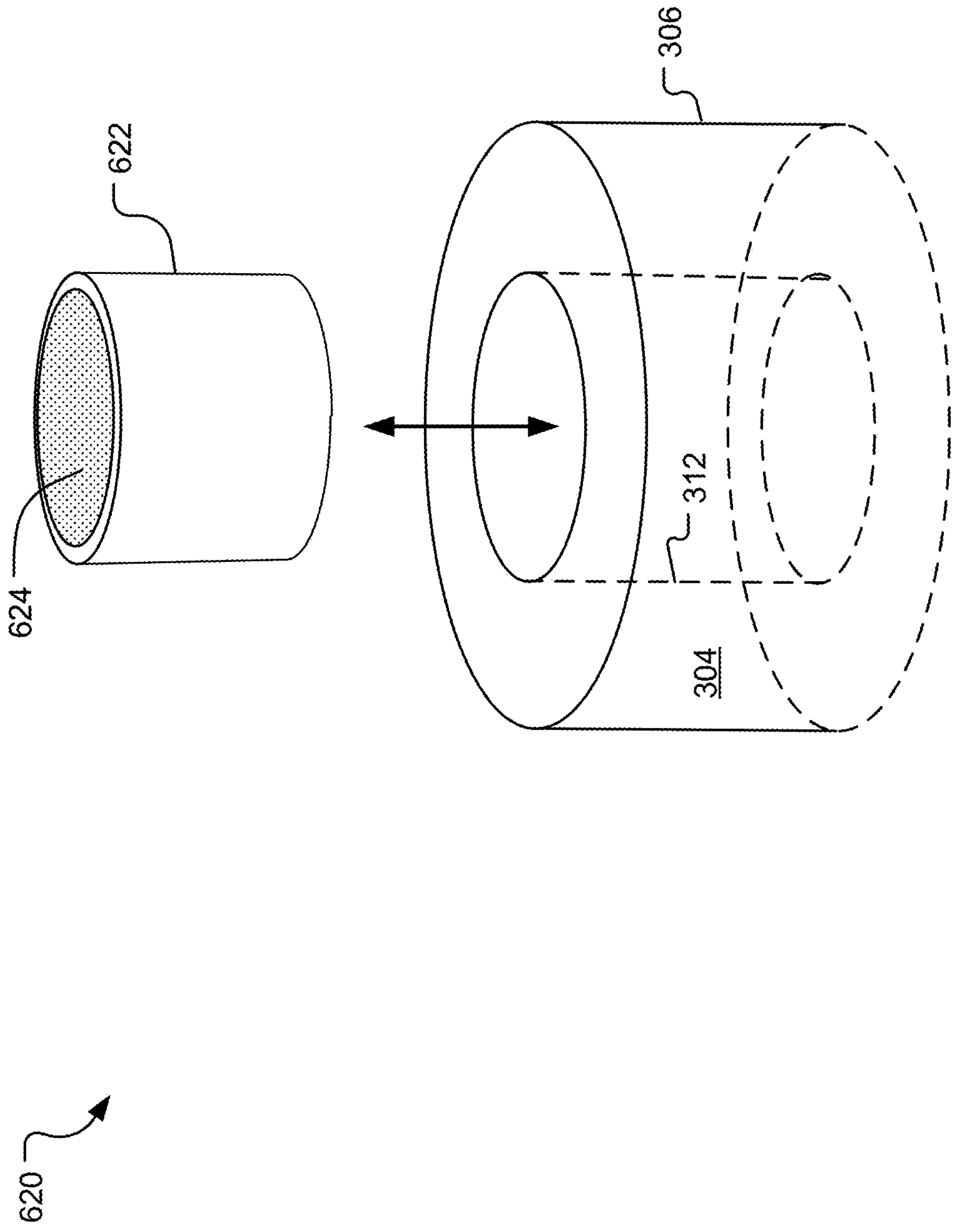
FIG. 6B is a perspective view of an example annular sensor in a dielectric tomography system with a coupling medium object domain insert.

Referring to FIG. 6B, a perspective view of an example annular sensor 620 with a coupling medium object chamber insert is shown. The annular sensor 620 includes the inner wall 312, the outer wall 306, and the coupling medium 304 as described for the sensor 300. The annular sensor 620 may also comprise top and bottom plates, 352*a*, 352*b* (not shown). An interrogation chamber insert 622, also referred to as an object chamber insert 622, and/or as an object domain is configured to fit within the inner wall 312. An object or an OUT may be placed within the insert 622, and the insert 622 with the object or OUT may be placed in the sensor 620. The insert 622 may be configured to contain a coupling medium 624 such as air, water, distilled water, oil, canola oil, glycerin, metal, alcohol, emulsion, plastic, patterned material, or combinations thereof, and the object or OUT may be placed in the coupling medium 624. In an example, an emulsion may be a stable emulsion, a permanent emulsion, a semi-permanent emulsion, and the like. The antennas 308*a*-308*h* (not shown in FIG. 6B) are configured to transmit/receive signals through the coupling medium 304, the inner wall 312, the insert 622, the OUT and any other media in the sensor. In an example, the interface between the inner wall 312 of the sensor 620 and the chamber insert 622 may be lined or lubricated with an electromagnetic impedance matching fluid or gel to improve electromagnetic coupling between the two containers, ensure smoother motion, and minimize wear and tear at this interface. The interface may contain self-lubricating mechanisms and structures. In an example, the interface between the inner wall 312 of the sensor 620 and the chamber insert 622 may be lined with conducting films, pastes, patches, patterned layers, and the like, and may be used to create calibration and/or characterization signals and/or informational signals and/or error signals related to the position (angular, height, etc.) or contents of the insert.

In an example, an insert 622, may be configured as an electromagnetic scattering device and/or as a known scattering device and may be used to calibrate and/or characterize the sensor before an object to be measured or an OUT is placed in the insert 622. The electromagnetic scattering device may be an extended object such as a cylinder or plane with electromagnetic features on its surface (such as a metallic cylinder with a hole of any shape and dimension, multiple holes of similar or different shapes and dimensions, and/or patterns of shapes of any size and dimension etched or cut into its surface). The features on the scattering device may be chosen to provide an asymmetry to the scattering device. Such an extended object may be moved relative to the transmit and receive antennas through a combination of rotations and/or translations. In an example, an insert 622 configured to contain an object or an OUT may also comprise areas with electromagnetic features to provide additional calibration and/or characterization and/or positional and/or identification information to the sensor.

In an example, the coupling medium 624 of the insert 622 may be any kind of coupling medium disclosed herein. In addition, the coupling medium may be a combination of coupling medium and may comprise sections of coupling medium. For example, coupling medium 624 may comprise a half cylinder of coupling medium 1 and a half cylinder of coupling medium 2. In one example, the half-cylinder may be the top and bottom halves of coupling medium 624. In another example, the half-cylinder may have a half-circle cross-sectional area over the height or a portion of the height of the insert 622. For calibration and characterization examples, the different coupling medium may be used to calibrate and/or characterize the sensor 300 at different relative offsets and/or at different relative rotational angles between the insert 622 and the sensor 310. Other combinations of coupling medium such as more than two types, and with other cross-sectional areas and/or volumes are anticipated. In an example, the coupling medium 624 may be a dielectric phantom and may be configured to mimic, in the microwave region of the spectrum, a portion of the human body. In another example, the phantom may include materials, objects, and the like, with dielectric properties that correlate with clinically relevant conditions such as cancer, strokes, concussions, early onset Alzheimer's disease, CTE, internal bleeding, deep contusions, bone density changes, degenerative diseases, and infections, to name a few conditions.

In an example, the insert 622 may comprise microwave antennas, transmitters, receivers and the like that may be configured as part of an electromagnetic scattering device. In another example, insert 622 may comprise regions that have been configured to behave substantially as perfect reflectors, perfect absorbers, 50-ohm loads, loads of any complex and/or real impedance and the like. In an example, insert 622 may be configured to provide signals that support the determination of the S-parameters of the sensor 620, with and without the electromagnetic scattering device, over a range of frequencies. In an example, insert 622 may comprise conducting material into which at least one slot has been cut. In examples where more than one slot has been cut, the slots may have different dimensions and may be distributed in a symmetric or non-symmetric arrangement on the insert 622.

In an example, the insert 622 may be made of materials and shaped in such a way so as to be able to be modeled using electromagnetic and/or reconstruction algorithms. For example, the known physical and electromagnetic properties of the sensor 620 and insert 622 may be modeled to predict the amplitudes and phases of received signals at receive antennas in the sensor 620. Predicted amplitudes and phases may be determined for different transmitting antennas, receive antennas, RF signal frequencies, and relative positions of the sensor 620 and insert 622. In an example, amplitudes and phases of received signals may be measured and compared to the predicted values. Differences between measured and predicted values may be used to determine and/or improve and/or calibrate and/or characterize an electromagnetic model of the sensor 620 and/or the error coefficients and/or correction coefficients for the transceivers and/or reflectometers. The calibrated and/or characterized model of the sensor 620 and/or the error coefficients and/or the correction coefficients for the transceivers and/or reflectometers may be used in a reconstruction algorithm.

In an example, the chamber insert 622 may include additional materials used to guide an object or OUT to a certain position and/or orientation within the chamber insert 622. For example, the chamber insert 622 may comprise materials that may be used to hold an object or OUT still within the coupling medium 624. The chamber insert 622 may include a hand hold, clamp, or handle type device configured to enable a patient to grip during imaging operations. In an example, the chamber insert 622 may further comprise one or more flexible membranes configured to conform at least partially to an object or OUT that will be placed and/or moved through the coupling medium 624 and/or sensor 620. For example, the volume may comprise a flexible membrane shaped like a glove into which a hand that will be imaged is placed. The glove may serve as a barrier between the skin on the hand and the coupling medium 624 in the chamber insert 622. The flexible membrane may be removable so that it can be changed between users. The flexible membrane may be separate from the chamber insert 622 and may be placed on the example hand when the hand is outside the imaging system. The gloved hand may then be inserted into the coupling medium 624.

Figure 7:
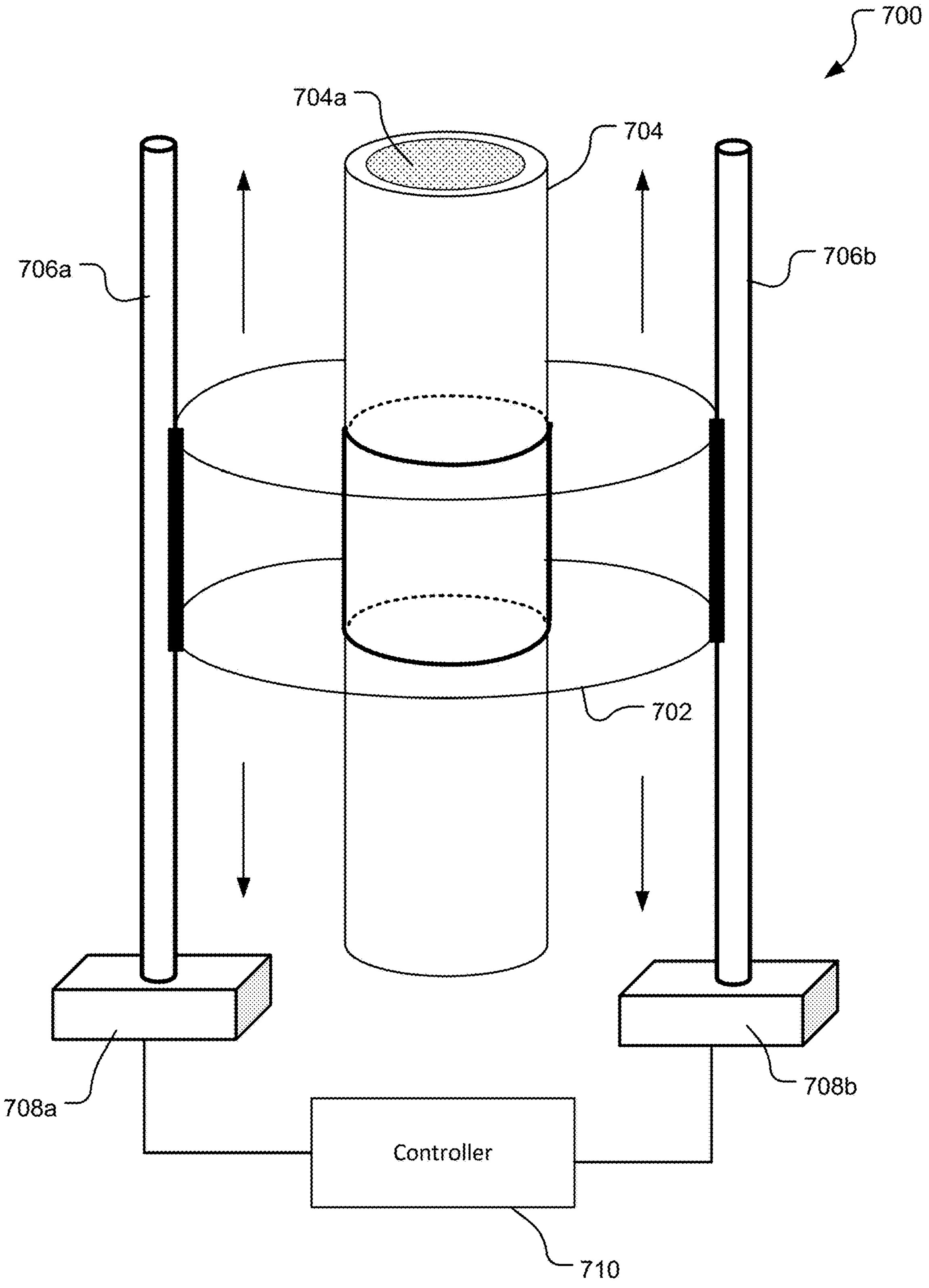
FIG. 7 is a perspective view of an example medical imaging system with a movable annular sensor.

Referring to FIG. 7 an example medical imaging system 700 with a moveable annular sensor is shown. The system 700 includes an annular sensor 702, such as the sensor 310, and an associated object chamber 704 which may also be referred to as the object domain. The annular sensor 702 includes one or more antennas 308*a*-308*h* (not shown in FIG. 7). The sensor 702 is mechanically coupled to one or more motion devices 706*a*, 706*b*, 708*a*, 708*b* configured to move the sensor 702 along the length of the object chamber 704 and/or rotate the sensor 702 around the object chamber 704. In an example, the object chamber 704 may include a coupling medium 704*a*. In an example, the one or more motion devices 706*a*, 706*b*, 708*a*, 708*b* may comprise rods, runs, slats, shafts, gears, screws, rotation mechanisms and the like that may be used to guide as well as move the sensor 702 along and/or around the object chamber 704 compartment comprising at least one coupling medium. In an example, the one or more motion devices 706*a*, 706*b*, 708*a*, 708*b* may comprise pulleys, belts, ropes, slides, motors, stepper motors, gears, gear boxes, plantary gear systems, bearings, ball bearings, cams, claws, cogs, collars, cylinders, feeds, gaskets, gears, hydraulics, ratchets, regulators, stabilizers, teeth, rotation mechanisms, and the like to enable the types of movement of the sensor 702 described herein. In an example, the object chamber 704 may be mechanically coupled to one or more motion devices configured to raise and lower the object chamber 704 relative to the annular sensor 702 and/or to rotate the object chamber 704 relative to the annular chamber 702.

In an example, the one or more motion devices 706*a*, 706*b*, 708*a*, 708*b* may be mechanically coupled and/or configured to move the object chamber 704 and may be communicatively coupled to a controller 710. The controller 710 may be configured to activate the one or more motion devices 706*a*, 706*b*, 708*a*, 708*b* to realize the intended motion of the sensor 702 and/or it may be configured to activate one or more motion devices mechanically coupled to the object chamber 704. The controller 710 may communicate with the one or more motion devices 706*a*, 706*b*, 708*a*, 708*b* and/or or any motion devices mechanically coupled to the object chamber 704 via wired or wireless control signals. In an example, the one or more motion devices 706*a*, 706*b*, 708*a*, 708*b* and/or or any motion devices mechanically coupled to the object chamber 704 may be activated via manual operation. For example, the sensor 702 may be moved and rotated based on mechanical devices such as foot pedals, treadles, cranks, jacks, rotation stages, 1D, 2D and/or 3D motion stages, buttons, touch screens, remote controls, and the like. In an example, the motion of the sensor 702 may be controlled in real time and/or may be controlled according to at least one pre-loaded program. In an example, the object chamber 704 may be moved and rotated based on mechanical devices such as foot pedals, treadles, cranks, jacks, rotation stages, 1D, 2D and/or 3D motion stages, buttons, touch screens, remote controls, and the like. In an example, the motion of the object chamber 704 may be controlled in real time and/or may be controlled according to at least one pre-loaded program. Multiple pre-loaded programs may be available to a user of the sensor and may be associated with a certain OUT and/or object within the sensor and/or patient being imaged and/or body part being imaged and the like. In an example, both the sensor 702 and the object chamber 704 may be movable and may be moved as part of the operation of the sensor system.

The controller 710 may be configured to monitor the motion devices and control the one or more motion devices 706*a*, 706*b*, 708*a*, 708*b* and/or or any motion devices mechanically coupled to the object chamber 704 and/or the sensor 702 based at least in part on the health, number of uses, age, position, performance, and the like of some portion of the motion devices. The one or more motion devices 706*a*, 706*b*, 708*a*, 708*b* and/or or any motion devices mechanically coupled to the object chamber 704 and/or the sensor 702 may include sensors that may monitor the tension on belts, oil levels in motors, friction levels along slides and the like, counters that keep track of how often gears have turned, stepper motors have run, regulators have been enabled and the like. Components that monitor the motion devices may be part of the motion devices or they may be physically separated from the motion devices, such as industrial vision systems that may monitor the motion devices from some distance away. In an example, the motion devices and/or the positions of the object chamber 704 and/or the sensor chamber 702 may be monitored using positional tracking devices such as inside out devices and/or outside in devices. In embodiments, the one or more motion devices 706*a*, 706*b*, 708*a*, 708*b* and/or or any motion devices mechanically coupled to the object chamber 704 and/or the sensor 702 may be configured to send and receive signals to and/or from the controller 710 and/or a user interface operably coupled to the controller 710. In an example, the operation of sensor components may be altered and/or adapted based on signals received from components that monitor the motion devices. In an example, the sensor 702 may comprise more than compartment, such as the compartment 604, and more than one object chamber 704 and more than one coupling medium and some or all of these compartments may be communicatively coupled to motion devices and moved as described above. In embodiments, the one or more compartments may have shapes that are substantially cylindrical, circular, box-like, disk-like, annular, layered, diamond like, spherical, symmetrical, asymmetrical, and the like.

Figure 8A:
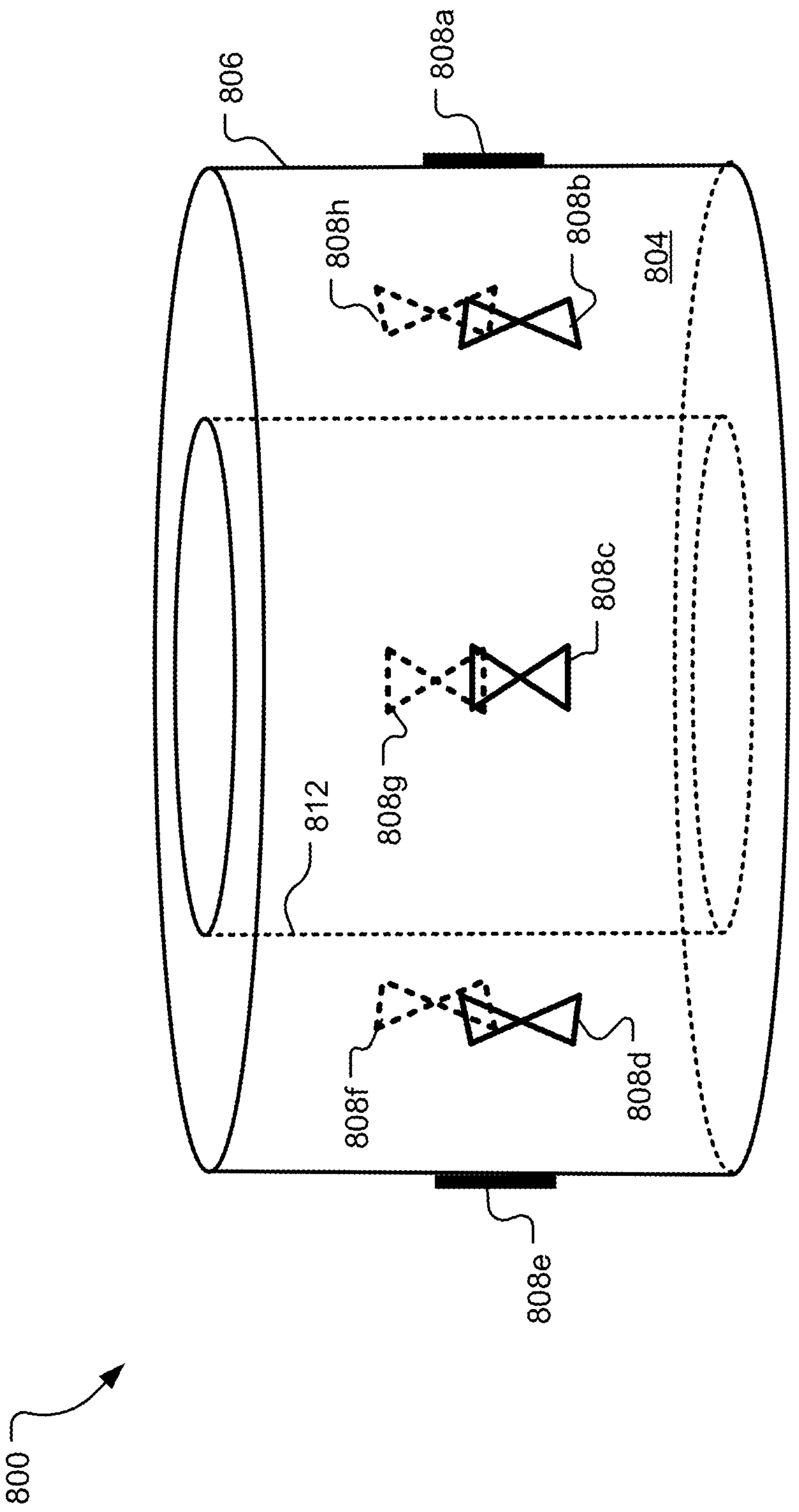
FIGS. 8A-8C are perspective view diagrams of example annular sensors for dielectric tomography systems with external and internal antenna configurations.
Figure 8B:
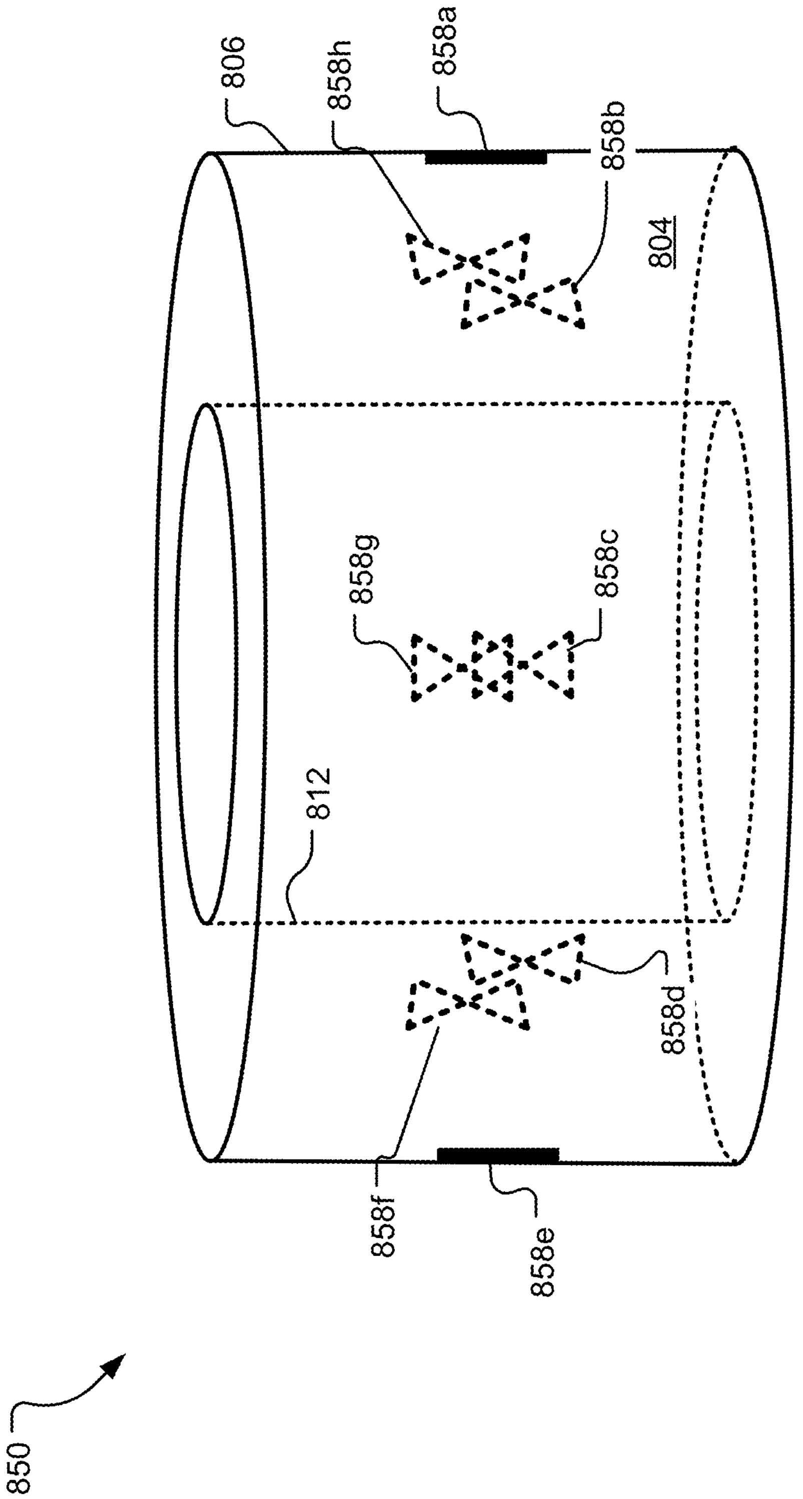
Figure 8C:
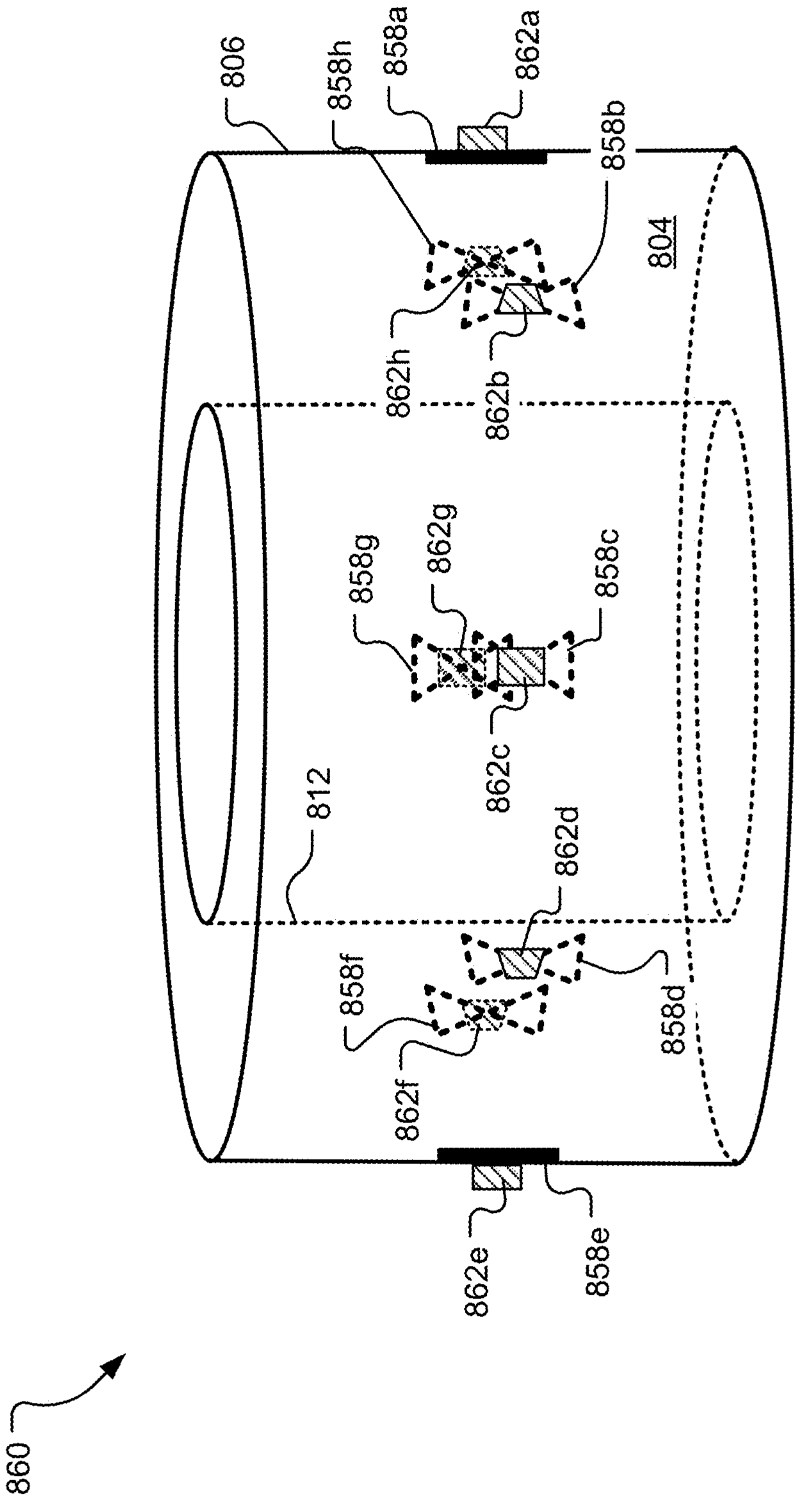

Referring to FIGS. 8A-8C, diagrams of example annular sensors for dielectric tomography systems with external and internal antenna configurations are shown. In general, the sensors for dielectric tomography described herein may comprise at least one microwave transmitter and/or receiver and/or transceiver. Microwave signals may be emitted by at least one microwave transmitter and/or transceiver and these signals may be scattered by objects within the sensor including within the object domain. The scattered signals may be received by at least one microwave receiver and/or transceiver. The microwave receiver or transceiver alone, and/or with at least some portion of a processor, may determine amplitude and/or phase, and/or frequency and/or timing information from the received signals. An object and/or an OUT may be placed within the sensor and/or within the object domain and may scatter microwave signals within the sensor. In an example, the at least one microwave transmitter may also receive scattered signals in the sensor.

In an example, referring to FIG. 8A, an annular shaped sensor 800 may include an outer surface 806 and an inner wall 812 and a coupling medium 804 disposed within the outer surface 806 and the inner wall 812. The sensor 800 includes at least one microwave transmitter and/or receiver and/or transceiver and corresponding antenna configurations, such as the antennas 808*a*-808*h*. In an example, one or more of the antennas 808*a*-808*h* may be substantially directional antennas and may be embedded and/or mounted to an external surface of the outer surface 806 of a sensor and/or compartment of a sensor. In an example, referring to FIG. 8B a sensor 850 includes one or more antennas 858*a*-858*h* disposed inside of the outer surface 806. For example, one or more antennas 858*a*-858*h* may be disposed on an inside surface of the outer surface 806 or in other locations which are closer to the inner wall 812.

The antennas 808*a*-808*h*, 858*a*-858*h* may substantially conform to the sides of a sensor and/or a compartment within a sensor. The antennas 808*a*-808*h*, 858*a*-858*h* may be cavity-backed and/or reflector-backed and/or folded, such as folded bowtie antennas, and arranged along the sides of the sensor and/or a compartment of the sensor to substantially emit microwave electromagnetic fields towards the center and/or an object and/or an OUT located within the sensor. In an example, the antennas 808*a*-808*h*, 858*a*-858*h* may be enclosed by regions that bump out from, or recess in from, the outer surface 806 of the sensor 800, 850 and/or compartments within a sensor. In an example, an outer surface of a sensor 806 may have cutouts to allow electromagnetic radiation transmitted and received by the antennas 808*a*-808*h*, 858*a*-858*h* to pass through the outer surface of the sensor 806.

In an example, referring to FIG. 8C, an example sensor 860 may include one or more microwave RF circuits 862*a*-862*h* configured as transmitters, receivers, and/or transceivers disposed proximate to the antennas 858*a*-858*h*. In an example, each antenna 858*a*-858*h* may include a respective RF circuit 862*a*-862*h*. The respective antenna-RF circuits may be an integrated assembly such that antenna and RF circuits are disposed in a single form factor. In an example, RF circuits may be included in a single housing configured with multiple transmit and/or receive ports coupled to more than one of the plurality of antennas 858*a*-858*h* via respective feedlines. At least one antenna structure may be coupled to an RF circuit via a conducting trace on a circuit board. One or more of the antennas 858*a*-858*h* may couple to a respective RF circuit 862*a*-862*h* via respective coaxial cables and/or microwave waveguides. In an example, at least some portion of a RF circuits 862*a*-862*h* may be disposed proximate (e.g., within 10 cm) of a respective antenna 858*a*-858*h*. In another example, at least some portion of a RF circuits 862*a*-862*h* may be disposed proximate (e.g., within the length and/or width and/or height and/or radius and/or diameter of the sensor 800) of a respective antenna 858*a*-858*h*. In an example, the walls of the sensor and/or sensor compartment may include gaps, cut-outs, slots, holes, cavities, hooks, latches, slots, snap connectors, mounting holes and components, and the like, to hold and/or affix and/or house some portion of a microwave transmitter and/or receiver and/or transceiver circuit relatively close to the antenna.

Figure 9A:
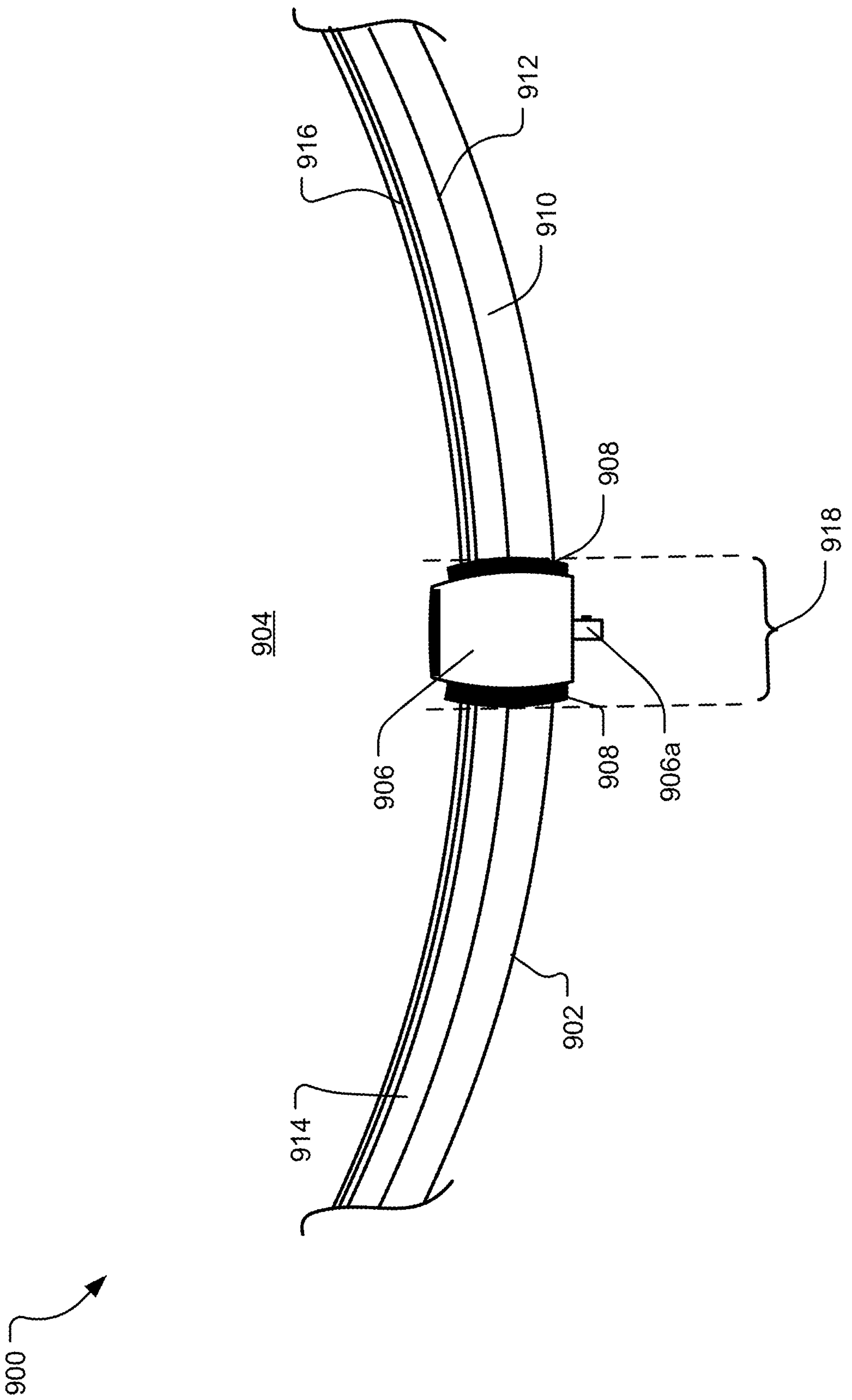
FIGS. 9A and 9B are top-down views of example internal and external antenna mounting configurations for a dielectric tomography sensor.
Figure 9B:
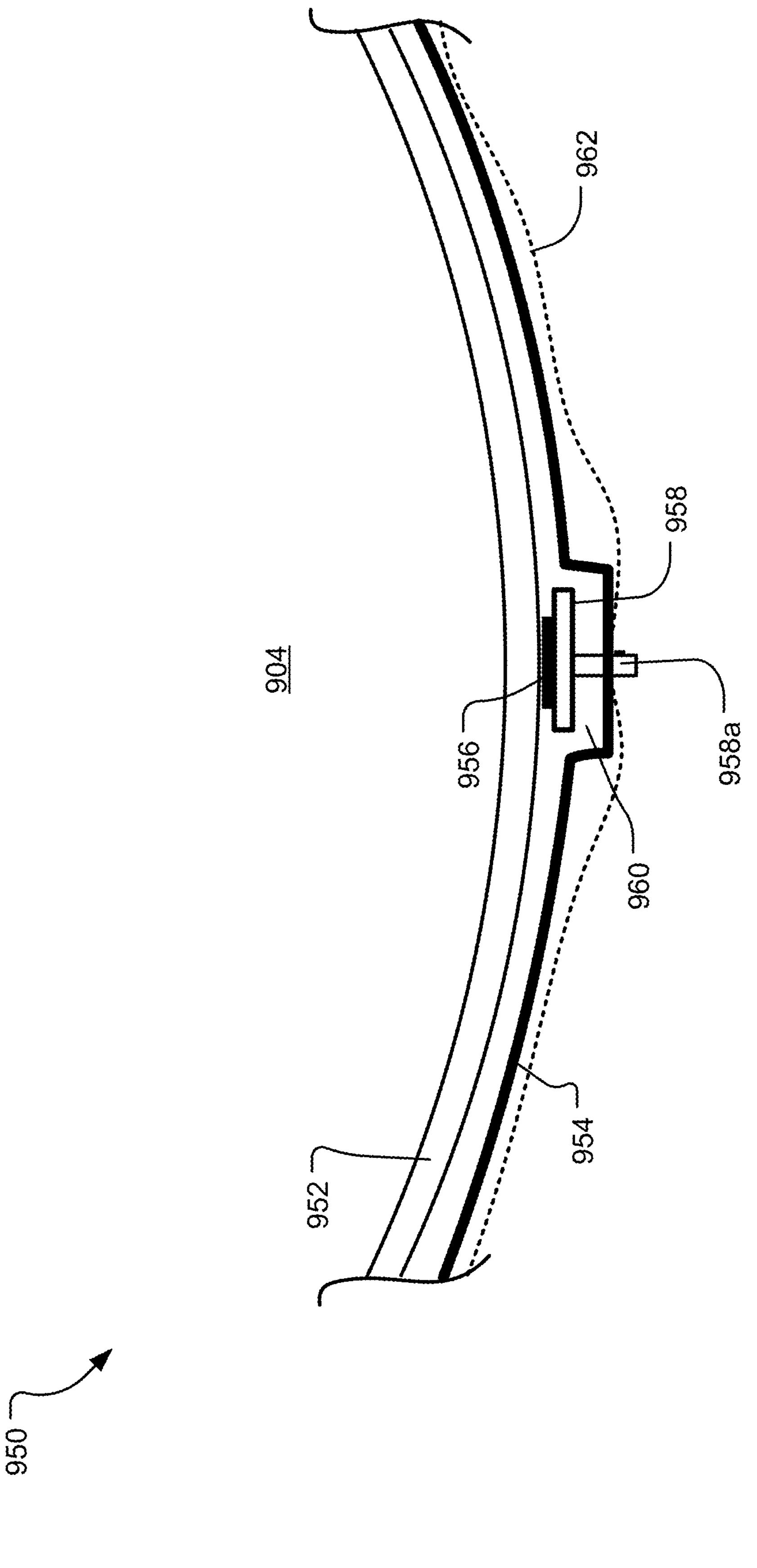

Referring to FIGS. 9A and 9B, examples of internal and external antenna mounting configurations for a dielectric tomography sensor are shown. Referring to FIG. 9A, a first example sensor 900 includes at least one sensor and/or compartment within a sensor with at least one slot, hole, cut-out, gap, cavity, and the like, to house the antennas and/or transceivers as described herein. The sensor 900 includes an outer wall 902 surrounding a coupling medium 904 such as previously described. At least a section of the outer wall 902 includes a cavity 918 with an antenna module 906 disposed within the cavity 918. The antenna module 906 may include an ultrawideband directional antenna directed into the coupling medium 904. In an example, a membrane or material may be disposed between the antenna module 906 and the coupling medium 904. The antenna module 906 may include a port 906*a* configured to couple to a feedline and/or to other control interfaces. In an example, the antenna module 906 may include internal RF circuitry and analog-to-digital components, and the port 906*a* may be configured to send and receive digital signals. The port 906*a* may be configured to send and receive analog signals and/or RF signals (e.g., RF feedlines). The components, or the outer wall 902 may further comprise additional layers 912, 916 arranged along the inner edge of the outer wall 902 configured to reduce or otherwise attenuate RF signals from entering or exiting the confines of the sensor 900. For example, the additional layers 912, 916 may be disposed such that RF absorbing dielectric materials 910, 914 may be disposed between the outer wall 902 and the coupling medium 904. In an example, the additional layers 912, 916 may comprise a laminate of resistive sheets configured to absorb, reflect, and/or attenuate microwave signals. In an example, the outer wall 902 may be a conductor and there may not be additional layers 912, 916 arranged along the inner edge of the outer wall. In another example, the outer wall 902 may be a conductor and an additional layer 912 and/or 916 may be part of a container that holds a coupling medium. The cavity 918 may include one or more sealing structures 908 such as gaskets, o-rings, caps, stoppers, grommets, flexible membranes, sealants, containers, and the like configured to prevent coupling medium flow into or out of the sensor 900 and keep materials from inside the sensor and/or sensor compartment and/or coupling medium from leaking out of the compartment.

Referring to FIG. 9B, a second example sensor 950 includes an outer wall 952 around a coupling medium 904. In general, the sensor 950 is an example of an externally mounted antenna, such as depicted in FIG. 8A, which may protrude out from a sensor outer wall, or the wall of a compartment. For example, an antenna element 956 and associated support structure 958 may be disposed proximate to the outside surface of the outer wall 952. In an example, the support structure 958 may include RF circuitry. The antenna element 956 (and corresponding RF circuitry) may be communicatively coupled to a port 958*a*. In an example, the antenna element 956 and the support structure 958 may be separated from a conducting layer 954 by a gap 960. The conducting layer 954 may be a continuous surface of conducting material and/or it may comprise multiple conducting layers, sheets, forms, and the like in electrical contact with each other. In an example, an antenna 956 may be mounted inside a conductive container and/or module with an opening to allow electromagnetic radiation to propagate to and from the antenna. The conducting walls of the container and/or module may contact the conducting outer wall of the sensor 954. In an example, the shape of the outer wall 956 may be described as having bump outs where the antenna containers and/or modules are mounted to the sensor 950. The gap 960 may be filled with material and/or the gap 960 may be substantially empty. An additional layer of RF absorbing material and/or at least one RF absorber structure 962 may surround the conducting layer 954. The RF absorber 962 may be configured to extend around some, most or all of the outside edge of the sensor 950. The sensor 950 may contain one or more of the structures described herein, such as anti-reflective outer surfaces, conductive top and bottom surfaces, adjustable apertures, and additional shielding structures, and may operate without an external coupling medium (other than air).

In an example, the outer surfaces of the sensors 900, 950 (or respective containers within the sensors) may comprise one or more RF absorbing structures. An example RF absorbing structure may be a multi-layer absorber or a Jaumann absorber. Other multi-layer absorbers and Jaumann absorbers may be used. An RF absorbing structure may comprise a plurality of electrically resistive sheets essentially in contact and/or offset from one another. At least one resistive sheet may be substantially parallel to an outer surface of a sensor or container. The surface closest to the sensor wall may be lined with or be made of metal or a good electrical conductor at the frequencies in the operating range of the transceivers. In an example, a layer of magnetic absorber may be part of an RF absorbing structure. Spaces between electrically resistive sheets may be filled with dielectric media, such as the same coupling medium used elsewhere in the compartment, or different coupling medium.

Figure 10:
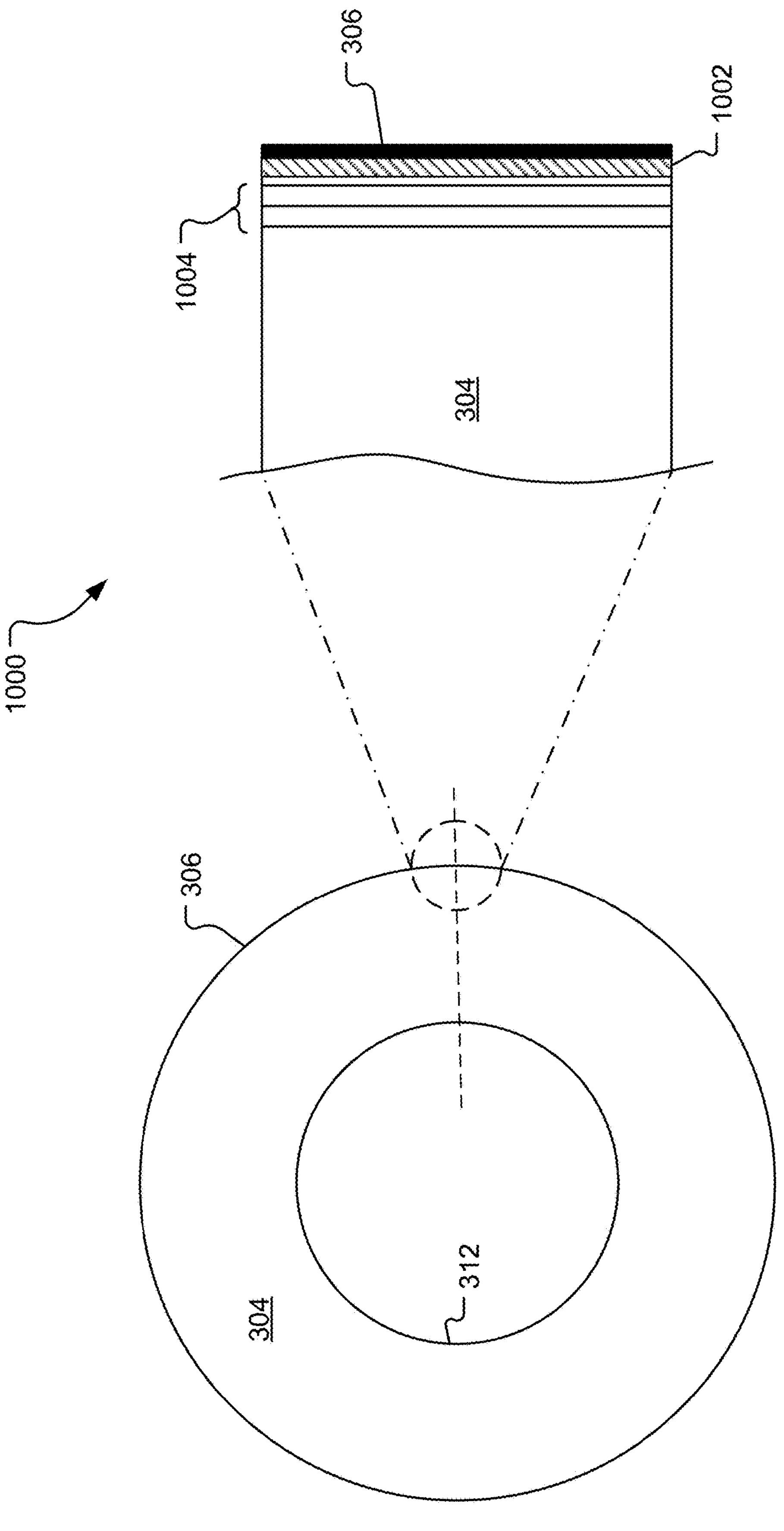
FIG. 10 is an expanded view of a chamber wall in an example annular sensor in a dielectric tomography system.

Referring to FIG. 10, a diagram 1000 of an expanded view of a chamber wall in an example dielectric tomography system sensor is shown. In an example, the outer wall 306 of the sensor 300 may be constructed with one or more RF absorbing structures. The one or more RF absorbing structures comprises at least one resistive sheet and/or film 1004. In an example, the inner edge of the outer wall 306 may comprise a conductive coating and/or a conducting layer and/or a conducting sheet 1002. The conducting layer and or sheet 1002 may be patterned to provide a conductivity value different from that of a solid sheet and/or coating of the conductor. The conducting layer or sheet 1002 may include slots, cut-outs, gaps, holes, and the like to allow electromagnetic fields from a microwave antenna (e.g., 808*a*-808*h*) into the sensor 300 (and/or a compartment/insert (604, 622) and/or the coupling medium 304). The resistive sheets or film 1004 may comprise carbon and/or carbon compounds, silicone, iron, polyurethane foam, nickel, nickel phosphors, NiP, laminates, metal flakes, and the like. In an example, the RF absorbing structure layers may comprise radar absorbing materials (RAM), resistive cards (R-Cards), high-impedance surfaces (HIS), frequency selective surfaces (FSS) and the like. There may be spaces or gaps between some of all the resistive sheets and/or conductor materials. In an example, the spacing between the sheets may be less than half of the longest wavelength microwave signal used in the sensor. In an example, RF absorbing structures may comprise at least one magnetic absorber such as graphene, Fe-graphene, graphene coated Fe nanocomposites, ferromagnetic nano-films, ferromagnetic metal nanoparticles, ferrites, cobalt-nickel alloys, metal flakes, and the like. The RF absorbing structures may comprise at least one RF absorbing material, including but not limited to ferrite tile absorber, Polyurethane Foam, including structured and/or shaped foams, polypropylene foam, and honeycomb materials. Other structures may also be used. In an example, referring to FIG. 9A, the RF absorbing structures may contain slots, gaps, holes, cutouts and/or cavities to allow for the insertion of antennas substantially radiating into the interior of the structure.

Figure 11:
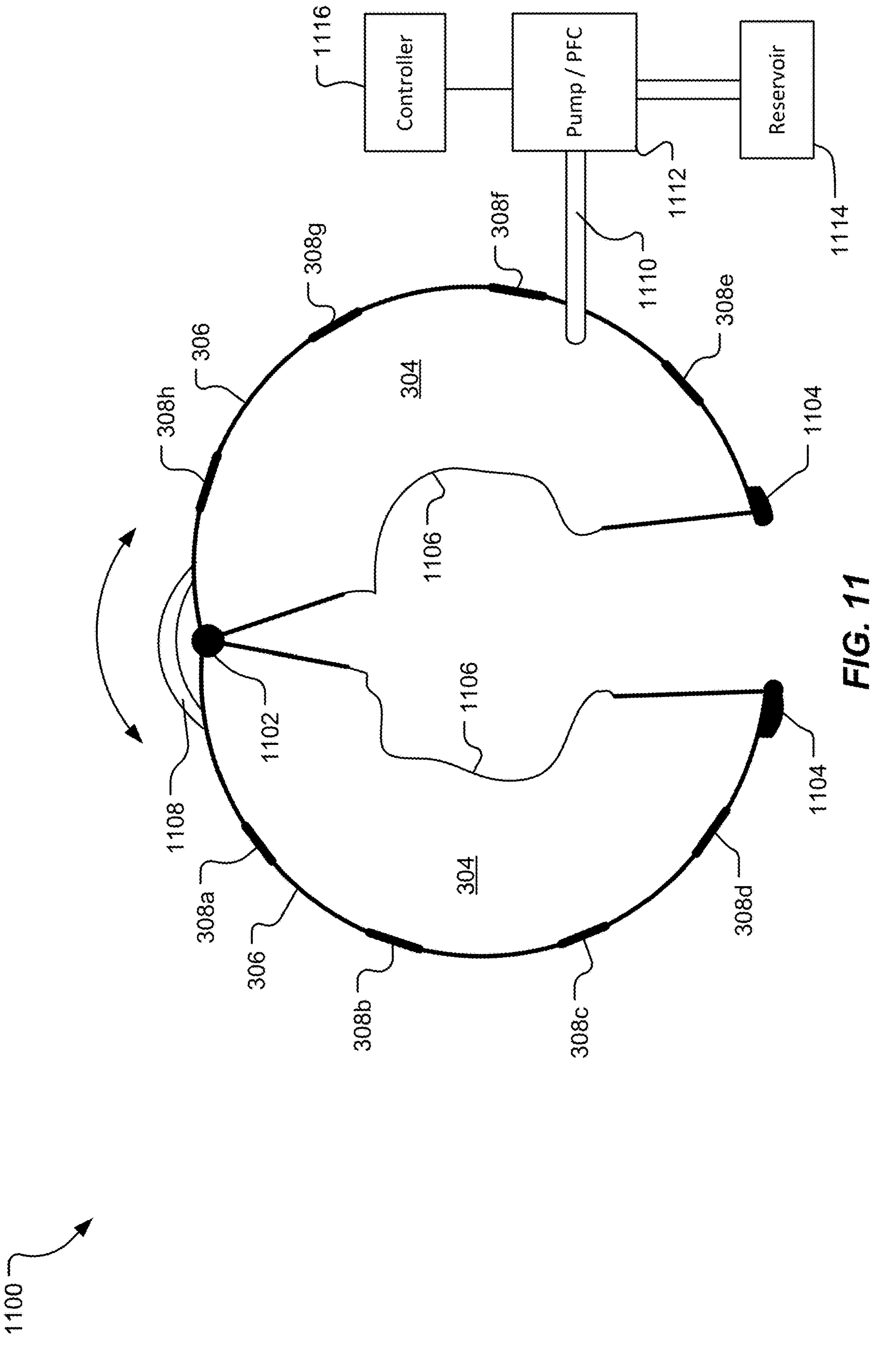
FIG. 11 is a top-down view of an example annular sensor with a pliable inner ring and a coupling medium pressure control system.

Referring to FIG. 11, a top-down view of an example annular sensor with a pliable inner ring and a coupling medium pressure control system is shown. In an embodiment, a sensor in a dielectric tomography system may comprise one or more movable components configured to enable the sensor to be disposed around an object to be inspected. For example, the sensor 1100 comprises at least one hinge 1102 and an attachment mechanism 1104 configured to enable the sensor 1100 and the coupling medium 304 to be separated into sections that may be placed around an object and/or an OUT. As an example, but not a limitation, the sensor 1100 may be shaped substantially like an annulus, and the annulus may be able to be split at some position and "opened up" into two complementary C-shaped or half-annulus parts, so that an object under test may be placed in what will be the center portion of the annulus once it is closed back up. The annulus may then be closed back up into its circular shape and may be fixed in the "closed" position using an attachment mechanism such as a latch, a button, a clip, a lock, a bolt, a hinge, and the like. A pliable inner wall 1106 may be configured to conform with the shape of the object and/or OUT to reduce the air gaps between the inner wall 1106 and the object. For example, the pliable inner wall 1106, and other components in the sensor 1100, may be configured to match the contour of the object and/or volume and/or compartment and/or OUT. The pliable inner wall 1106 may include plastics, foam, cushions, pillows, and the like, that may compress when the sensor parts are connected and may reduce gaps in coupling medium 304 from within the sensor. The pliable inner wall 1106 may comprise membranes and/or bags and/or films that may be at least partially inflated with air, gas, gel, liquid, emulsions, and the like to remove excess air and/or environmental gases and/or gaps from the space between the sensor parts and the volume and/or compartment and/or object and/or OUT. In an example, the pliable inner wall 1106 may be removable and/or replaceable and/or may withstand sanitation processes so that they may be changed between patients and/or procedures for example.

In an example, the sensor 1100 may be operationally coupled to a pressure control system configured to maintain an acceptable pressure and volume of coupling medium 304 within the sensor. One or more fluid transport devices 1110 may be coupled to the sensor 1100 and a pressure control module 1112 and configured to enable the flow of coupling medium 304 into and out of the sensor 300. The pressure control module 1112 may include pressure and/or flow control devices configured to maintain an acceptable pressure (e.g., 0.5, 1, 2, 3 psi, etc.) within the sensor 1100. A reservoir 1114 may be configured to store the coupling medium based on the size of the OUT and the corresponding displacement of the pliable inner wall 1106. A controller 1116 may be configured to control the pressure control module 1112. Various fluid distribution arrangements may be used. In an example, one or more cross-over connections 1108 may be configured to enable the pressure in each of parts of the sensor 1100 to equalize.

Figure 12:
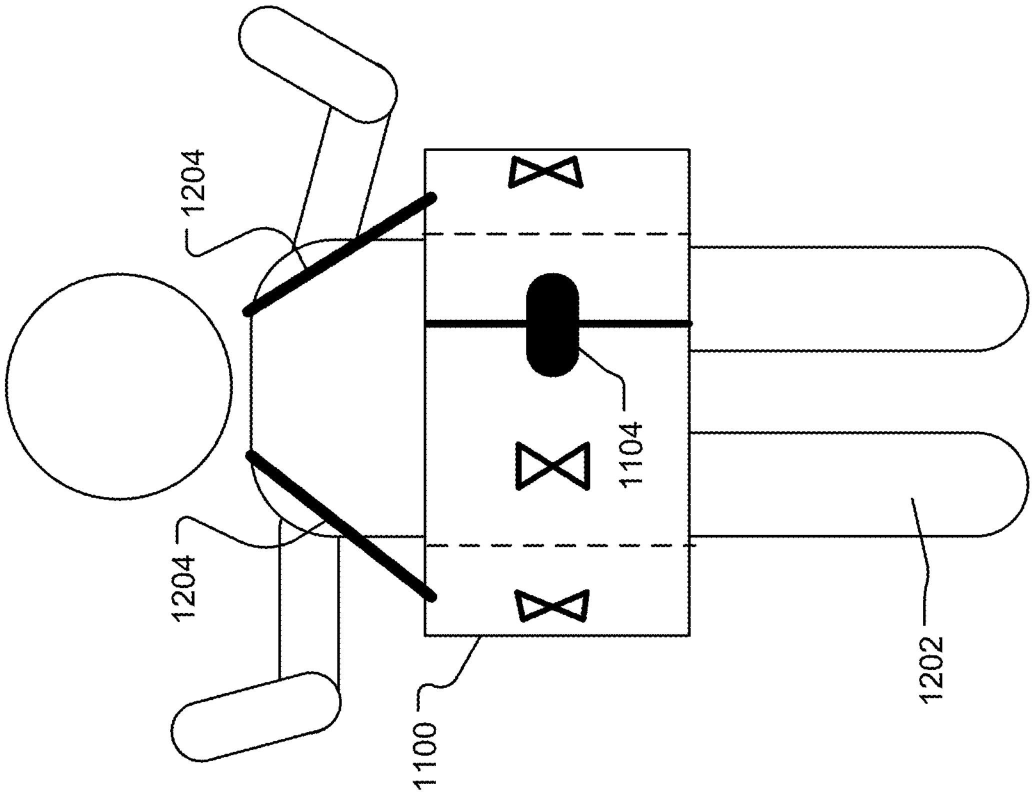
FIG. 12 is a diagram of an example use case for the annular dielectric tomography system of FIG. 11.

The at least two parts of the sensor 1100 (e.g., the C-shaped or half-annulus parts) may be flexible and/or may be held together by a flexible component and/or flexible attachment mechanism. Such flexible components may allow a sensor and/or sensor compartment to fit tightly around an object and/or OUT and/or a compartment or chamber comprising an OUT. The sensor 1100 may be configured to expand and contract while the sensor is operating. For example, referring to FIG. 12, the sensor 1100 (or a compartment 604) may be fitted around the chest and/or abdomen of a person 1202. In an example, one or more support components 1204 may be used to secure the sensor 1100 in the proper location of the person 1202. The pliable inner wall 1106 in the sensor 1100 (or a compartment in the sensor 1100) may enable the diameter of the inner ring of the annulus to expand and contract as the person 1202 is breathing. Similarly, a sensor and or sensor compartment may be fitted around an extremity of a person and the sensor and/or sensor compartment may expand and contract as the extremity is moved and or as blood pulses through the extremity. The controller 1116 may be configured to control one or more PFCs (pressure flow controllers) in the pressure control module 1112 to maintain acceptable pressure levels and the sensor 1100 (and the OUT) expand and contract.

While the sensor 1100 illustrates two C-shaped halves in a clam-shell configuration, other arrangements and sectioning may be used. For example, the C-shaped halves may be separate assemblies (e.g., not hinged), or additional sections may be used. For example, an annulus may comprise 4 quarter circle sections configured to surround a person. In an example, two quarter sections may be disposed on one side of person (e.g., in an arch configuration). Other sensor arrangements may also be used.

One of ordinary skill in the art will understand that features described in this disclosure relating to a particular sensor implementation may be applicable to other implementations. For example, a pressure control system as described above may be used to obtain and/or maintain a certain volume of coupling media is the sensors 300, 600, 620, 700, 800 and the like in this disclosure. Likewise, any of the sensors in this disclosure may comprise fittings to allow coupling media to be added to and/or removed from the sensor domain. In an example, a sensor domain may be filled with coupling media once and the coupling media may never be changed. In an example, coupling media may be "topped off" and/or added to if the volume is reduced by leakage and/or compositional changes. In an example, coupling media may be pushed into and/or pumped into the sensor domain and/or by being pulled into and/or 'sucked into' (such as with a vacuum pump and/or a syphon) a sensor domain through a tube, a valve, a plumbing fitting and the like.

Figure 13:
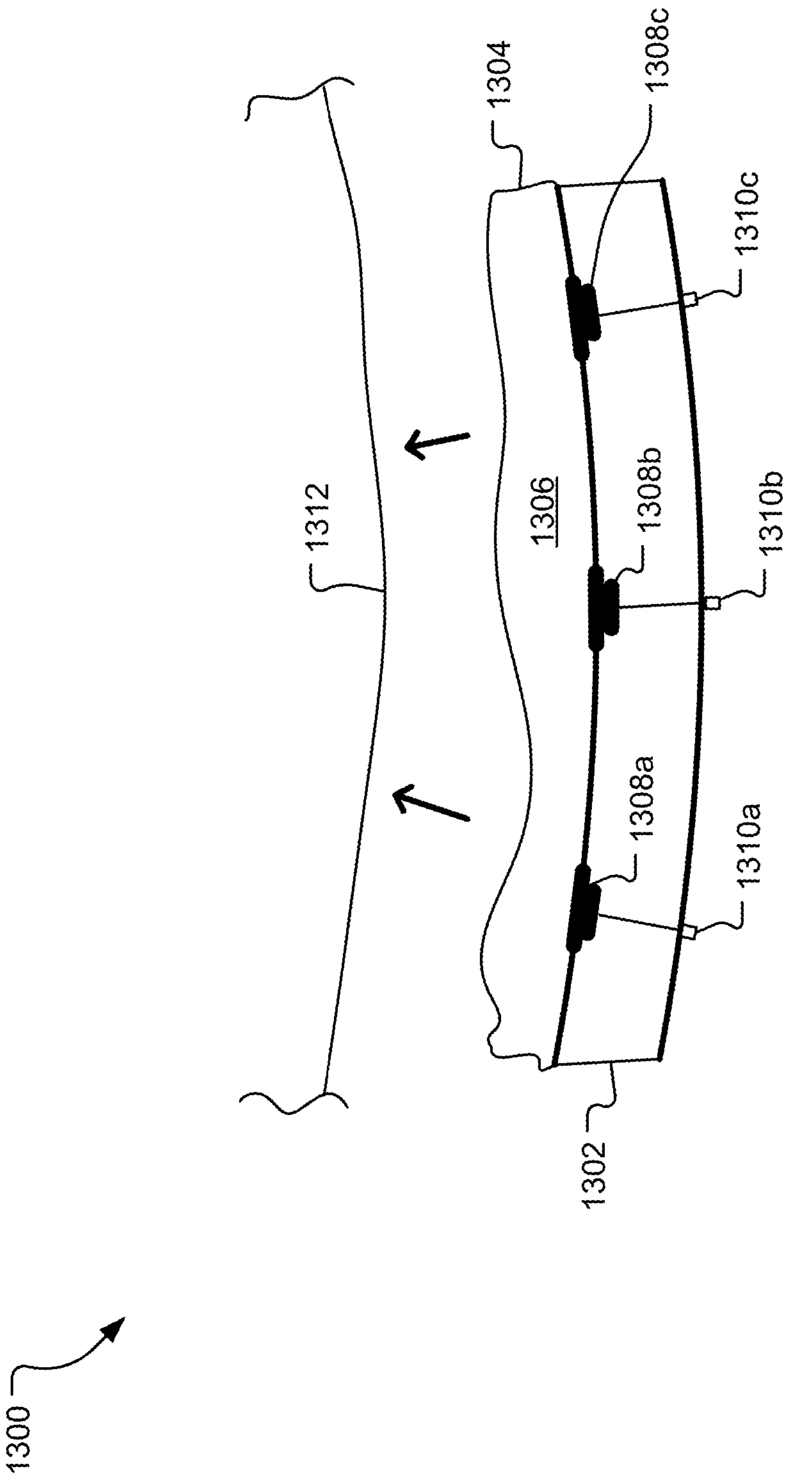
FIG. 13 is a side view of an example linear sensor configuration in a dielectric tomography system.

Referring to FIG. 13, a side view diagram of an example linear sensor configuration in a dielectric tomography system is shown. In an example, a linear sensor 1300 may include a rigid or semi-rigid housing 1302 with at least one or a plurality of antenna modules 1308*a*-1308*c* and respective ports 1310*a*-1310*c*. The antenna modules 1308*a*-1308*c* may include RF circuitry (e.g., transmitter, receiver and/or transceiver modules) within the housing 1302. The housing 1302 may be comprised of RF absorbing structures and/or materials such as graphene, Fe-graphene, graphene coated Fe nanocomposites, ferromagnetic nano-films, ferromagnetic metal nanoparticles, ferrites, cobalt-nickel alloys, metal flakes, ferrite tile absorbers, Polyurethane Foam, including structured and/or shaped foams, polypropylene foam, and honeycomb materials. The housing may be at least partially comprised of conducting materials. The antenna modules 1308*a*-1308*c* are disposed on a sensor side of the housing 1302 (e.g., as depicted in FIG. 13), and a flexible membrane 1304 is disposed over the sensor side of the housing 1302. A coupling medium 1306 may be disposed between the housing 1302 and the membrane 1304. In operation, the linear sensor 1300 may be placed against a surface of an area 1312 to be examined, such as the torso of a patient. The membrane 1304 is configured to conform to the area 1312 and reduce the potential for airgaps between the sensor 1300 and the area 1312. In an example, a coupling fluid pressure controller (such as described in FIG. 11) may be used to vary the volume and/or pressure of the coupling medium 1306.

The linear sensor 1300 is an example and not a limitation. In an example, a sensor or sensor compartment as disclosed herein may be substantially rectangular and/or planar. The antennas and/or transmitters may direct microwave electromagnetic fields in substantially one direction. Multiple antennas and/or transmitters and corresponding phase shifters (e.g., Butler matrix) may be configured to steer a beam of microwave radiation. The beam steering may be used to select a certain object and/or OUT and/or region of an out from which to collect scattered signals. In an example, the electromagnetic fields are generated by one or more antennas that are not in phase coordination with each other.

In an example, a linear sensor 1300 may be calibrated and/or characterized by being placed against a metal surface. The metal surface may include holes, gaps, cutouts, patterns, features and the like and may be a scattering device. The position of the linear sensor 1300 and/or the metal surface may be determined and/or tracked and/or sensed and/or monitored using positional tracking systems and devices such as inside-out and outside-in trackers. In another example, a linear sensor may reside in a full or partial enclosure that includes a handle and/or grip so that an object under test may be scanned in a manner similar to known handheld scanners and wands.

In an example, a sensor and/or sensor compartment may be arranged to serve as a platform upon which an object under test can be positioned. In use cases for the medical imaging of humans, the sensor and/or sensor compartment may serve as a desk and/or table on which a patient may rest their body or an arm, a hand, a foot, a leg, a head, and the like for imaging. The sensor and/or sensor compartment may be attached to a platform, desk, table, shelf, gurney, cot, bed, and the like. For example, the sensor and/or sensor compartment may be arranged as, and/or attached to, a cot, bed, recliner, couch, and the like. In an example, a sensor and/or sensor compartment may be arranged to be placed and/or moved in a region proximate to a platform upon which an object under test can be positioned. A sensor and/or sensor compartment may be placed under a platform and may be mechanically coupled to translation and/or rotation stages so that the sensor may be moved relative to the platform. In an example, a plate and/or sheet and/or blanket and/or covering designed to preferentially absorb and or reflect electromagnetic fields may be placed on top of the body or an arm, a hand, a foot, a leg, a head, and the like for imaging.

In an example, a sensor or sensor compartment may be arranged to fit into a wand or form factor configured as a hand-held instrument. A sensor or sensor compartment may be arranged to fit within a form factor configured to be attached to a patient by a belt, a bandage, a tourniquet, a wrap, a sticker, and the like. A sensor or sensor compartment may be configured to press against a deformable or conformable item that may be at least partially filled with at least one coupling medium and the deformable or conformable item configured to be placed against an object and/or OUT. A flexible membrane may be at least partially filled with at least one coupling medium and placed on a platform so that a patient may lie on the membrane like a mattress, mattress cover, waterbed, or the like. A sensor may be configured as a blanket, a weighted blanket, a plate, a dome, a box, an ellipsoid, and the like and may surround the object and/or OUT.

At least some portion of the coupling medium 1306 may be a liquid and/or foam and/or gel and/or emulsion and/or gas, and the sensor may comprise at least one device that may be used to fill and/or empty and/or remove some and/or add some and/or to circulate coupling medium to and/or within the sensor 1300. In an example, the sensor 1300 may include a pump or other pressure control module within the housing 1302 configured to move coupling medium 1306 from a storage reservoir into the sensor 1300, or from the sensor 1300 into a storage reservoir and to circulate some portion of the coupling medium within the sensor 1300. The pressure control module may be actuated manually, automatically, under computer control and/or in response to a threshold value set for the system. The pressure control module may be configured to circulate the coupling medium when its temperature exceeds a set range and/or when contaminants are detected. In an example, the pressure control module may be configured to add or remove the coupling medium 1306 from a reservoir if the height of the coupling medium or the volume of the coupling medium 1306 detected in the sensor 1300 falls below or rises above a threshold value. In an example, some or all the coupling medium 1306 may be pumped out and/or removed from and/or circulated within the sensor 1300 while an object and/or OUT are in the sensor. Some or all of the coupling medium 1306 may be pumped out and/or removed from and/or circulated within the sensor 1300 between object and/or OUT scans. In an example, some or all of the coupling medium 1306 may be pumped out and/or removed from and/or circulated within the sensor 1300 intermittently and/or on a schedule and/or after a certain number of scans and/or after a certain number of patients have been imaged and the like.

In an example, some or all the coupling medium 1306 may be pumped into and/or added to the sensor 1300 while an object and/or OUT are proximate to the sensor 1300. Some or all of the coupling medium 1306 may be pumped into and/or added to the sensor 1300 between object and/or OUT scans. Some or all of the coupling medium 1306 may be pumped into and/or added to the sensor 1300 intermittently and/or on a schedule and/or after a certain number of scans and/or after a certain number of patients have been imaged and the like.

The coupling medium 1306 may be altered when there is an object and/or OUT proximate to the sensor 1300. The coupling medium 1306 may be heated and/or cooled and/or run through a filter and/or run through a sterilization system and/or mixed with other media. The coupling medium 1306 may be altered when there is not an OUT in the sensor. The coupling medium 1306 may be heated and/or cooled and/or run through a filter and/or run through a sterilization system and/or mixed with other media. Alteration of the coupling medium 1306 may be done under the control of a feedback loop and/or may be done under the control of a feedforward loop. One or more parameters of the coupling medium 1306, such as its temperature, viscosity, dielectric constant, permittivity, conductivity, volume, height, weight, density, purity, and the like may be monitored, and the coupling medium altered based on at least one parameter's deviation from a threshold value. Monitoring and adjustment of a parameter may be achieved using a feedback loop. In an example, the adjustment of a parameter may be achieved using look-up tables and/or stored values as part of the system operation software. The monitored parameters may be reported to a user interface and a user may initiate and/or stop and/or otherwise regulate the alteration of the coupling medium.

Figure 14:
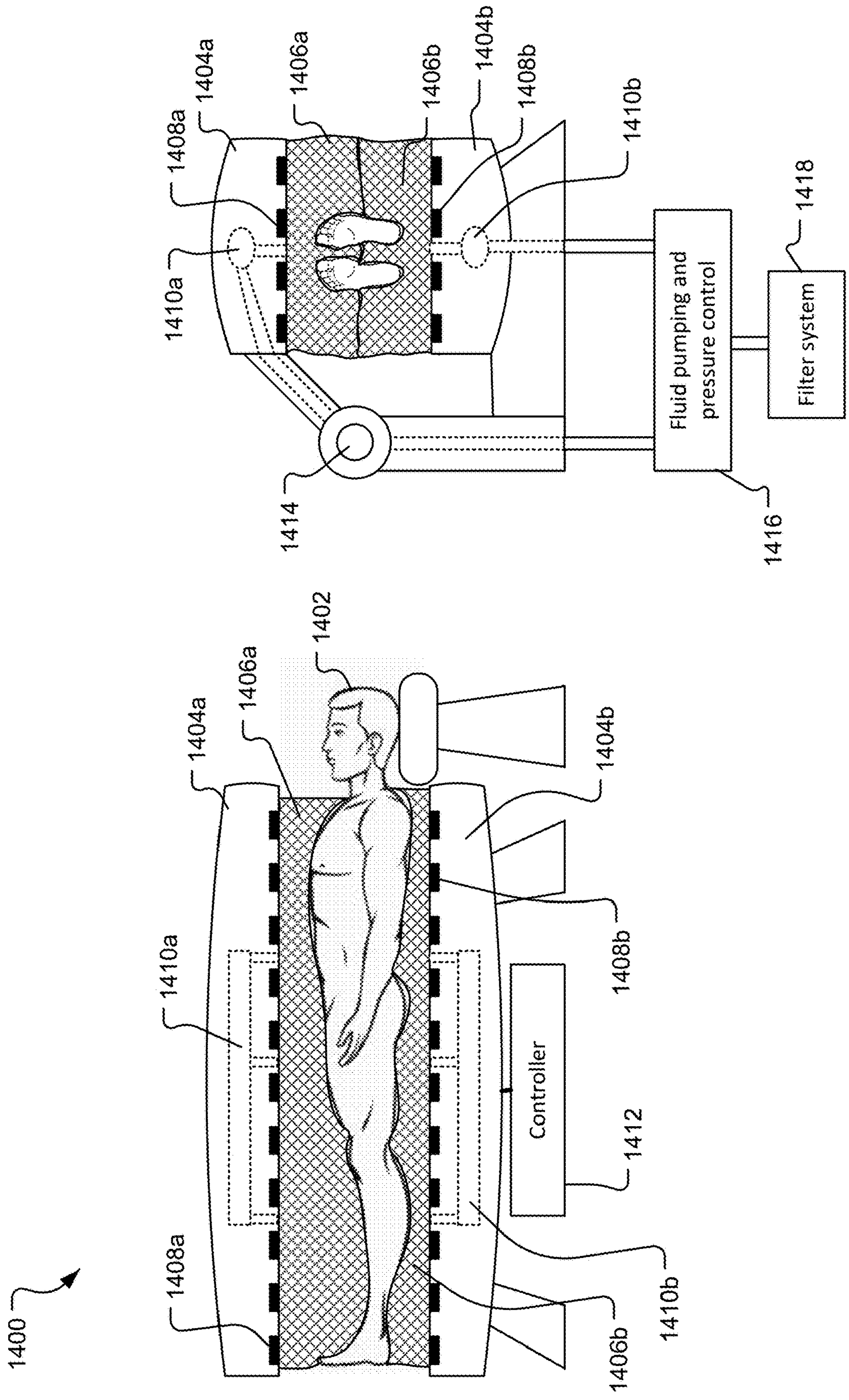
FIG. 14 includes side view diagrams of an example dielectric tomography system.

Referring to FIG. 14, an example dielectric tomography system 1400 is shown. The system 1400 is a clam shell type configuration with two sensor arrays configured to be disposed above and below a person 1402 or other object. The two sensor arrays may include the linear sensor 1300. The two sensor arrays may include an upper sensor array 1404*a* and a lower sensor array 1404*b*. The upper sensor array 1404*a* includes one or more antennas 1408*a* directed in a downward direction towards the person 1402. A coupling medium 1406*a*, including a flexible membrane, is disposed between the antennas 1408*a* and the person 1402. The lower sensor array 1404*b* includes one or more antennas 1408*b* directed in an upward direction towards the person 1402. A coupling medium 1406*b*, including a flexible membrane, is disposed between the antennas 1408*b* and the person 1402. The upper and lower sensor arrays 1404*a*, 1404*b* may be coupled to a hinge apparatus 1414 configured to enable the upper sensor array 1404*a* to lift and allow the person 1402 to enter an exit the system. The system 1400 may include a coupling medium distribution and control system including distribution piping 1410*a*, 1410*b* fluidly coupled to a fluid control module 1416 configured to regulate and control the pressure of the coupling medium 1406*a*, 1406*b* in the respective sensor arrays 1404*a*, 1404*b*. The fluid control module 1416 and a filter system 1418 may provide the control and filtering functions as describe for the sensor 1300 in FIG. 13. For example, the fluid control module 1416 and the filter system 1418 may be configured to filter the coupling medium 1406*a*, 1406*b* to remove impurities which may impact the sensitivities of the respective sensor arrays 1404*a*, 1404*b*. One or more controllers 1412 may be configured to receive RF and/or data signals from the antennas 1408*a*, 1408*b* and perform image processing based on the received signals. The controller 1412 may be communicatively coupled to the fluid control module 1416 and configured to control the coupling medium properties (e.g., volume, pressure, temperature, flow rate, etc.).

In operation, the system 1400 may be opened to accommodate the person 1402 and enable imaging over one or more portions of the person 1402. The coupling mediums 1406*a*, 1406*b* may be pressurized to reduce the air gaps between the person 1402 and the membrane. In an example, the coupling mediums 1406*a*, 1406*b* may be sectionalized and the distribution piping 1410*a*, 1410*b* may be configured to enable pressure control of the individual sections. The antennas 1406*a*, 1406*b* are configured to transmit and/or receive microwave signals to/from the person 1402 and/or to/from each other and/or to/from components within the sensor. The antennas 1406*a*, 1406*b* may be configured to move and/or change position and orientation relative to the person 1402 and/or to the other respective sensor array 1404*a*, 1404*b*. The controller 1412 is configured to activate the transmit and receive processes and perform the corresponding amplitude and phase measurements on the signals to generate the image information.

The controller 1412 may be configured to monitor a temperature and if the temperature exceeds a certain value, the system may issue an alert and/or report the monitored result to the system and/or to the user interface. The system 1400 may monitor one or more parameters of the coupling medium 1406*a*, 1406*b*, such as its volume and/or its height and/or its viscosity and/or its temperature and/or its density, and/or the presence of impurities in the media, and/or at least one dielectric property of the media and may issue an alert and/or report the monitored result to the system. The controller 1412 may be configured to monitor one or more parameters of the sensor arrays, such as the respective volumes and/or the volumes of the coupling medium 1406*a*, 1406*b* and may issue an alert and/or report the monitored result to the system. The one or more measured parameters may include a parameter of a material in the sensor arrays 1404*a*, 1404*b*. In an example, the one or more parameters may be a temperature of the coupling medium 1406*a*, 1406*b* and/or the environment in which the sensor arrays 1404*a*, 1404*b* and/or system 1400 reside. The one or more parameters may be a geometric parameter of the sensor arrays 1404*a*, 1404*b* and/or system 1400 such as the level of the coupling medium 1406*a*, 1406*b*. The one or more parameters may include a permittivity of a coupling medium and/or compartment, and/or the purity or impurity of a coupling medium in the sensor and/or system. The one or more parameters may be a concentration of a material or materials comprised by a coupling medium.

The one or more parameters may be actively monitored and/or they may be stored as parameter values in the system software and used in closed loop and/or open loop control systems to adjust the impedance of an impedance matching network. In general, a sensor and/or system may report measured and/or stored system parameter values to a system operator and/or a system controller, such as the controller 1412. The system may report certain parameters as being in range, on the edge of a range, out of range, surpassing a threshold, approaching a threshold and the like. The sensor and/or system performance may be impacted by the values of the measured and/or stored system parameters and the sensor and/or system may report these impacts to the operator or to a system controller. In an example, a sensor may contain auxiliary systems that characterize the electromagnetic properties of the coupling medium. Such auxiliary systems may collect additional data including the temperature and viscosity of the coupling medium, and the like. The sensor may evaluate the properties of the coupling medium at regular intervals and notify an operator if the coupling medium needs to be replaced or requires further attention. A sensor may contain a closed-loop system, such as the fluid control module 1416, that maintains the coupling medium 1406*a*, 1406*b* at a desired temperature. The closed-loop system may be configured to filter and sanitize the coupling medium. The condition of the coupling medium may be reported to an operator via a user interface.

Referring to FIG. 14, an example dielectric tomography system 1400 may include only the upper sensor array 1404*a* or a lower sensor array 1404*b* shown. The sensor array may include the linear sensor 1300. The sensor array 1404*a* or 1404*b* includes one or more antennas 1408*a* or 1408*b* directed in a downward or upwards direction towards the person 1402. A coupling medium 1406*a* or 1406*b*, including a flexible membrane, is disposed between the antennas 1408*a* or 1408*b* and the person 1402. In an example, the person 1402 may be lying on a conducting surface or a conducting surface attached to a deformable enclosure comprising coupling medium and the electromagnetic fields of the sensor may be transmitted and received by the upper sensor array 1404*a*. In another example, the person 1402 may be lying on s lower sensor array 1404*b* and a conducting surface or a conducting surface attached to a deformable enclosure comprising coupling medium may be placed on top of the person 1402.

Figure 15A:
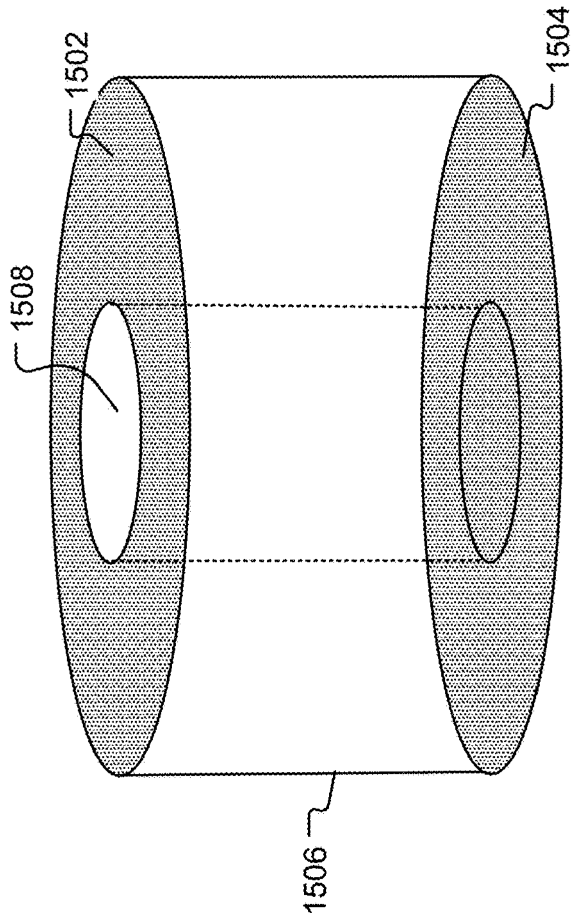
FIGS. 15A and 15B are example annular sensors with metallic top and bottom surfaces.
Figure 15B:
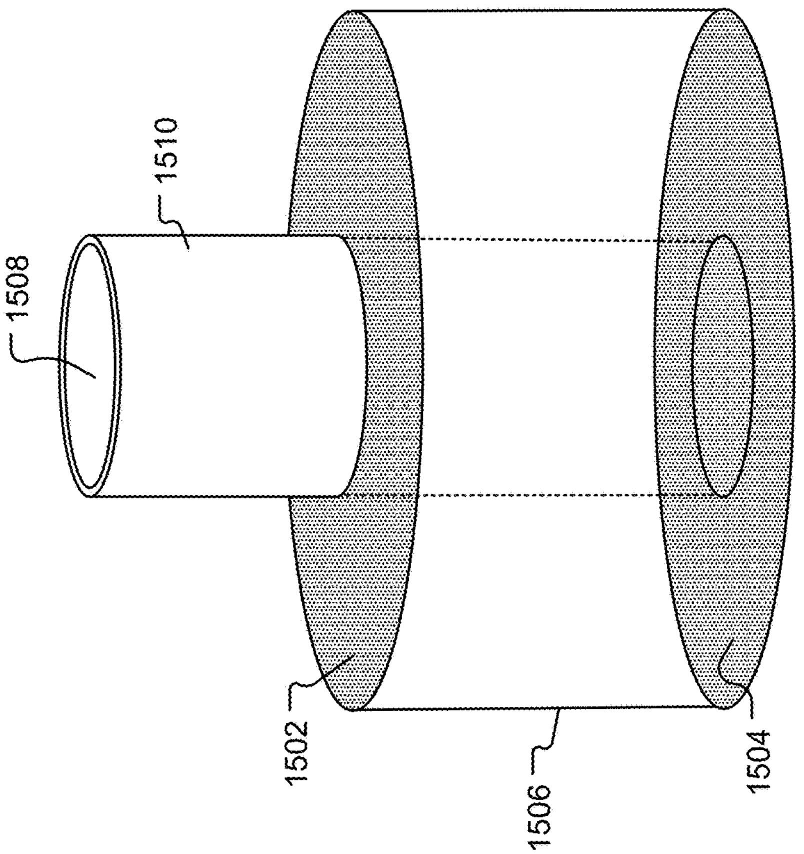

Referring to FIGS. 15A and 15B, example annular sensors with metallic top and bottom surfaces are shown. An example annular sensor 1506 may include a top surface 1502 and a bottom surface 1504 which are partially or fully covered by an electrical conductor such as copper, aluminum, platinum, tin, titanium, and the like. In an example, the top surface and bottom surface may be substantially flat and solid. In an example, the top surface 1502 may contain an array of holes, slits, and the like to allow for coupling medium to flow through when the sensor is assembled and/or when displaced by an object inserted into the coupling medium. In an example, the top surface 1502 may contain one or more holes allowing for the insertion of one or more electromagnetic scatterers used for sensor characterization. The arrays of holes, slits, and the like may be sized to substantially preserve the reflective electromagnetic properties of an electrically conducting surface at microwave frequencies.

The top surface 1502 and/or the bottom surface 1504 of the coupling medium may have openings allowing for the insertion of an object and/or an OUT. For example, the sensor 300 (or compartment 604) may include an opening 1508 in the top surface 1502 that may be substantially disk-like in shape and substantially centered on the respective face of the coupling medium and/or sensor and/or sensor compartment. The opening 1508 may be lined with and/or may comprise a form that is an electrical conductor or similar surface that behaves substantially like a reflector in the microwave frequency range. Examples of good electrical conductors may include metals, foils, films, transparent conductors, patterned surfaces, frequency-selective surfaces and the like. In an example, the electrical conductors reflect more than 25% of the microwave electromagnetic fields incident normal to their surface. In an example, an insert comprising an electrical conductor or similar surface that behaves substantially like a reflector in the microwave frequency range may be inserted into the opening 1508. Examples of good electrical conductors may include metals, foils, films, transparent conductors, patterned surfaces, frequency-selective surfaces and the like. In an example, the electrical conductors reflect more than 25% of the microwave electromagnetic fields incident normal to their surface.

In an example, the size of the opening 1508 may be adjusted through a system of aperture blades (not shown) (e.g., similar to the aperture of a camera lens). The aperture of such an opening may be automatically adjusted to closely match the outline of an object and/or an OUT. This automatic adjustment may be done, for example, by detecting mechanical resistance from insertion of an object and/or an OUT, via an auxiliary camera, or other means familiar to those skilled in the art. The top surface 1502 and/or the bottom surface 1504 of the sensor and/or sensor compartment and/or coupling medium may comprise substantially two-dimensional structures made of electrical conductors or of electromagnetically absorbing material. The top surface 1502 and/or bottom surface 1504 sensor and/or sensor compartment and/or coupling medium may comprise an extension structure 1510 configured to extend out vertically away from the top surface 1502 and/or from the bottom surface 1504. The extension structure 1510 may be configured to reduce the electromagnetic fields used in the imaging process close to the OUT, as well as shield the sensor and/or coupling medium from the interference of external electromagnetic signals.

In an example, a rigid, semi-rigid, and/or flexible insert may comprise coupling medium and an object and/or OUT. In embodiments, this insert may be placed in and/or moved through the sensor and/or the coupling medium while microwave signals are being transmitted and received. The insert may minimize the amount of coupling medium that must be replaced due to contact with objects and/or OUTs and/or contamination. This insert may be referred to as an object chamber and/or chamber insert and/or object domain, and the like. The insert may be cylindrical like a can with an open top and may be filled fully or partially with coupling medium. If a person's hand is the OUT, then a person may insert their hand into the insert and the insert may be placed inside the sensor. The insert may be moved within the sensor while data are being collected and/or the insert may be placed at various positions within the sensor and data collected. In embodiments, the insert may be rotated, tilted, translated and the like as described above. In another example, the sensor may be rotated, tilted, translated and the like as described above. The step size by which the insert and/or sensor is moved may be variable. For example, the insert and/or sensor may be moved by smaller increments when a certain portion of the object or OUT is in the same plane as the antennas and/or transceivers, or when the object or OUT is a certain distance away from the antennas and/or transceivers.

Figure 16:
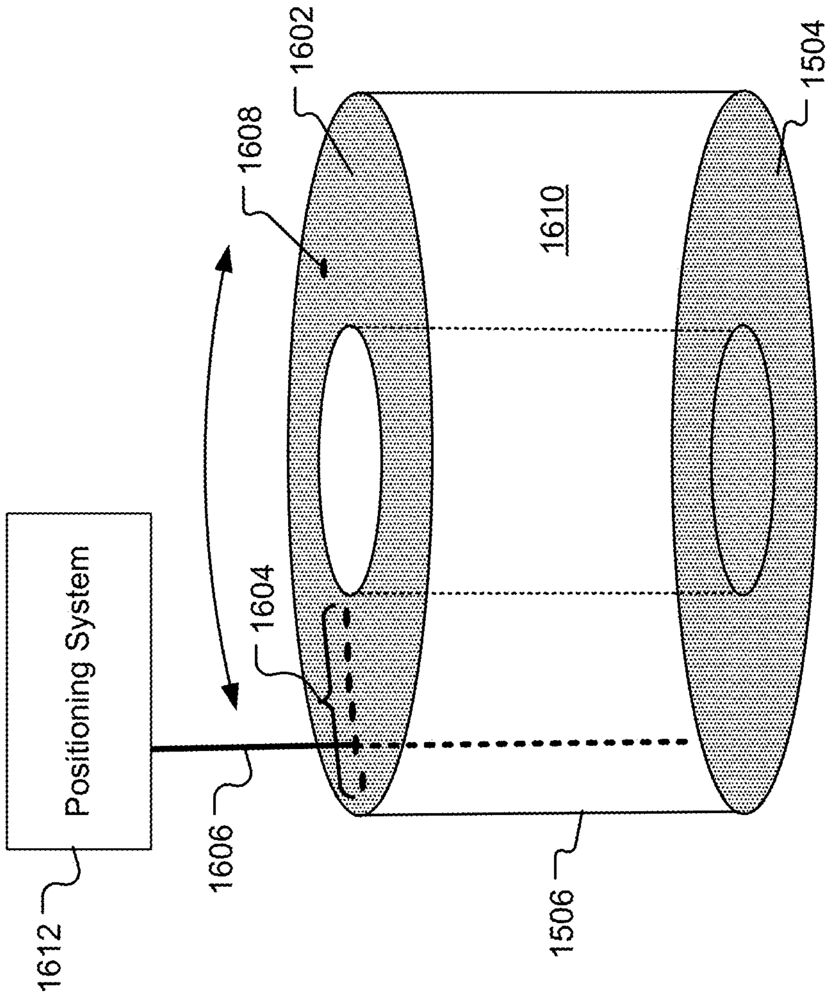
FIG. 16 is a perspective view of an annular sensor with a rotatable metallic cover and an example scattering device.

Referring to FIG. 16, an annular sensor 1506 with a rotatable metallic cover 1602 and an example scattering device 1606 is shown. The metallic cover 1602 may contain an array of holes 1608 (or slits and the like) to allow for coupling medium 1610 to flow through when displaced by an object inserted into the sensor. The metallic cover 1602 may contain one or more holes 1604 configured to enable the insertion of one or more scatterers 1606 used for sensor calibration and/or characterization (e.g., to characterize a container such as the annular sensor 1506). The arrays of holes, slits, and the like may be sized to substantially preserve the reflective electromagnetic properties of an electrically conducting surface at microwave frequencies. The metallic cover 1602 may be configured to rotate separate from the sensor and/or sensor compartment. In exemplary environments, the combination of moving a known scatterer up and down in the "z" direction, and around the sensor by rotating the top conductor, will allow the characterization scatterer to follow exemplary characterization paths.

The electromagnetic properties of the sensor 1506 may be characterized by inserting an electromagnetic scatterer 1606 with known electromagnetic characteristics (e.g., a piece of wire, a metallic cylinder with at least one conductivity discontinuity, cut-out, and/or slot) in the coupling medium 1610 in the region where an OUT will be characterized, or in the coupling medium 1610 between the transceiver antennas (not shown in FIG. 16) and the object domain. The electromagnetic scatterer 1606 may be substantially anisotropic. In an example, the electromagnetic scatterer 1606 may be translated and/or rotated within the volume of the sensor 1506 and the scattered microwave signals used to characterize and/or calibrate various aspects of the sensor. The electromagnetic scatterer 1606 may be referred to as a scatterer and/or as a scattering device, and/or as an object.

An electromagnetic scatterer 1606 with at least partially known electromagnetic properties and an at least partially known point-spread function may be placed within the sensing region of the sensor 1506 and/or coupling medium 1610. In an example, an electromagnetic scatterer may be configured on an insert, or as a cylindrical object that can be placed and/or moved and/or rotated within the opening 1508 of the sensor 1506. At a position and frequency of interest, the sensor 1506 may measure the amplitude and phase of scattered signals and/or parameters of the scattering matrix due to the interaction of the known scatterer with the microwave signals. The scatterer 1606 may be moved to a set of 1D, 2D and/or 3D positions inside the sensing region and/or in the region at the edge of the sensor and object domains. At each position and frequency of interest, the sensor 1506 may measure the amplitude and phase of scattered signals and/or parameters of the scattering matrix due to the interaction of the known scatterer with the microwave signals. Determining and processing the amplitude and phase of scattered signals and/or the scattering matrix for the known scatterer may yield calibration parameters and/or characterization parameters and/or parameters and/or sensor model parameters that may be used in the reconstruction algorithm. A cylindrical scattered, not shown, may be moved to a set of 1D, 2D and/or 3D positions inside the opening 1508. At each position and frequency of interest, the sensor 1506 may measure the amplitude and phase of scattered signals and/or parameters of the scattering matrix due to the interaction of the known scatterer with the microwave signals. Determining and processing the amplitude and phase of scattered signals and/or the scattering matrix for the known scatterer may yield calibration parameters and/or characterization parameters and/or parameters and/or sensor model parameters and/or error coefficients and/or correction coefficients that may be used in the reconstruction algorithm.

The sensor 1506 may measure parameters of the amplitude and phase of scattered signals and/or scattering matrix for field parameters substantially tangent to the surface enclosing the sensing region. Additional system parameters may be extracted by moving the scatterer to a set of 2D and/or 3D positions that may be described and/or visualized as being situated on virtual concentric surfaces. Additional system parameters may be extracted by moving more than one scatterer, individually and/or concurrently, to a single and/or a set of 1D, 2D, and/or 3D positions. More than one scatterer 1606 may be moved to positions that may be described and/or visualized as being situated on virtual concentric surfaces.

The scatterer 1606 may be referred to as an "object" in the imaging system. In embodiments, the scatterer may be a wire, a conducting trace, a conducting ribbon, a conductor, an object with a length that exceeds its cross-sectional diameter at its largest point, more than one wire, trace, ribbon, conductor, a wire and/or conducting trace formed into a shape, a cylinder with or without at least one end cap, an anisotropic form, and the like. The scatterer 1606 may be shaped to provide enhanced sensitivity for the detection of certain OUTs and/or permittivity values, and/or certain conductivity values, and/or certain shape or sized OUTs. In an example, the scatterer 1606 may be a passive scatterer.

The position of the at least one scatterer 1606 within the sensing region may be determined by positioning system 1612 including at least one of a motion encoder and/or camera system and/or RFID system and/or wireless locationing system and/or acoustic locationing system and/or an accelerometer, and/or positional tracking system, an inside out tracking system, an outside in tracking system, and the like. The position of the at least one scatterer 1606 may be determined by at least one position sensor, including but not limited to a resistance-based or potentiometric position sensor, an inductive position sensor, an eddy-current based position sensor, a capacitive position sensor, a magnetostrictive position sensor, a Hall Effect-based magnetic position sensor, a fiber-optic position sensor, an optical position sensor, an ultrasonic position sensor, a linear position sensor, a rotary position sensor, an angular position sensor, an inside out sensor, an outside in sensor, and any combination of these sensors, and the like.

The scatterer 1606 may be returned to certain positions in the set of scan positions and the amplitude and phase of scattered signals and/or scattering parameters remeasured to determine whether any system parameters have changed by more than some prescribed amount and/or threshold amount deemed acceptable by the system user and/or the system settings. Changes in the amplitude and phase of scattered signals and/or scattering parameters may be recorded and/or reported to a user via the user interface. In an example, based on variations in system values determined at repeated positions, and/or nearby repeated positions, a user may choose, and/or the system may automatically, restart a characterization and/or calibration process. A system may store at least one system value and/or set of system values from previous characterizations. These system values may be associated with at least a certain patient and/or body part and/or location, and/or temperature, and/or coupling medium and/or hardware set, and/or altitude, and the like.

The scatterer 1606 may be positioned by the positioning system 1612 including one or more structures such as a platform and/or an arm, and/or a gantry, and/or a holder that may be moved throughout the sensing region and/or the object domain, along at least a one-dimensional path. The positioning system 1612 may be capable of moving the scatterer 1606 along at least a two-dimensional path and/or at least a three-dimensional path. The structure may be capable of tilting, rotating, translating and the like. The structure may be attached to a motor and its motion may be controlled manually, automatically, via a user interface, in response to computer and/or voice actuated commands, via a script, via a program, by code running in some portion of the processor and the like.

In an example, the sensor 1506 may perform an auto-correction by fixing the scatterer 1606 at a single point, or by completely removing the scatterer from the sensor and/or coupling medium (e.g., to characterize and compensate for drift effects). The sensor 1506 and controller (not shown in FIG. 16) may be configured to perform an auto-correction by moving the scatterer 1606 along a substantially one-dimensional path (e.g., to correct for shifts in the dielectric properties of the coupling medium). The sensor 1506 may perform an auto-correction by moving the scatterer 1606 along a substantially two-dimensional surface (e.g., to characterize the incident fields generated by the transceiver antennas). The sensor 1506 may perform an auto-correction by moving the scatterer 1606 along the surface of or throughout the volume of a substantially three-dimensional volume, or along a series of two-dimensional surfaces (e.g., to further accounts for residual reflections inside the sensor, and other higher-order effects). The sensor 1506 may perform an auto-correction by rotating and/or translating the scatterer.

The electromagnetic characterization of the sensor 1506 may be realized with the assistance of a scatterer 1606 or set of scatterers whose shape substantially conform to the path followed during characterization. A characterization path may follow a Cartesian grid (1D, 2D, or 3D), and the scatterer 1606 may be of a substantially straight, elongated shape aligned with the axes of the grid. A characterization path may follow the surface of a circular cylinder, and the set of scatterers may consist of one or more substantially straight scatterers aligned with the z-axis of the cylindrical coordinate system as well as a set of curved scatterers whose curvature substantially matches that of the path or paths taken around the cylinder during characterization. In an example, the electromagnetic characterization of the sensor may be realized with sets of scatterers of different lengths, each length being associated with a particular frequency range. The scatterer 1606 may follow a path chosen to reduce or minimize the effect of drift (due to thermal effects and like) on the characterization. The scatterer 1606 may be periodically returned to one or more locations throughout the scan to correct for drift. In an example, other parts of a sensor enclosure (e.g., walls, bottom) may contain one or more openings or ports to allow for the insertion of one or more scatterers 1606 for characterization. The sensor 1506 may contain mounting points to allow for installation and alignment of an auxiliary fixture used to control the motion of the characterization scatterers.

In an example, the top surface (e.g., the metallic cover 1602) of the sensor may be made of metal (e.g., an electrical conductor at the applicable frequency range) that may freely rotate to facilitate the motion of a characterization scatterer 1606 or probe within the interior of the sensor 1506. The motion of the scatterer 1606 may be activated via a computer numerically controlled gantry or similar device. In embodiments, the top surface (e.g., the metallic cover 1602) may rotate due to ball bearings or rollers incorporated into the sensor 1506. In an example, the top surface (e.g., the metallic cover 1602) may freely rotate due to it floating on top of the coupling medium 1610. In another example, the metallic cover 1602 may be substantially solid and may be fixed and the motion of the scattered may be the rotation and/or translation of the scatterer 1606 within and/or at the edge of hole 1508.

In an example, referring to FIG. 6A, the antennas and RF sensors may be substantially held in a separate container than the one containing the OUT (the object chamber or the object container or the insert chamber or the insert), and the characterization scatterer 1606 may be configured to move within the container holding the sensors (the sensor container or the sensor chamber or the sensor domain). The object container may be replaced by one or more substitute containers with well-characterized electromagnetic properties while performing the characterization procedure. In an example, such an object container may be substantially filled with a dielectric medium. In an example, an object container may be substantially made of or covered in metal or another good conductor in the applicable frequency range. The object container may consist of metasurfaces or of an RF absorbing structure such as a Jaumann absorber. In an example, a linear sensor may perform an auto-correction with the aid of a known scatterer placed behind or on the patient's body. The sensor may perform an auto-correction by using a salient feature of the object to be imaged (e.g., a patient's ribs) as a point of reference.

Figure 17:
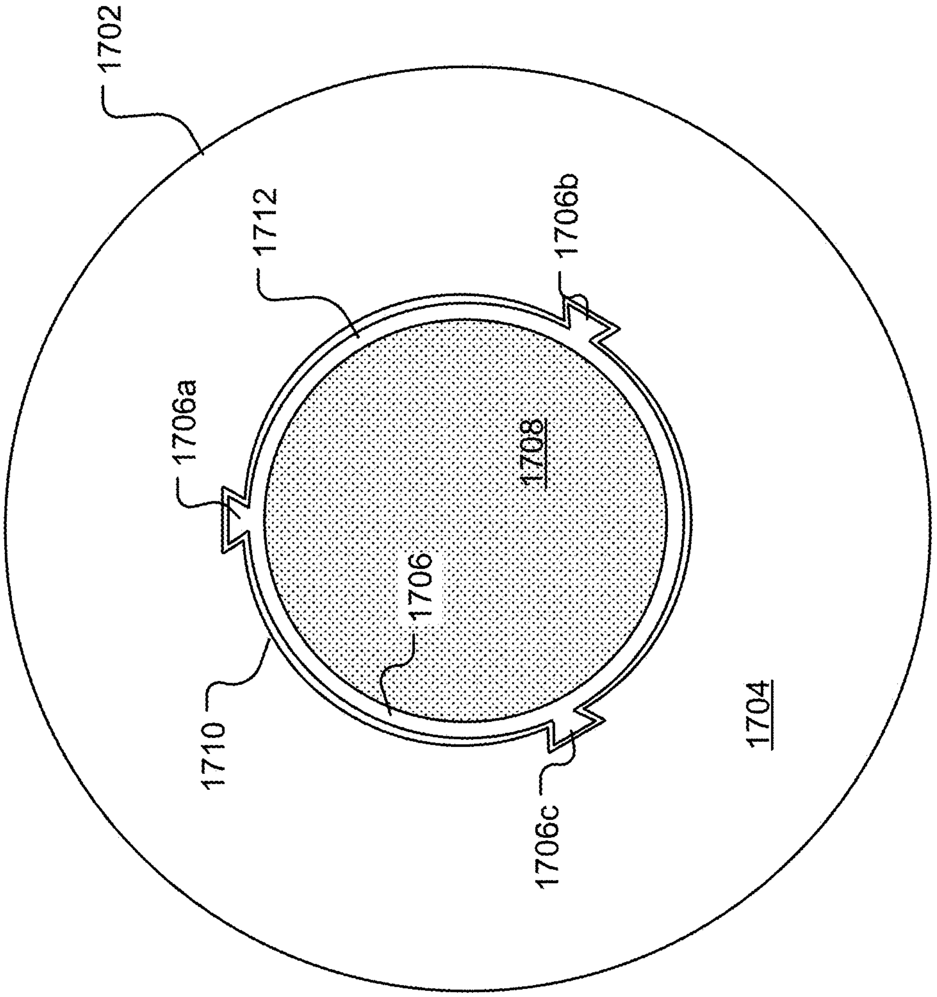
FIG. 17 is an example annular sensor with a guided and removable chamber representing the object domain.

Referring to FIG. 17, an example annular sensor 1702 with a guided and removable object container is shown. The sensor 1702 includes an insert 1706 that may be substantially hollow before being filled with some material such as a coupling medium 1708. The insert 1706 may be sized and shaped to allow the insertion of a certain object and/or object under test and may be configured to fit within an opening 1710 in the sensor 1702 (or a sensor compartment). The insert 1706 may be shaped with protrusions, tabs, guides, indents, such as the guides 1706*a*-1706*c* configured to enable the insert 1706 to move in and/or slide into the opening 1710 (i.e., the opening 1710 is configured with recesses to accommodate the guides 1706*a*-1706*c*). In an example, the surface of the insert 1706 may be substantially smooth.

In an example, the sensor 1702 may comprise at least one coupling medium 1704. The coupling medium 1704 may be the same and/or may be different that the at least one coupling medium 1708 of the insert 1706. In an example, a coupling medium 1712 may be disposed in the opening 1710 and along the guides 1706*a*-1706*c*. In an example, the coupling medium 1712 may be configured to be slippery and/or to reduce friction between the guides 1706*a*-1706*c* and the opening 1710.

Figure 18:
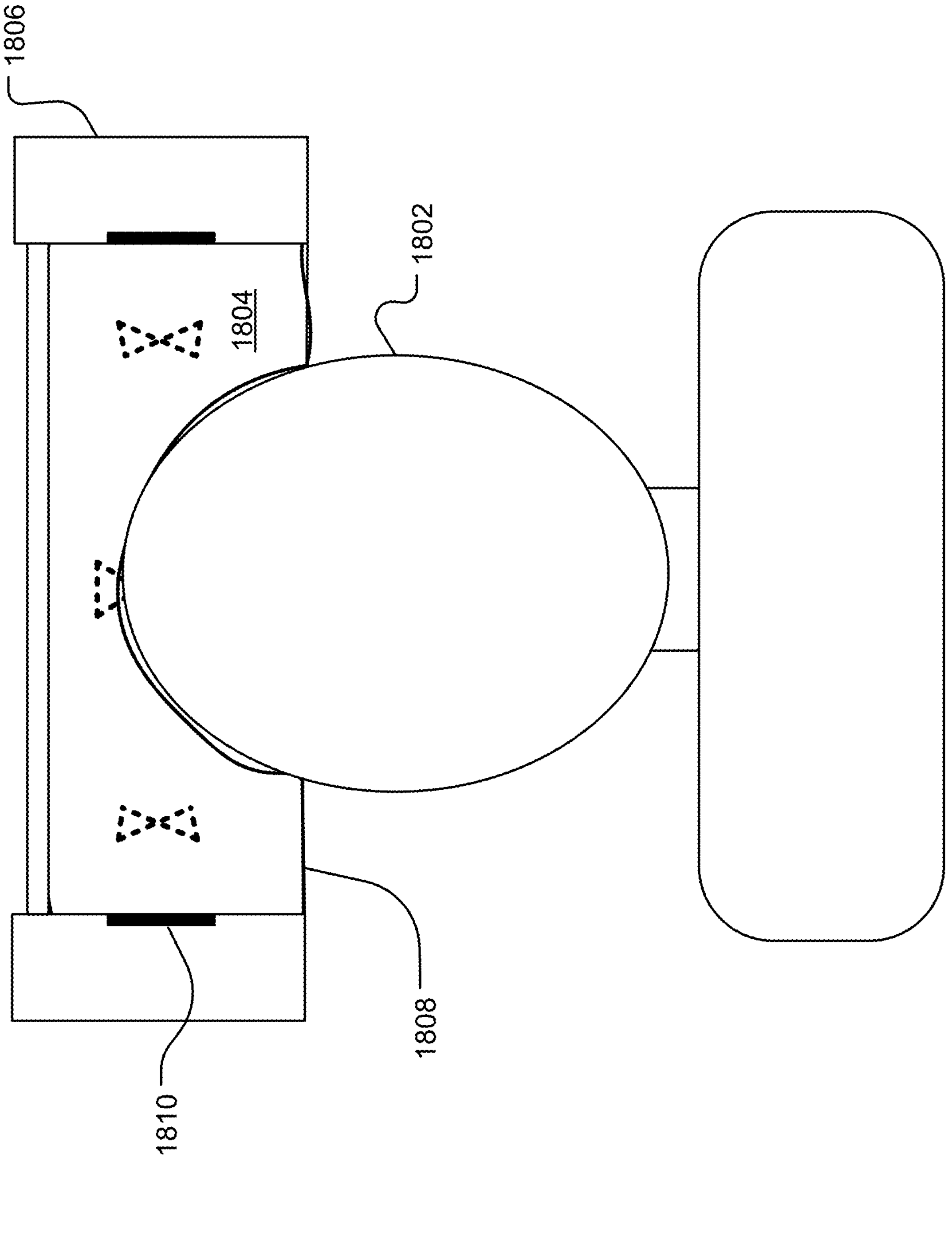
FIG. 18 is an example dielectric tomography sensor configured for use on a human head.

Referring to FIG. 18, an example dielectric tomography sensor 1806 configured for use on a human head 1802 is shown. The sensor 1806 is configured to accept at least a portion of a human head 1802 and obtain RF measurements based on one or more antennas 1810. A portion of the head 1802 may be held in place by a deformable membrane 1808 containing a coupling medium 1804 within the sensor 1806. In an example, such as described in FIG. 11, the coupling medium 1804 may be pumped in to or out from the area inside the deformable membrane so that the volume and/or compartment is a snug fit to the portion of the head 1802 (the fluid control module not shown in FIG. 18). In an example, the portion of the head 1802 may move through the sensor 1806, or the sensor may move while the head remains static. In an example, the sensor 1806 may be configured to detect changes in permittivity and conductivity of brain tissue that are associated with Alzheimer's disease. Detecting distinctions in the dielectric properties of grey and white brain matter based on RF signals between 10 MHz and 300 GHz may be used as a diagnostic method for detecting Alzheimer's disease. For example, at 2.4 GHz, the relative permittivity is 48.93 for grey matter in a healthy brain and 43.48 in a brain infected by Alzheimer's disease. Other frequencies and permittivity correlations may also be used to detect Alzheimer's by the dielectric tomography sensor 1806.

Figure 19:
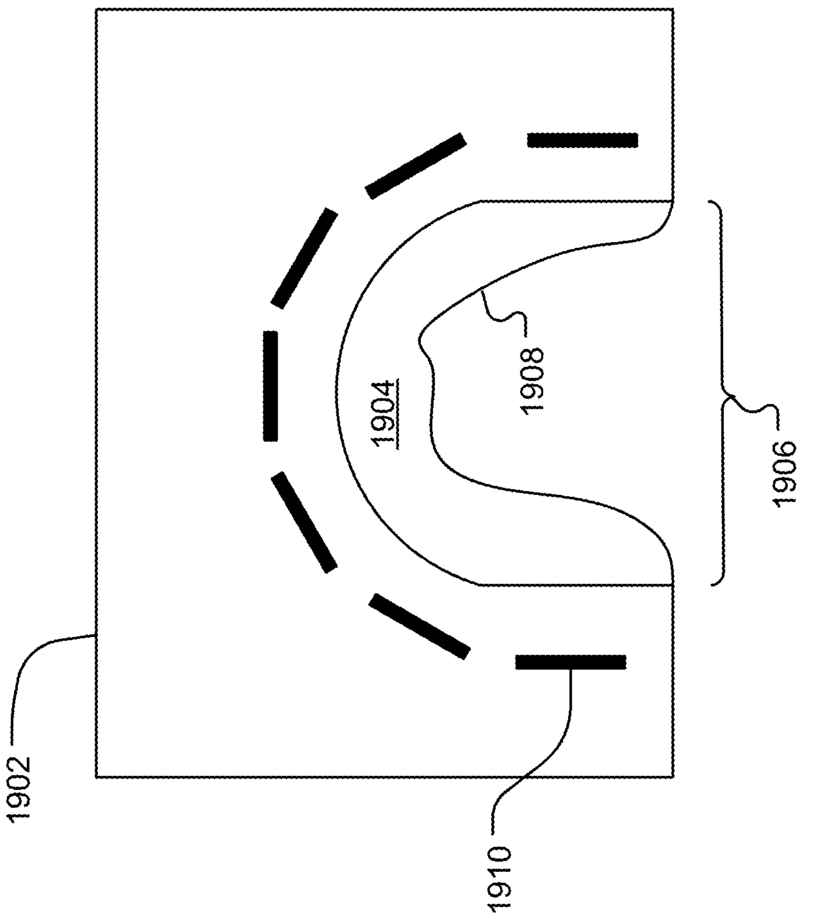
FIG. 19 is an example dielectric tomography sensor with an arched shaped object domain.

Referring to FIG. 19, an example dielectric tomography sensor 1902 with an arched shaped object chamber is shown. The sensor 1902 is configured to inspect an appendage such as an arm or a leg as an OUT which may be inserted into, or otherwise enclosed by, an opening 1906. The arch shape of the sensor 1902 is an example, and not a limitation, as other shapes such as an annulus, linear, elliptical, circular, etc. may be used to accommodate an OUT. In an example, a patient's forearm or leg may be inserted into the opening 1906. The sensor 1902 includes an array of antennas 1910 disposed around and/or in proximity to the opening 1906. A deformable (e.g., flexible) membrane 1908 may be disposed over the inside of the opening 1906 and configured to enclose a coupling medium 1904 between the antennas 1910 and the OUT. In an example, a pressure control module (not shown in FIG. 19) may be operationally coupled to the sensor 1902 and configured to control the volume, pressure and/or temperature of the coupling medium 1904 around the OUT. In an example, the sensor 1902 may comprise electromagnetic reflecting material and/or electromagnetic absorbing material and/or a combination of reflecting and absorbing material. The inside of the sensor 1902 may be shaped to preferentially reflect scattered signals to a certain position within in the sensor 1902.

In an example, the OUT (e.g., forearm) may move through the opening 1906 (e.g., when the sensor is stationary), or the sensor may be configured to move along the axis of the opening 1906 (e.g., when the OUT is stationary). Other relative movements between the sensor 1902 and the OUT, such as translations, rotations, tilts, and the like, may be used. In an example, the sensor 1902 may be moved manually, mechanically and/or automatically. The position of the OUT within the sensor 1902 and the coupling medium 1904 may be measured using a motion actuator, a camera system, a wireless positioning system, a machine vision system, a positioning and/or tracking system (e.g. inside-out, outside-in), and the like. The sensor 1902 may include electric, magnetic, electromagnetic, conducting, windowed, and the like materials configured for position and/or motion sensing.

In an example, the sensor 1902 may include addition materials configured to guide an object or OUT to a certain position and/or orientation within the opening 1906. The opening 1906 may comprise materials that may be used to hold an object or OUT still within the opening 1906. The sensor 1902 may include a gripping device, such as a circular ball, and a patient's hand may grip the ball while the hand is in the opening 1906. In an example, the membrane 1908 may be shaped like a glove into which a hand that will be imaged is placed. The glove may serve as a barrier between the skin on the hand and the coupling medium 1904. The flexible membrane 1908 may be removable so that it can be changed between users. The flexible membrane 1908 may be separate from the volume and may be placed on the example hand when the hand is outside the imaging system. The gloved hand may then be inserted into the volume.

Figure 20:
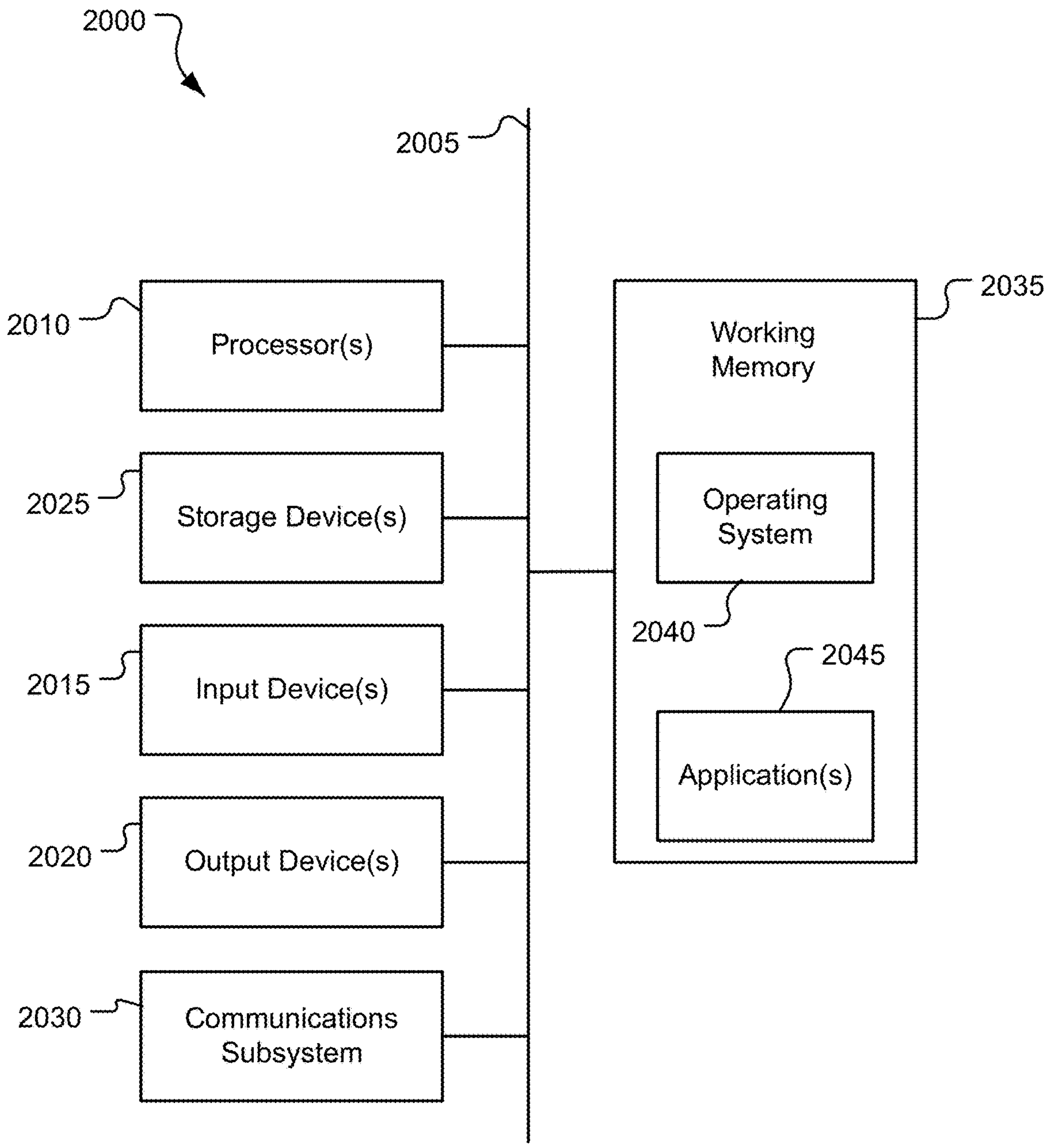
FIG. 20 is a block diagram of an example computer system.

Referring to FIG. 20, a block diagram of an example computer system 2000 is shown. A computer system 2000 as illustrated in FIG. 20 may be incorporated as part of the previously described computerized devices. For example, the computer system 2000 may be used as a controller, such as the controllers 710, 1116, 1412, the positioning system 1612, and an imaging reconstruction device communicatively coupled to the VNA 206 and/or a customized analyzer 206 as described in FIG. 2. FIG. 20 provides a schematic illustration of one embodiment of a computer system 2000 that can perform the methods provided by various other embodiments, as described herein, and/or can function as the host computer system. It should be noted that FIG. 20 is meant only to provide a generalized illustration of various components, any or all of which may be utilized as appropriate. FIG. 20, therefore, broadly illustrates how individual system elements may be implemented in a relatively separated or relatively more integrated manner.

The computer system 2000 is shown comprising hardware elements that can be electrically coupled via a bus 2005 (or may otherwise be in communication, as appropriate). The hardware elements may include one or more processors 2010, including without limitation one or more general-purpose processors and/or one or more special-purpose processors (such as digital signal processing chips, graphics acceleration processors, and/or the like); one or more input devices 2015, which can include without limitation a mouse, a keyboard and/or the like; and one or more output devices 2020, which can include without limitation a display device, a printer and/or the like.

The computer system 2000 may further include (and/or be in communication with) one or more non-transitory storage devices 2025, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 2000 might also include a communications subsystem 2030, which can include without limitation a modem, a network card (wireless or wired), an infrared communication device, a wireless communication device and/or chipset (such as a Bluetooth device, an 802.11 device, a WiFi device, a WiMax device, cellular communication facilities, etc.), and/or the like. The communications subsystem 2030 may permit data to be exchanged with a network, other computer systems, and/or any other devices described herein. In many embodiments, the computer system 2000 will further comprise a working memory 2035, which can include a RAM or ROM device, as described above.

The computer system 2000 also can comprise software elements, shown as being currently located within the working memory 2035, including an operating system 2040, device drivers, executable libraries, and/or other code, such as one or more application programs 2045, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 2025 described above. In some cases, the storage medium might be incorporated within a computer system, such as the system 2000. In other embodiments, the storage medium might be separate from a computer system (e.g., a removable medium, such as a compact disc, remote storage, such as cloud-based storage), and/or provided in an installation package, such that the storage medium can be used to program, configure and/or adapt a general purpose computer with the instructions/code stored thereon. These instructions might take the form of executable code, which is executable by the computer system 2000 and/or might take the form of source and/or installable code, which, upon compilation and/or installation on the computer system 2000 (e.g., using any of a variety of generally available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 2000) to perform methods in accordance with various embodiments of the disclosure. According to a set of embodiments, some or all of the procedures of such methods are performed by the computer system 2000 in response to processors 2010 executing one or more sequences of one or more instructions (which might be incorporated into the operating system 2040 and/or other code, such as an application program 2045) contained in the working memory 2035. Such instructions may be read into the working memory 2035 from another computer-readable medium, such as one or more of the storage device(s) 2025. Merely by way of example, execution of the sequences of instructions contained in the working memory 2035 might cause the processor(s) 2010 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 2000, various computer-readable media might be involved in providing instructions/code to processor(s) 2010 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 2025. Volatile media include, without limitation, dynamic memory, such as the working memory 2035. Transmission media include, without limitation, coaxial cables, copper wire, free space, and fiber optics, including the wires that comprise the bus 2005, as well as the various components of the communication subsystem 2030 (and/or the media by which the communications subsystem 2030 provides communication with other devices).

Common forms of physical and/or tangible computer-readable media include, for example, a thumb drive, a memory card, floppy disk, a flexible disk, hard disk, magnetic tape, or any other magnetic medium, a CD-ROM, any other optical medium, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 2010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 2000. These signals, which might be in the form of electromagnetic signals, acoustic signals, optical signals and/or the like, are all examples of carrier waves on which instructions can be encoded, in accordance with various embodiments of the disclosure.

The communications subsystem 2030 (and/or components thereof) generally will receive the signals, and the bus 2005 then might carry the signals (and/or the data, instructions, etc. carried by the signals) to the working memory 2035, from which the processor(s) 2005 retrieves and executes the instructions. The instructions received by the working memory 2035 may optionally be stored on a storage device 2025 either before or after execution by the processor (s) 2010.

The processor(s) 2010 may be capable of running at least one algorithm and to utilize at least one input and at least one output. Inputs to an algorithm may include system values, signal and/or data outputs from microwave receivers and/or transceivers, user inputs, user files, signals and/or data from other sensors and/or imagers, signals and/or data input from earlier system runs and the like. Outputs may include data signals, data files, two-dimensional and/or three-dimensional images that may be displayed on a display device, sequences of images that may be played and/or manipulated by a user, images including highlights and/or color-coding, and the like. A reconstruction algorithm may take data from a sensor part and/or from a processor part and may calculate an image of an OUT or other object within the sensor.

In an example, an image produced by the dielectric tomography system may be displayed for a user using an output device 2020, such as a display device. Examples of display devices include but are not limited to computer monitors, televisions, screens, touch sensitive displays, smart phone displays, tablets, game displays, virtual reality displays, electronics displays, and the like. A user may be a human, such as a technician, a system operator, a patient, a doctor, an engineer, and the like. In an example, an image may be manipulated and/or controlled by a user. For example, a user may be able to zoom in and/or zoom out on any part or portion of the image. A user may be able to move an image in and/or out and/or up and/or down and/or may be able to rotate the image. A user may be able to highlight a portion of an image, such as by color-coding and/or by bolding and/or by bringing to the front, and/or by graying out and/or removing background materials. A user may be able to show a 2-dimensional slice of a 3-dimensional image. A user may be able to hover over, click on, and/or enter markers or coordinates for a certain portion of an image and associated parameters of the image may be displayed along with the image and/or reported to the user. Multiple images may appear in succession so that the image appears to be moving or turning. Images with different resolutions may be displayed at different times. For example, low resolution images may be displayed while higher resolution images are measured and/or processed and/or generated.

The computer 2000 may be configured to store certain system values to be used in the system operation. By way of example, but not limitation, the processor may store system values related to the performance of the transceivers in the sensor, to the dielectric properties of the coupling medium, to the object under test being scanned, characterization and/or calibration data, error values and/or coefficients, and the like. The computer 2000 may store system values that are determined when there is no object under test in the sensor. The computer 2000 may store system values determined when there is a known object in the sensor. By way of example but not limitation, a known object may be a scatterer with certain properties known to the system. In an example, known objects may be used to calibrate and/or initiate and/or characterize and/or ready the system for operation imaging an object that is not known to the system. By way of example, but not limitation, the processor may store system values that are error values or error coefficients that have been determined based at least in part on reflectometer data from the sensor.

The computer 2000 may be configured to store a range of system values and may choose which of the stored values to use in system operation based on monitored parameters in the dielectric tomography system. For example, the stored system values may be dielectric properties of the coupling medium at different temperatures and the system may monitor the temperature of the coupling medium and choose the system value associated with the measured temperature when processing signals in the system. The computer 2000 (e.g., the working memory 2035) may be specific to a particular dielectric tomography system and may be determined based on a parts list and/or a sensor configuration and/or a place of manufacture and/or a place of performance, and the like. In an example, a dielectric tomography system may be characterized and/or tested when it is assembled, and certain system values or ranges of system values may be stored in the computer 2000 based on measured results from the characterization and/or testing. The accuracy of the dielectric tomography system may rely on the stored system values and/or the range of stored system values. The dielectric tomography system may include monitoring capabilities that may be used to determine the accuracy of the system based on the monitored parameters.

The system values stored in the computer 2000 may be determined by imaging at least one known object such as a scatterer with certain properties. The at least one known object may be moved in the sensor and microwave signals may be transmitted and received when the known object is at one position or multiple positions within the sensor volume. The known object may be anisotropic and may be highly anisotropic. The known object may be a wire and/or may be an object whose length exceeds its cross-sectional diameter. The known object may be substantially cylindrical and at least partially composed of a conductor. In an example, the relevant properties of any scatterers, probes, and containers are communicated to the computer 2000 running calibration and/or characterization and/or error correction algorithms. The output of the calibration and/or characterization and/or error procedure may include calibration and/or characterization and/or correction coefficients and may be stored on the computer 2000 attached to one or more sensors. In an example, the sensor output may be stored on a remote computing device such as a server. The results of multiple calibration and/or characterization and/or error correction procedures performed over a period of time may be compared in order to detect possible issues with the sensor hardware. The computer 2000 may be configured to notify a technician or an end-user if the calibration and/or characterization and/or error algorithms determine that the sensor hardware needs to be serviced. The electromagnetic properties of the interfaces between two containers comprising the sensor and OUT may be determined during the characterization procedure. Reconstruction algorithms may account for such interfaces during the image reconstruction procedure which may improve final image quality and accelerate numerical convergence. Signals from the computer 2000 may be used to control the position of the known scatterer and/or the position of a sensor relative to the known scatterer. Signals from the computer 2000 may be chosen from a stored set of signals. The signals may be determined by input from an operator, from patient information, and/or based on monitored parameters.

The computer 2000 may include a user interface for a dielectric tomography system configured to receive information and/or data and/or commands and/or instructions and the like from a user. In an example, information entered by a user may comprise information related to the OUT, approximate model parameters for an OUT, information on the status of the system, information from prior runs of the system, calibration and/or initialization and/or characterization information, error values and/or error coefficients, environmental information (such as temperature, humidity, etc.), and the like. Information entered by the user may also comprise information related to the desired resolution of the sensing and or may direct the imaging system to vary the parameters of the system operation to support resolutions of the generated image that vary across the OUT.

A user may enter information into the computer 2000 such as at least one threshold value, positional value, figure of merit, permittivity, permeability, tissue type, and the like and the system may use said input information to set system operation parameters. For example, the dielectric tomography system may measure scattered microwave signals at a certain frequency, range of frequencies, frequency separation and the like. The dielectric tomography system may measure scattered microwave signals at a certain time, time interval and the like. The system may measure scattered microwave signals when the OUT is in a certain position and/or is moved to a variety of relative positions within the sensor. A combination of the examples given above may be selected based on user input information.

Figure 21:
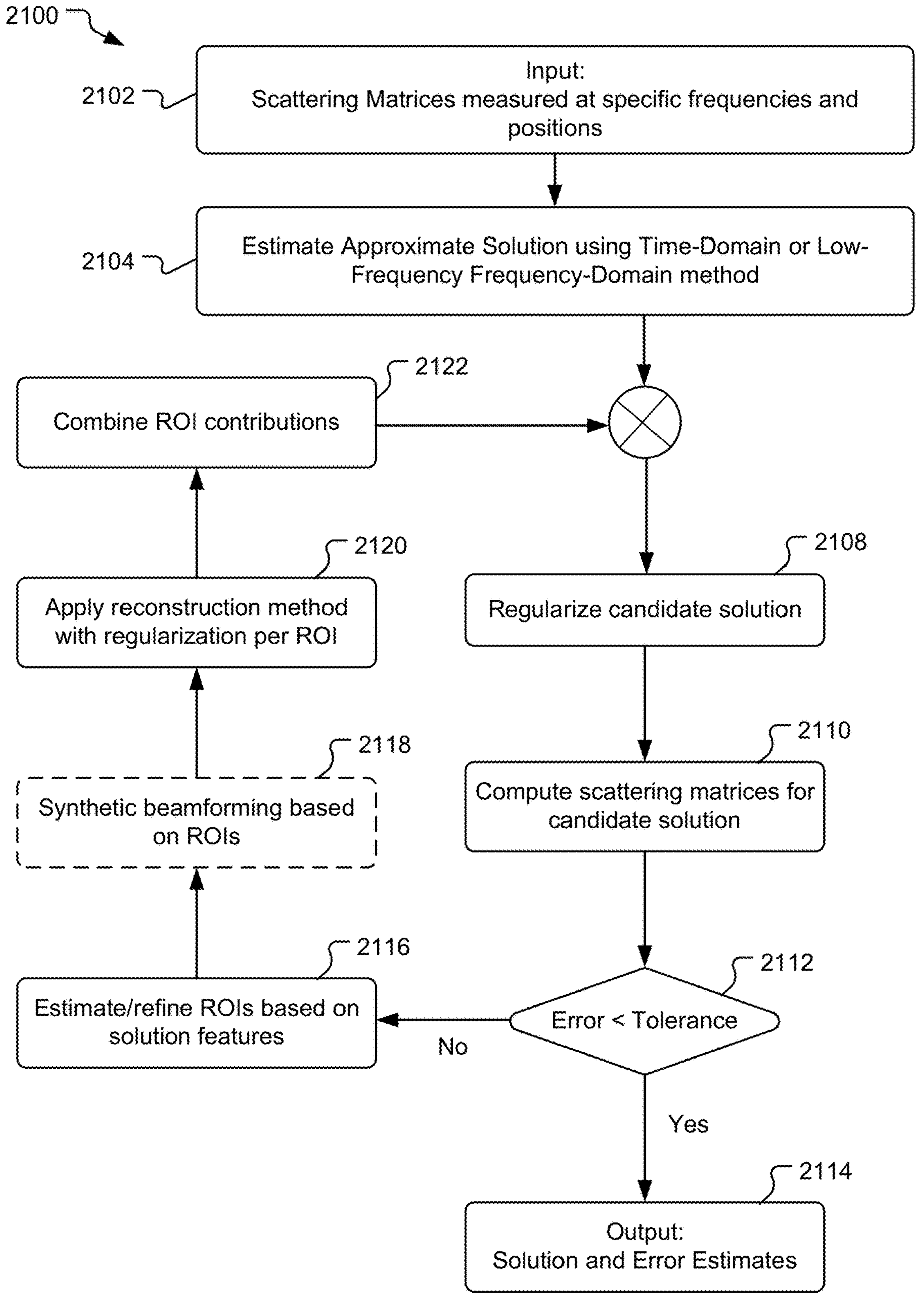
FIG. 21 is a flow diagram of an example image reconstruction process.

Referring to FIG. 21, with further reference to FIGS. 1-20, an example image reconstruction process 2100 includes the stages shown. The process 2100 is, however, an example only and not limiting. The process 2100 may be altered, e.g., by having stages added, removed, rearranged, combined, performed concurrently, and/or having single stages split into multiple stages.

In general, the process 2100 utilizes scattered electromagnetic field data to generate images. The reconstruction process 2100 may utilize a number of complex-valued inputs based on the sensor configuration and characterization data. For example, the number of complex data values may be defined as:

$$N_f \times N_p \times N_{tr} \times (N_{tr} - 1)/2 \tag{1}$$

where:

1. $N_{tr}$ is the number of transceivers;
2. $N_f$ is the number of frequencies; and
3. $N_p$ is the number of measured positions (e.g., along the Z-axis).

The sensor data thus includes a series of $N_{tr} \times N_{tr}$ amplitude and phase and/or complex-valued scattering matrices measured by the RF transceiver sensors at a number $N_f$ of frequencies and $N_p$ positions. Each matrix represents the complex response of the system at a particular frequency, due to the introduction of the object-to-be-imaged at a particular position in the object domain (e.g., the physical region of the imaging apparatus where objects to be imaged are introduced).

The reconstruction process 2100 may be configured to output a multi-channel 3D image representing the dielectric properties of an imaged object. The multi-channel nature of the 3D output may assist in discriminating between different kinds of biological tissue (e.g., muscle from bone, gray matter from white matter), as well as between healthy or diseased tissue. Some examples of multi-channel output may include the real and imaginary parts of the complex permittivity at a particular frequency (e.g., two channels), or the parameters of a multi-pole Debye or Cole-Cole model describing the dielectric behavior of a tissue over a wider frequency range (e.g., $1+2\times N_p$ parameters/channels for a Debye model, $1+3\times N_p$ for a Cole-Cole model, where $N_p$ is the number of poles in the model).

The reconstruction process 2100 may require solving a large (e.g., millions of variables for a 3D output of reasonable resolution), ill-posed (in the formal mathematical sense), nonlinear minimization problem. This may involve creating an initial virtual model of the object to be imagined to simulate what the sensing apparatus should measure when the virtual model is introduced in the object domain (i.e., computing synthetic scattering matrices), comparing this simulated data to the actual measured data, updating the virtual model based on this comparison, then repeating the procedure until a termination criterion has been reached (e.g., suitable termination criteria may include reaching a sufficiently low discrepancy between simulated and measured data, or running the process 2100, and/or the loop comprising steps 2108 through 2122, for a maximum number of iterations). The virtual model generated by the reconstruction process 2100 may converge to the ground truth. In an example, the calibrated and/or characterized model of the sensor may significantly improve the accuracy of the reconstructed object, the speed of convergence of the algorithm, and the like.

In operation, because the reconstruction problem is generally a large nonlinear system involving a significant dynamic range of dielectric contrasts (e.g., the dielectric permittivities of different biological tissues may differ by up to approximately a factor of 10 at a selected frequency), the reconstruction process 2100 may be an iterative process. A regularizing intermediate stage may be utilized to overcome the complications associated with the mathematically ill-posed data sets. In an example, a suitable initial condition (e.g., a well-informed guess) and/or initial virtual model may be provided as an input, and suitable constraints ("priors") may be applied, such as limiting the algorithm to consider physically plausible dielectric values, to improve the image reconstruction.

At stage 2102, the process includes receiving an input including scattering matrices and/or signal phase and amplitude information measured at specific frequencies and positions. A computer 2000 is a means for receiving the input. In an example, the computer 2000 may be communicatively coupled to an apparatus capable of determining the magnitude and phase of the transmitted and received signals such as a vector network analyzer (VNA) and/or a customized analyzer 206. In an example, the scatterer 1606 may be inserted into the sensor 1506 while a transmitter (or transceiver) is transmitting via a first antenna (e.g., antenna 308*a*), and one or more receivers (or transceivers) is receiving via one or more receive antennas (e.g., antennas 308*b*-308*h*). The computer 2000 is configured to receive and analyze at least the phase and amplitude information obtained by the receive antennas and/or the transmit antenna. The frequency of the transmitter and the location and/or orientation of the scatterer 1606 may vary and the computer 2000 is configured to obtain and analyze the phase and amplitude information based on the different frequencies and scatterer locations/orientations. In an example, other antennas (e.g., 308*b*-308*h*) may be configured to transmit and the other antennas receive, and the computer 2000 may obtain and analyze the signals based on the different combinations of transmit and receive antennas. The results obtained from a known scatterer 1606 may be used to calibrate and/or characterize the sensor (e.g., the area proximate to a sensor where an OUT is disposed) and/or the sensor domain and/or to determine model parameters and/or to determine error values and/or error coefficients for a VNA 206 and/or a customized analyzer 206. The characterization of the sensor may be utilized to reduce the processing load on the computer 2000 to establish an image. An OUT may be disposed proximate to a characterized sensor and the computer 2000 may be configured to obtain the complex-valued inputs as described in equation (1) above.

At stage 2104, the process includes estimating an approximate solution using a time-domain or a low-frequency frequency domain method. The computer 2000 is a means for estimating an approximate solution. In an example, to assist in realizing global convergence to a correct solution and reduce the possibility of non-convergence or a convergence to an undesirable local minimum, the reconstruction process may be initialized with an estimate that roughly approximates the true result. The estimate may be based on one or more factors or techniques such as when the nature of the object being imagined is known (e.g., it might be a particular body extremity of an adult individual). The initial estimate may be a low-pass filtered (i.e., blurred) representation of the average dielectric properties of a representative patient. The initial estimate may be generated by a simplified version of the main iterative algorithm, but focusing on a lower set of frequencies, which may tend to penetrate more deeply in biological tissue at the expense of resolution. The initial estimate may be generated via time-domain radar-inspired algorithms, and/or through the use of other imaging modalities, such as optical cameras, lidar, or ultrasound, from which the basic morphology of the object to be imaged may be derived. The initial estimate may also be referred to as the virtual model, the initial virtual model and/or a suitable initial condition (e.g., a well-informed guess). Combinations of these techniques, and other information, may also be used to generate the estimated approximate solution. In general, these estimated approximate solution techniques may be utilized to speed up the reconstruction process, especially when dealing with large dielectric contrasts.

At stage 2108, the process includes regularizing the candidate solution. The computer 2000 is a means for regularizing the candidate solution. In an example, a subset of frequencies and positions from a set of measured data obtained at stage 2102 may be selected. This may be implemented when it is computationally impractical to attempt to solve for all frequencies and positions simultaneously. This subset may be initially selected from lower frequencies and equi-spaced positions. The candidate solution may be fine-tuned by subsequent steps of the process 2100.

At stage 2110, the process includes computing scattering matrices for the candidate solution. The computer 2000 is a means for computing the scattering matrices. In an example, given a virtual model of the dielectric properties of the object being imaged, either provided by an initialization step, or by stages 2102 or 2104 above, and the calibrated and characterized model of the sensor (e.g., the measurement apparatus), the computer 2000 may be configured to simulate the expected signal amplitudes and phases and/or scattering measurement matrices at a relevant subset of frequencies and positions.

At stage 2112, the process includes determining if an error in the computations is less than a tolerance. The computer 2000 is a means for determining if the error is less than a tolerance. In an example, the computer 2000 may be configured to compare the synthetic scattering matrices computed at stage 2110 to their measured counterparts obtained at stage 2102. If their discrepancy (measured by, e.g., an L1- or L2-norm) is below a predetermined limit, then solution and error estimates may be output at stage 2114. Else, at stage 2116, the process includes estimating and/or refining the region of interest (ROI) and/or updating the virtual model of the object using a method such as the Distorted Born Iterative Method (DBIM) or the Born Iterative method (BIM), regularized using Tikhonov Regularization, Truncated Singular Value Decomposition (TSVD), Conjugate-Gradient Least-Squares (CGLS), or other least-squares techniques (e.g., LSQR), to ensure that the solution is consistent with physics-motivated priors. In an example, the process 2100 may iterate back to stage 2110 based on the refined ROI.

At stage 2118, the process may optionally include synthetical-beamforming based on the ROIs. The computer 2000 is a mean for synthetical beamforming. In an example, the computer 2000 may be configured to analyze the candidate image solution to identify ROIs (e.g., interfaces between tissues or other regions). Based on the virtual models of the object and sensor (measurement apparatus), the computer 2000 may be configured to select an additional subset of frequencies and positions which may resolve finer detail in those ROIs. The computer 2000 may optionally determine transformation coefficients to apply to scattering matrices to synthetically beamform the electromagnetic fields and further enhance the reconstruction of the ROIs.

At stage 2120, the process includes applying a reconstruction method with regularization per ROI. The computer 2000 is a means for applying the reconstruction method. In an example, the computer 2000 may be configured to regularize the entire 3D image using, e.g., Total Variation regularization or other sparsity-promoting techniques, and enforce priors. In some cases, these techniques may be applied at stage 2108, after combining different contributions.

At stage 2122, the process includes combining the ROI contributions. The computer 2000 is a means for applying the ROI contributions. In an example, the computations of stages 2116, 2118, and 2120 may be applied to the candidate solution and the process 2100 may iterate through the evaluation at stage 2112. In an example, a count of the number of iterations (e.g., loops through) the process 2100 may be used to exit the loop and output the solution and error estimates at stage 2114.

In an example, sensor model parameters, also referred to as model parameters, calibration signals/data/parameters and/or characterization signals/data/parameters and/or correction signals/data/parameters/coefficients and/or error coefficients may be determined using a reconstruction process as described above with the object and/or OUT replaced by a known scatterer. In an example, a sensor model may be able to predict the electromagnetic field profiles generated by at least one transmitter, operating at at least one frequency and may be able to predict the electromagnetic field profiles generated by some or any transmitters, operating at some or any frequencies within the sensor domain and/or the measurement domain and/or the interrogation domain. In another example, a sensor model may be able to predict electromagnetic field profiles in the sensor domain and/or the measurement domain and/or the interrogation domain and be able to predict the raw waveforms that are received by at least one transceiver in the sensor system based on the relative position of the transmitting and receiving transceivers and/or the operating parameters of the transceivers and/or the relative position of the sensor and the known scatterer. In an example, multiple coefficients for the sensor model may be referred to as model parameters, calibration coefficients, characterization coefficients, error coefficients and the like.

In an example, the electromagnet fields inside a sensor may be modeled as a superposition of electric fields and/or magnetic fields. In an example, the electric and/or magnetic fields of the superposition may be characterized by amplitudes and/or phases and/or coefficients. In embodiments, the coefficients may be referred to as field expansion coefficients. The electric and/or magnetic fields of the sensor model may include scattered electromagnetic fields.

In an example, at least one of the amplitudes and/or phases and/or coefficients of the sensor model may be determined using characterization and/or calibration signals and/or data and/or information as described herein. In an example, a sensor model with at least one coefficient determined from calibration and/or characterization data may be referred to as a sensor model and/or a calibrated sensor model and/or a characterized sensor model and/or a calibrated and/or characterized model of the sensor.

Figure 22:
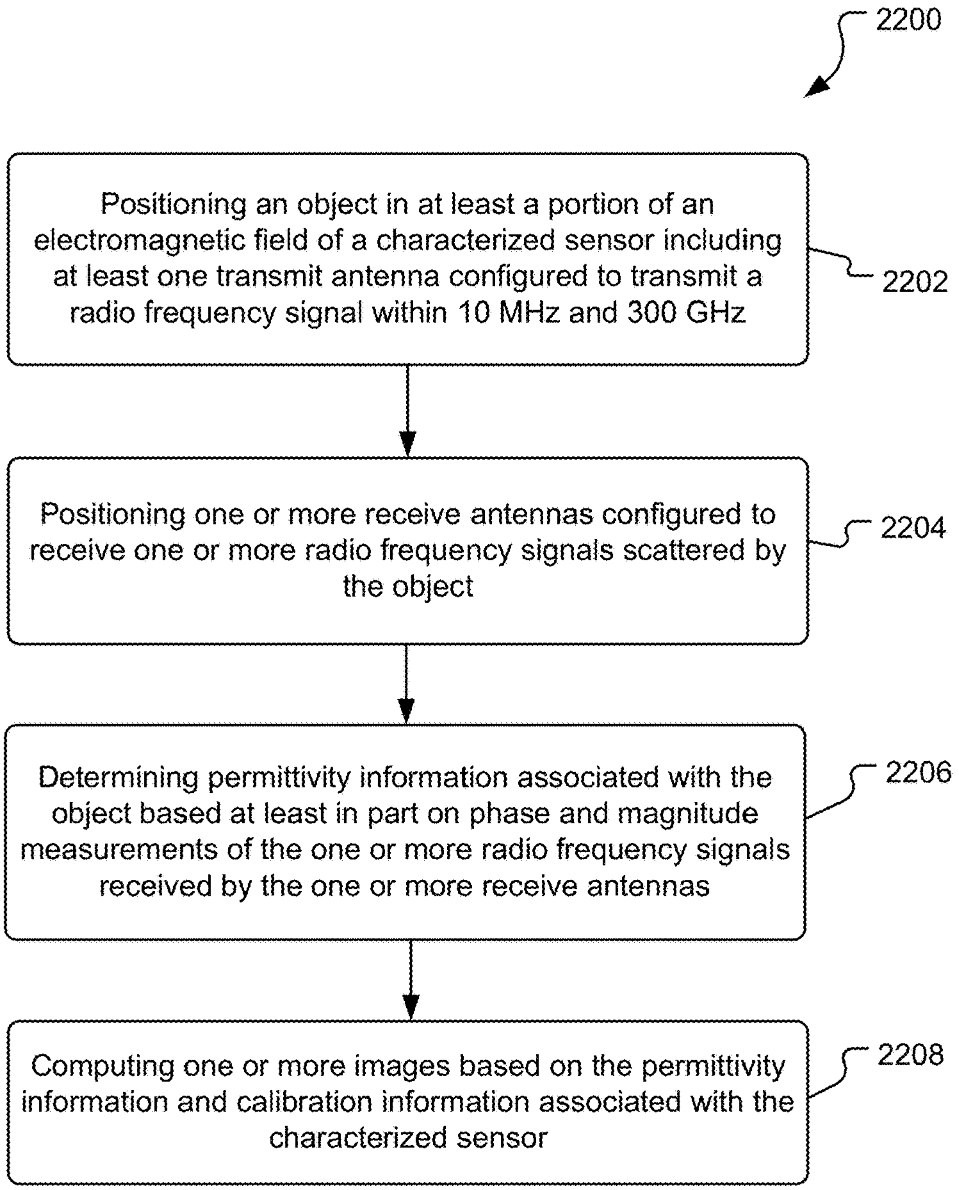
FIG. 22 is a process flow diagram of an example method for obtaining an image with a dielectric tomography system.

Referring to FIG. 22, with further reference to FIGS. 1-21, an example method for obtaining an image with a dielectric tomography system includes the stages shown. The method 2200 is, however, an example only and not limiting. The method 2200 may be altered, e.g., by having stages added, removed, rearranged, combined, performed concurrently, and/or having single stages split into multiple stages.

At stage 2202, the method includes positioning an object in at least a portion of an electromagnetic field of a characterized sensor including at least one transmit antenna configured to transmit a radio frequency signal within 10 MHz and 300 GHz. The object may be an OUT such as a human, or an area of a human to be imaged such as an arm, leg, head, abdomen, etc. Other objects comprising different areas of electromagnetic permittivity may also be imaged. The locations of the electromagnetic fields of the one or more transmit antennas may vary based on the configuration of an imaging sensor. For example, the electromagnetic field in an annulus shaped sensor (e.g., the sensor 310), may extend to the object which may be positioned within the inner wall 312, or within an insert 622, 704, or within a hole 1508, or within the pliable inner wall 1106 for the sensor 1100. The electromagnetic field for a linear sensor 1300 may extend to the area in front of the antennas ***1308a*-*1308c*. The electromagnetic field for an arched sensor 1902 may extend to within the opening 1906. The electromagnetic field may be in other locations based on the antenna configuration of a respective sensor. The characterized container may be one of the annulus shaped sensor (e.g., the sensor 310), the linear sensor 1300, the arched sensor 1902, or other sensors which have been calibrated based on the techniques described in FIG. 16 or FIG. 23**.

At stage 2204, the method includes positioning one or more receive antennas configured to receive one or more radio frequency signals scattered by the object. The one or more receive antennas may be the antennas (and associated receive chains) which are not transmitting in a sensor. For example, in the example sensor 800 may include a transmit antenna 808*a* and a plurality of receive antennas 808*b*-808*h*. In an embodiment, a transmitting antenna 808*a* may also receive scattered signals as described below. The antennas 808*a*-808*h* may have different functionality such that an antenna may be configured to transmit for one period of time, and then receive for other periods of time. Other example sensors described herein may similarly utilize combinations of transmit and receive antennas. In an example, positioning the receive antennas may occur concurrently with positioning the object at stage 2202. For example, positioning the object proximate to a sensor may put the object within the electromagnetic field of a transmit antenna while simultaneously positioning the one or more receive antennas.

At stage 2206 the method includes determining permittivity information associated with the object based at least in part on phase and magnitude measurements of the one or more radio frequency signals received by the one or more receive antennas. In general, RF electromagnetic fields are scattered as a function of the complex permittivity of components and/or objects and/or OUTs that they encounters. The computer system 2000, and an apparatus capable of determining the magnitude and phase of the transmitted and received signals such as a VNA 206 and/or a customized analyzer 206 may be configured to obtain and process the permittivity information for different frequencies as described in in the process 2100.

At stage 2208, the method includes computing one or more images based on the permittivity information and/or characterization information and/or calibration information and/or error coefficients and/or model parameters associated with the characterized sensor. The permittivity information may be processed and transformed into one dimensional (1D) and/or two dimensional (2D) and/or three dimensional (3D) images by the computer 2000 (e.g., based on data obtained by an apparatus capable of determining the magnitude and phase of the transmitted and received signals such as the VNA 206 and/or a customized analyzer 206), and/or with one or more a processors collocated with or remote from the sensor. The images may show permittivity and/or relative permittivity values of the regions and/or components of the object. One or more reconstruction algorithms may be used to determine and provide the one or more images based on the permittivity distribution that most likely generated the scattered signal. In an example, the image reconstruction may be based on the process 2100. The calibration and/or characterization and/or error values and/or error coefficients information and/or model parameters may include the measurements obtained based on the examples in FIGS. 16 and 23. The calibration and/or characterization information may be utilized to characterize the sensor domain and/or the volume proximate to the antennas (e.g., within the object container or in the object domain where the OUT will be measured) and reduce the computational overhead for estimating a solution at stage 2104 in the process 2100.

Figure 23:
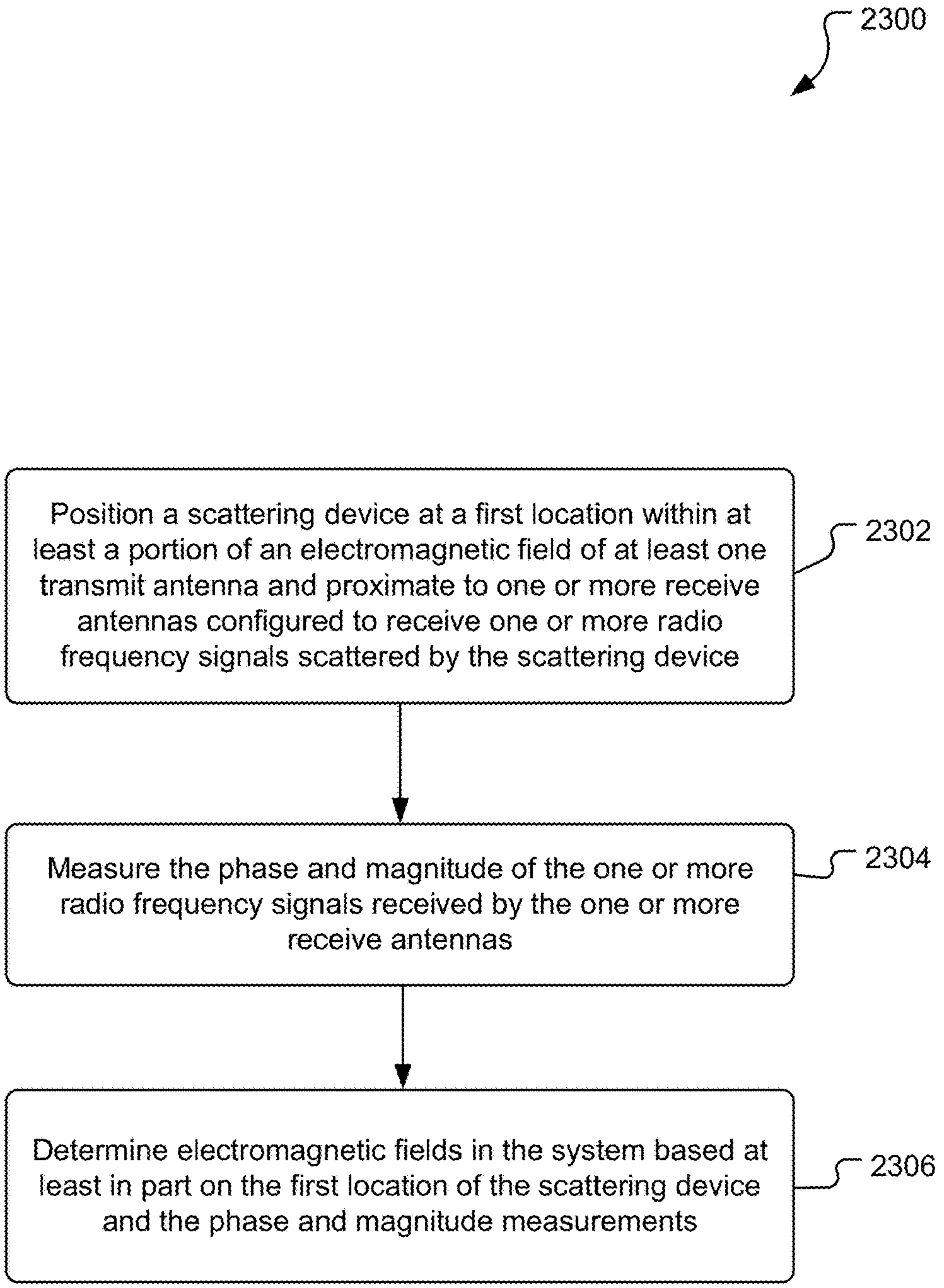
FIG. 23 is a process flow diagram of an example method for characterizing a dielectric tomography system.

Referring to FIG. 23, with further reference to FIGS. 1-21, an example method for calibrating a dielectric tomography system includes the stages shown. The method 2300 is, however, an example only and not limiting. The method 2300 may be altered, e.g., by having stages added, removed, rearranged, combined, performed concurrently, and/or having single stages split into multiple stages.

At stage 2302, the method includes positioning a scattering device at a first location within at least a portion of an electromagnetic field of at least one transmit antenna and proximate to one or more receive antennas configured to receive one or more radio frequency signals scattered by the scattering device. In an example, a transmit antenna may also receive signals scattered by a scattering device. The computer 2000 and wireless positioning system 1612 may be a means for positioning the scattering device. The scattering device may have known electromagnetic characteristics (e.g., a piece of wire or other conductor, a substantially cylindrical conductor with a feature such as a slot and/or whole and/or pattern cut out from the cylinder). For example, referring to FIG. 16, the scattering device may be disposed in the coupling medium 1610 in the region where an OUT will be characterized, or in the coupling medium 1610 between the transceiver antennas and the imaging volume. The scattering device may be disposed in other locations based on the configuration of the dielectric tomography system. In an example, referring to FIG. 14, the scattering device may be disposed between the upper and lower sensor arrays 1404*a*, 1404*b*. In an example, referring to the linear sensor 1300, the scattering device may be disposed in the area 1312 to be examined. The scattering device may be disposed proximate to the electromagnetic fields of other sensor configurations as described herein. The scattering device may be substantially anisotropic. In an example, the scattering device may be substantially cylindrical. In an example, the scattering device may be translated and/or rotated within the electromagnetic field and the scattered microwave signals used to characterize and/or calibrate and/or model various aspects of the respective sensor.

At stage 2304, the method includes measuring the phase and magnitude of the one or more radio frequency signals received by the one or more receive antennas. The computer 2000 and an apparatus capable of determining the magnitude and phase of the transmitted and received signals such as the VNA 206 and/or a customized analyzer 206 are a means for measuring the phase and magnitude of the one or more RF signals. The scattering device has at least partially known electromagnetic properties and/or an at least a partially known point-spread function. At a position and frequency of interest, an apparatus capable of determining the magnitude and phase of the transmitted and received signals such as the VNA 206 and/or a customized analyzer 206 may measure the magnitude and phase of signals and/or the parameters of the scattering matrix due to the interaction of the known scatterer with the RF signals. The scattering device may be moved to a set of 1D, 2D and/or 3D positions inside a sensing region and/or it may be rotated. At each position and frequency of interest, an apparatus capable of determining the magnitude and phase of the transmitted and received signals such as the VNA 206 and/or a customized analyzer 206 may measure parameters (e.g., phase and magnitude of the RF signals) of the scattering matrix due to the interaction of the known scatterer with the RF signals. Determining and processing the magnitude and phase signals and/or the scattering matrix for the scattering device may yield characterization and/or calibration and/or effort parameters and/or coefficients that may be used in the reconstruction algorithm.

At stage 2306, the method includes determining electromagnetic fields in the system based at least in part on the first location of the scattering device and the phase and magnitude measurements. The computer 2000 and an apparatus capable of determining the magnitude and phase of the transmitted and received signals such as the VNA 206 and/or a customized analyzer 206 are means for determining the incident and scattered electric fields. The computer 2000 may be configured to perform an auto-correction by fixing the scattering device at a single point, or by completely removing the scatterer from the sensor and/or coupling medium (e.g., to characterize and compensate for drift effects). In an example, the computer 2000 may be configured to perform an auto-correction by moving the scattering device along a substantially one-dimensional path (e.g., to correct for shifts in the dielectric properties of the coupling medium). The computer 2000 may be configured to perform an auto-correction by moving the scattering device along a substantially two-dimensional surface to characterize the incident and/or scattered fields generated by the transceiver antennas. The computer 2000 may be configured to perform an auto-correction by moving the scattering device along the surface of or throughout the volume of a substantially three-dimensional volume, or along a series of two-dimensional surfaces (e.g., to further account for residual reflections inside the sensor, and other higher-order effects). The computer 2000 may be configured to perform an auto-correction by rotating the scattering device about an axis to characterize the incident fields generated by the transceiver antennas.

Figure 24:
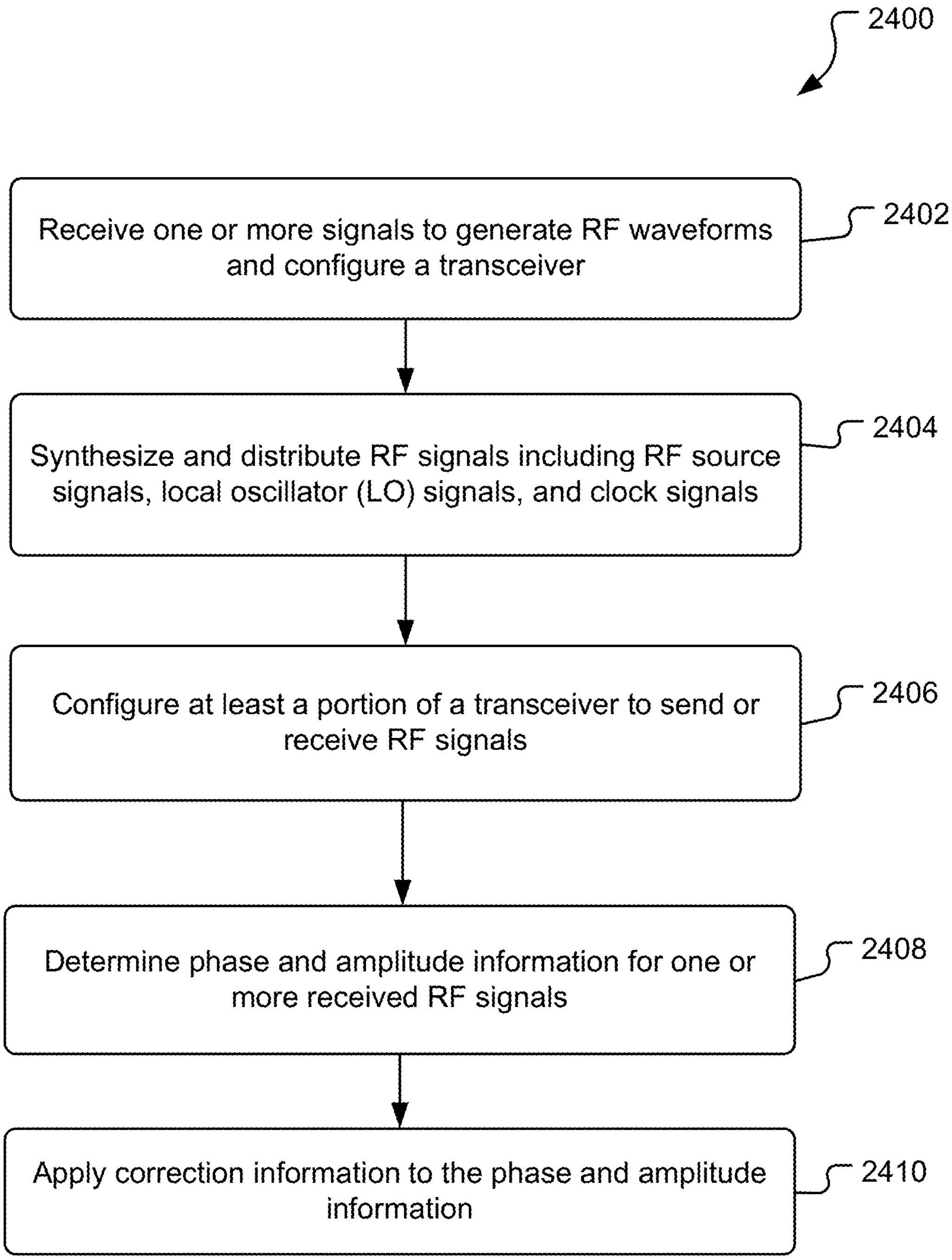
FIG. 24 is a process flow diagram of an example method for supply and receiving microwave or radio frequency (RF) signals with a dielectric tomography system.

Referring to FIG. 24, with further reference to FIGS. 1-23, another example method 2400 for operating and calibrating a dielectric tomography system includes the stages shown. The method 2400 is, however, an example only and not limiting. The method 2400 may be altered, e.g., by having stages added, removed, rearranged, combined, performed concurrently, and/or having single stages split into multiple stages.

At stage 2402, the method includes receiving one or more signals to generate RF waveforms and configure a transceiver. The computer 2000 and/or an apparatus capable of generating RF waveforms such as a VNA and/or a customized analyzer 206 and configuring transceivers such as a customized analyzer 206 are means for receiving signals such as commands and/or applied voltages to generate RF waveforms and configure one or more transceivers. In an example, a customized analyzer may include a processor such as a field programmable gate array (FPGA), an application specific integrated circuit (ASIC), a microcontroller, a graphics processing unit (GPU), and the like that may receive signals (e.g., commands and/or applied voltages), such as from a computer 2000 or another processor. In an example, a customized analyzer may include circuitry implemented to interface a processor to the source of the commands and/or applied voltages via a standardized wired connector such as a USB, USB-C, micro-USB, mini-USB, RS232 and the like and/or to receive command signals wirelessly via standardized and/or customized wireless communication protocols. In an example, commands and/or applied voltages related to which transceiver(s) and/or antenna(s) should transmit RF signals, which transceiver(s) and/or antenna(s) should receive RF signals, the frequency of the RF signals, the duration of the transmitted signals, the settings of switches, amplifiers, attenuators, filter banks, and the like within the transceiver circuitry may be received.

At stage 2404 the method includes synthesizing and distributing RF signals. The computer 2000 and/or an apparatus capable of synthesizing RF signals such as a VNA and/or a customized analyzer 206 and distributing RF signals such as a switching network 208 and/or a customized analyzer 206 are means for synthesizing and distributing RF signals. An apparatus capable of synthesizing RF signals may comprise circuitry for synthesizing an RF source signal such as an oscillator, a voltage-controlled oscillator (VCO), a voltage to frequency converter (VFC), a linear oscillator, a harmonic oscillator, a voltage-controlled crystal oscillator (VCXO), a temperature compensated crystal controlled oscillator (TCXO), a temperature-compensated VCXO (TCVCXO), a clock generator, and the like, and may comprise one or more phase-locked loops (PLLs). In an example, an RF source circuit may comprise an external reference oscillator and loop filter to improve the performance of the synthesizer. Synthesizing and distributing the RF signals may also include synthesizing and distributing local oscillator (LO) RF signals and clock signals.

Figure 25:
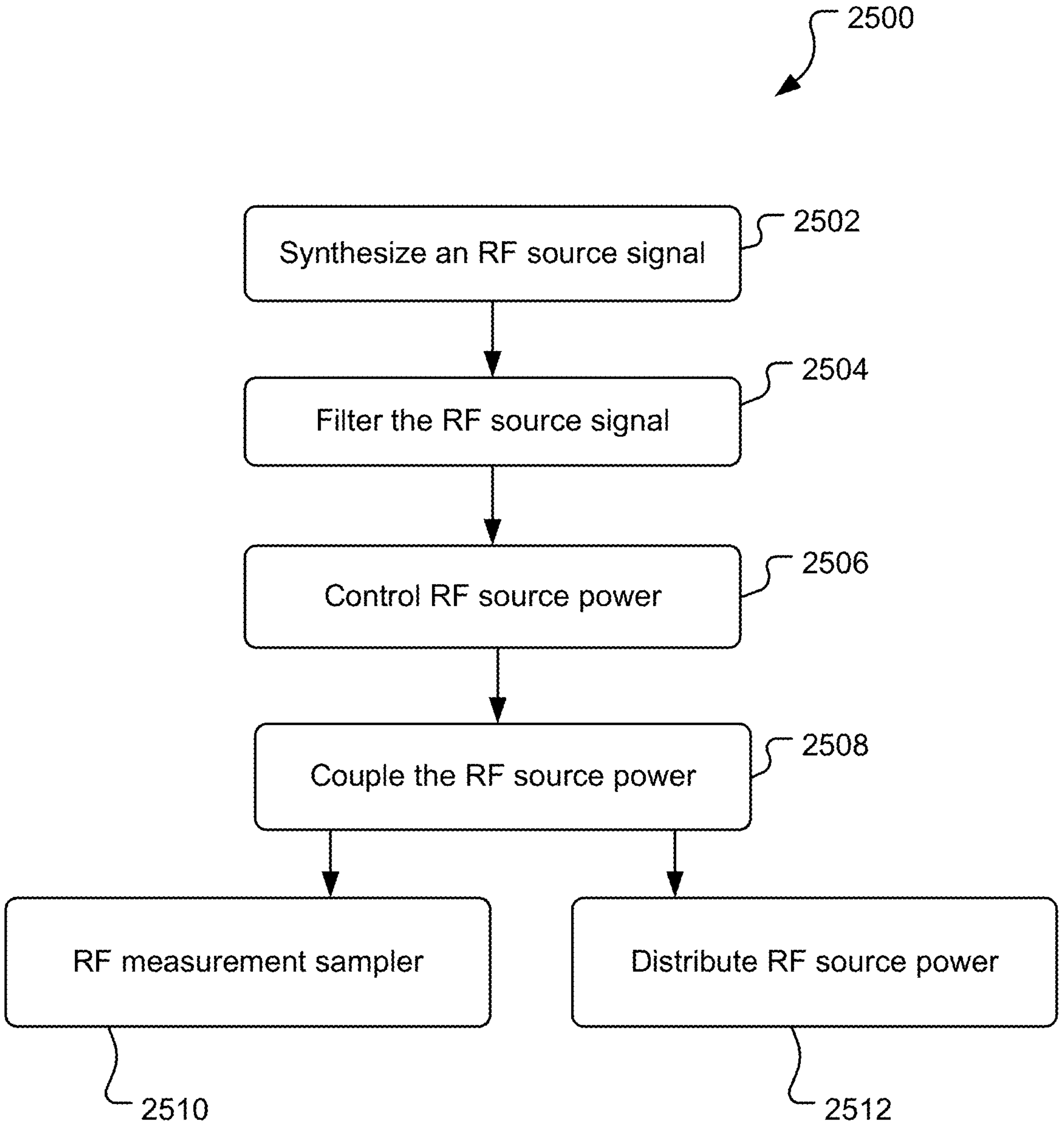
FIG. 25 is a process flow diagram for an example method for generating and distributing an RF source signal with a dielectric tomography system.

In an example, referring to FIG. 25, an example process 2500 for synthesizing and distributing RF source signals at stage 2404 is shown. The process 2500 is, however, an example only and not limiting. The process 2500 may be altered, e.g., by having stages added, removed, rearranged, combined, performed concurrently, and/or having single stages split into multiple stages. The process 2500 may be performed as part of stage 2404 of the method 2400.

At stage 2502, the process includes synthesizing an RF source signal. The RF source signal may be based on various waveforms as known in the art, such as carrier free, stepped frequency continuous wave (SFCW), frequency modulated continuous wave (FMCW), frequency modulated interrupted continuous wave (FMICW), noise modulated continuous wave (NMCW), or combinations of the above. In an example, the RF source signal may be a set of simultaneous CW tones distributed within a frequency band around a center frequency, wherein the center frequency may be in a range of 10 MHz to 300 GHz.

At stage 2504, the method includes filtering the RF source signal. In general, at least one RF filter as is known in the art may be a means for filtering the RF source signal. The at least one RF filter may be a low-pass filter, a high-pass filter, a bandpass filter, a tunable filter, a filter bank, and the like. In an example, two or more RF filters may be cascaded to increase the stopband suppression and/or roll-off compared to a single filter. In an example, referring to FIG. 26, the at least one RF filter may be part of a switchable RF filter bank 2600. For example, a RF switch 2602 may be configured to receive the RF source signal synthesized at stage 2502 and to switch the RF source signal to a variety of RF filters 2604 based on the source frequency. A second RF switch 2606 at the output from the RF filter bank 2604 may be used to switch the signals from the variety of RF filters 2604 to a single output port and/or to multiple output ports from the RF filter bank 2604. In an example, commands and/or applied voltages for filtering the RF source signal may be received from a computer 2000 and/or an apparatus capable of synthesizing RF signals such as the VNA and/or a customized analyzer 206.

Figure 26:
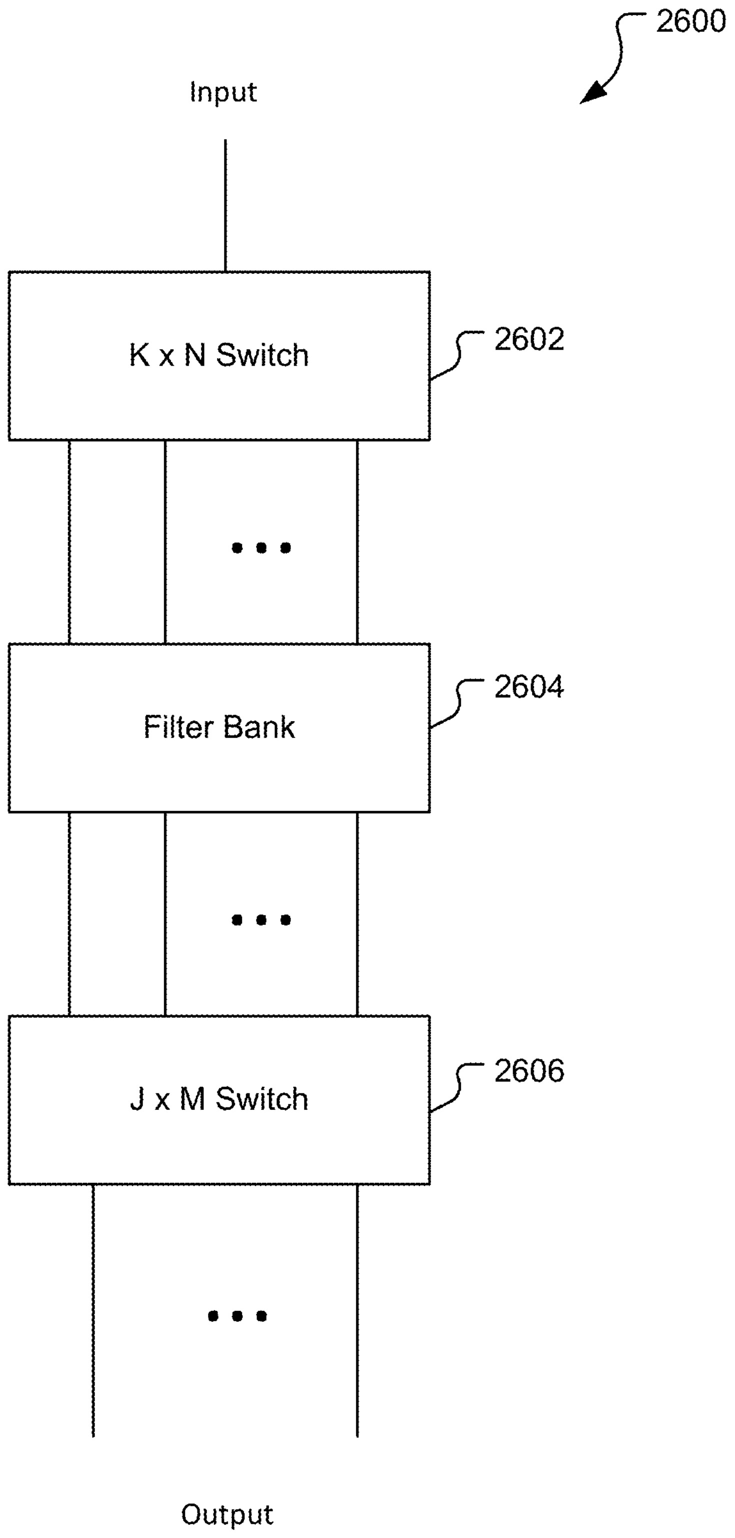
FIG. 26 is a process flow diagram for an example method for filtering RF signals with a dielectric tomography system.

The switchable RF filter bank 2600 in FIG. 26 is an example, and not a limitation. In an example, an RF source signal may be input to a K×N switch 2602 of a switchable RF filter bank 2600, where K is the number of input ports to the switch and N is the number of output ports. The switch 2602 may be an RF switch with absorptive ports. In an example, an RF switch 2602 may comprise substantially symmetric ports. In an example, the RF switch 2602 may be a 1×N switch. In an example, at least one output port of the RF switch 2602 is coupled to at least one RF filter. In another example, up to N output ports of the RF switch 2602 may be coupled to up to N RF filters. In an example, each of the up to N RF filters may filter RF signals in a frequency band or over a frequency range. In an example dielectric tomography system where the transceivers will operate at RF frequencies between 10 MHz and 300 GHz, an RF filter bank may comprise 5 RF bandpass filters, each designed to operate at different center frequencies with passbands of approximately 1 GHz. In another example dielectric tomography system, each RF filter may have a different passband and/or center frequency and/or cut-off frequency and/or loss and/or filter function. The number of RF filters in a switchable RF filter bank 2602 may depend on the frequency range of RF signals that are generated, and the RF signal requirements for acceptable operation.

In an example, the switchable RF filter bank 2600 may comprise four (4) RF low-pass filters. A first filter may have a cut-off frequency of approximately 1.1 GHz, second filter may have a cut-off frequency of approximately 2.1 GHz, a third filter may have a cutoff frequency of approximately 4.2 GHz and a fourth filter may have a cut-off frequency of approximately 6 GHz. The RF switch 2602 may couple RF source signals in the range of 10 MHz to 1.1 GHz to the first filter. The RF switch 2602 may couple RF source signals in the range of 1.1 GHz to 2.1 GHz to the second filter. The RF switch 2602 may couple RF source signals in the range of 2.1 GHz to 4.2 GHz to the third filter. The RF switch 2602 may couple RF source signals in the range of 4.2 GHz to 6.0 GHz to the fourth filter. Such a switchable RF filter bank 2600 could be used to suppress higher order harmonic signals generated by an RF source operating in the frequency range from 10 MHz to 6 GHz. One of ordinary skill in the art will understand the large range of filter options available to design a switchable RF filter bank 2600 to provide appropriate filtering of an RF source signal.

The switchable RF filter bank 2600 may comprise a J×M 2606 switch where the outputs of the up to N filters are coupled to the J inputs of the J×M switch 2606. In an example, J=N and M=1 and the switchable RF filter bank 2600 has a single input port and a single output port. In another example, J>N allowing for the possibility that other signals, besides a single filtered RF source signal could be part of the synthesized RF signal. In yet another example, M>1 allowing for the filtered RF source signal to be distributed to multiple antennas and/or transceivers for example. In another example, multiple RF sources may be connected to the K inputs of the K×N switch 2602 enabling filtering for RF sources and/or combinations of RF sources attached to different input ports of the switch 2602. In an example, synthesizing and distributing RF signals may not include stage 2504 for filtering the RF source signal as shown in FIG. 25.

Referring back to FIG. 25, at stage 2506 the process 2500 includes controlling RF source power. At least one RF attenuator and/or variable attenuator and/or amplifier and/or variable gain amplifier as is known in the art is a means for controlling the RF source power. In an example, the power from an RF source may vary as a function of frequency and a stage for controlling RF source power may be used to control, compensate, mitigate, accentuate, and the like, the frequency-dependent power level. In an example, RF components downstream from the RF source may have frequency dependent losses that may be compensated, mitigated, accentuated and the like by controlling the RF source power. In an example, controlling RF source power may include attenuating an input RF signal before inputting it to an RF amplifier. Such a set-up may be useful for controlling the signal-to-noise (SNR) ratio of the RF source signal at the output of the power controlling stage. In an example, commands and/or applied voltages for controlling the power level of an RF source signal may be received from a computer 2000 and/or an apparatus capable of synthesizing RF signals such as a VNA and/or a customized analyzer 206.

In another example, synthesizing and distributing RF signals may not include a stage 2506 for controlling RF source power as shown in FIG. 25.

In an example, synthesizing and distributing RF source signals at stage 2404 may include coupling RF source power to at least two paths at stage 2508. At least one RF coupler and/or splitter and/or tap and/or switch and/or directional coupler as is known in the art is a means for coupling the RF source power. In an example, the percentage of input RF power that is coupled to an RF reference measurement unit may be approximately 0.001%, 0.01%, 0.10%, 1%, 5%, 10%, 50%, and the like. In an example, an RF coupler is a directional coupler and the percentage of forward input power that is coupled to an RF reference measurement unit may be approximately 0.0010%, 0.010%, 0.10%, 1%, 5%, 10%, 50%, and the like. In another example synthesizing and distributing RF source signals may not include stage 2508 for coupling RF source power. In an example, commands and/or applied voltages for coupling power in an RF source signal to more than one path may be received from a computer 2000 and/or an apparatus capable of synthesizing RF signals such as a VNA and/or a customized analyzer 206. In another example, the coupling is passive, and no commands and/or applied voltages are needed to actuate the coupling.

Figure 28:
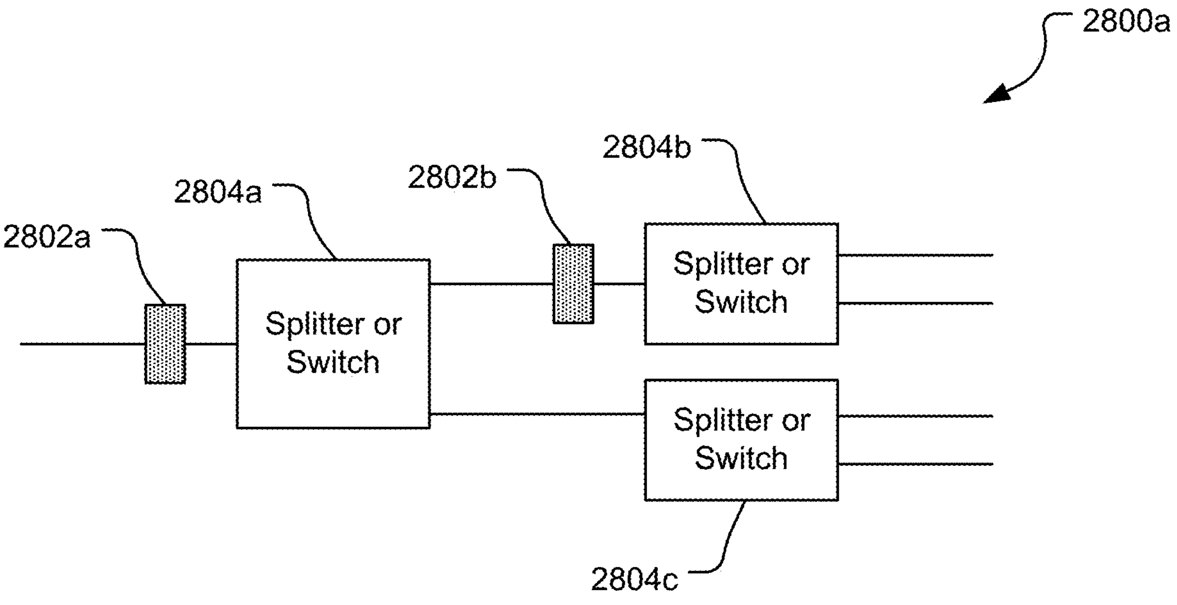
FIG. 28 shows example architectures for distributing RF signals with a dielectric tomography system.
Figure 28:
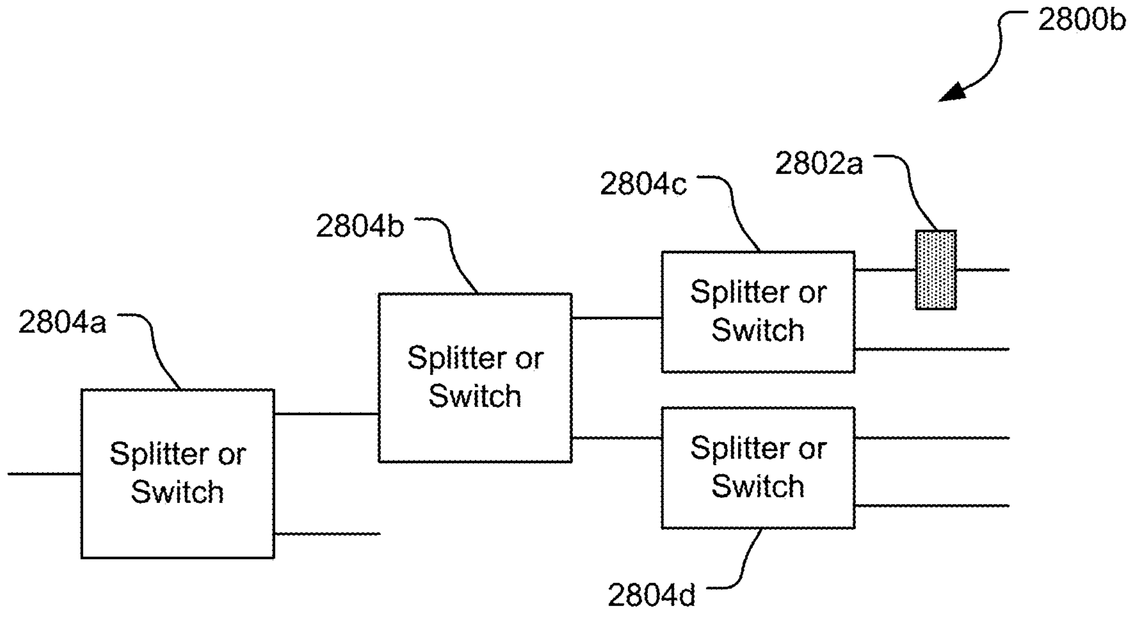
Figure 29:
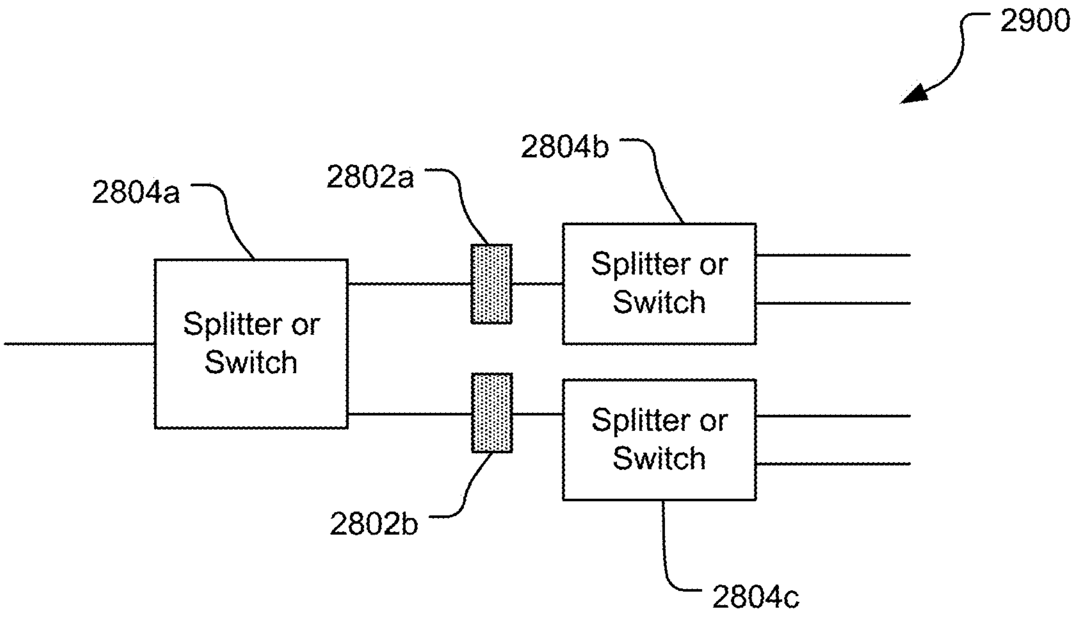
FIG. 29 shows additional example architectures for distributing RF signals with a dielectric tomography system.

In an example, synthesizing and distributing RF source signals at stage 2404 may include distributing the RF source power at stage 2512 as shown in FIG. 25. At least one RF coupler and/or splitter and/or tap and/or switch as is known in the art is a means for distributing the RF source power. In an example, at least one RF switch may be used to distribute the RF source power to two or more paths. In an example, a 1×4 switch may be used to send input RF source power to one of four (4) different paths as determined by a supplied command and/or control voltage. Referring to FIGS. 28 and 29, example splitter and/or switch configurations 2800*a*, 2800*b*, 2900 are shown. In a first example configuration 2800*a*, multiple 1×2 splitters and/or switches 2804*a*, 2804*b*, 2804*c* may be cascaded to achieve 1×4 splitting or switching functionality. For example, a first 1×2 splitter or switch 2804*a* may split or switch input RF source power to one of two output ports. Each output port may then be coupled to the input port of another 1×2 splitter or switch 2804*b*, 2804*c* as shown. In this manner, 1×4 splitter or switch functionality may be achieved using three 1×2 splitters or switches. In a second example configuration 2800*b*, cascading multiple splitters and/or switches 2804*a-d* with smaller numbers of output ports to achieve the functionality of a larger splitter or switch may be advantageous if the performance specifications of the smaller splitters or switches are more beneficial for the application. In an example, additional components such as attenuators and/or couplers and/or filters 2802*a*, 2802*b*, 2802*c* and the like may be included on the input and/or output paths of the splitters or switches. In third example configuration 2900, multiple 1×2 splitters and/or switches 2804*a*, 2804*b*, 2804*c* are configured to realize a 1×4 splitter or switch functionality. Additional components (e.g., attenuators/couplers/filters 2802*a*, 2802*b*) may be operationally coupled in the switching paths. In an example, RF amplifiers with low reverse transmission may be utilized to improve isolation between different channels and/or signals, and/or to reduce crosstalk. In an example, commands and/or applied voltages for distributing an RF source signal may be received from a computer 2000 and/or an apparatus capable of synthesizing RF signals such as a VNA and/or a customized analyzer 206.

Figure 27:
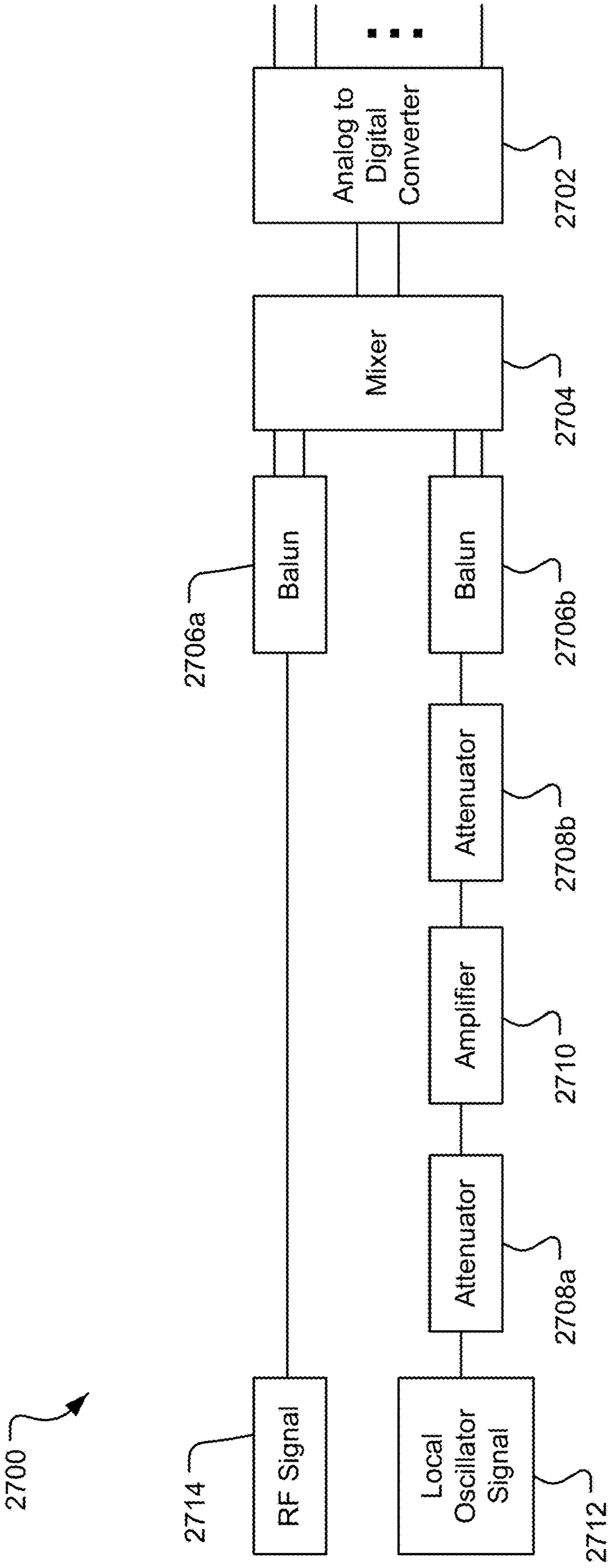
FIG. 27 shows a first example architecture for a reference measurement of an RF signal with a dielectric tomography system.

Referring back to FIGS. 24 and 25, synthesizing and distributing RF source signals at stage 2404 may include RF source signal characterization using an RF measurement sampler at stage 2510. The example architecture shown in FIG. 27 is a means for realizing an RF measurement sampler. An example RF measurement sampler 2700 may include components used to determine the amplitude and/or phase information for the RF signal 2714. In an example, an RF signal 2714 may be a transmitted and/or received RF signal from a transmitter and/or receiver and/or transceiver of a sensor. In the example RF measurement sampler 2700 may include an RF mixer 2704 configured for mixing the RF signal 2714 with a local oscillator (LO) signal 2712, and an analog-to-digital converter (ADC) 2702 may be configured to determine the phase and amplitude information of the RF signal 2714. A frequency of the local oscillator signal 2712 may be offset from the RF signal 2714 by an intermediate frequency that may be in the Hz to GHz range. In an example, the intermediate frequency may be in the MHz range, and may be between 0.1 MHz and 100 MHz. Baluns 2706*a*, 2706*b* may be used to convert a single-ended signal to a balanced and/or differential signal. RF integrated circuits (IC) such as the mixer 2704 that use differential configurations for their internal topology may have improved noise immunity and better overall RF performance and thus may be preferable in some applications. In another example, the RF signal 2714 and/or the LO signal 2712 may be a differential signal and the baluns 2706*a*, 2706*b* may not be used. In an example, an RF IC may yield the desired performance when its internal topology is single-ended, and a balun may not be used.

In an example, the RF signal 2714 and/or the local oscillator signal 2712 may be attenuated and/or amplified and/or power controlled in an RF measurement sampler. A component chain shown in FIG. 27 is an example of one way the power of the RF signal 2714 and/or LO signal 2712 may be controlled, but other implementations as known in the art may be used. In an example RF measurement sampler 2700, the LO signal 2712 may be attenuated or not by an attenuator 2708*a*, amplified or not by an amplifier 2710 and attenuated or not by an attenuator 2708*b* placed after an amplifier 2710. In an example, the amount of attenuation provided by attenuators 2708*a*, 2708*b* and the amount of gain provided by amplifiers 2710 may be controlled by a computer 2000 and/or an apparatus capable for synthesizing and analyzing RF signals such as a VNA and/or a customized analyzer 206. The RF signal 2714 and the LO signal 2712 may be input to the RF mixer 2704 configured to output signals at the sum and/or difference frequencies of the two signals. In an example, the signal at the difference frequency, also referred to as the intermediate frequency, may be input to the ADC 2702. The difference or intermediate signal may be filtered by the ADC 2702 and/or may be optionally filtered by an RF filter (not shown) before being input to the ADC 2702. In an example, the RF mixer 2704 may be an unbalanced mixer, but the one shown in FIG. 27 is a balanced mixer. One of skill in the art will understand that various configurations for mixers may be used in this application, including unbalanced, balanced, double balanced, doubly double balanced, triple balance mixers and the like, active mixers, passive mixers, broadband mixers, and the like. One of skill in the art will understand that mixers are sometimes referred to as converters, downconverters, upconverters and the like and that the functionality of outputting a difference frequency and/or intermediate frequency between two input RF signals may be achieved by means known in the art. To the extent that the performance of the mixer can be controlled by external commands and/or applied voltages, such commands and/or applied voltages for controlling the mixer 2704 may be received from a computer 2000 and/or an apparatus capable of synthesizing and analyzing RF signals such as a VNA and/or a customized analyzer 206.

In an example, the ADC 2702 may be configured to convert one or more substantially analog input signal(s) to one or more digital output signal(s) on one or more output ports of the ADC 2702. The one or more digital output signals may be provided to computer 2000 and/or an apparatus capable of synthesizing and analyzing RF signals such as a VNA and/or a customized analyzer 206. In an example, a computer 2000 and/or an apparatus capable of synthesizing and analyzing RF signals such as a VNA and/or a customized analyzer 206 may determine phase and amplitude information of the RF signal 2714 based on the one or more digital output signals from the ADC 2702 in the example RF measurement sampler 2700.

In an example, the ADC 2702 may be a multi-channel ADC (e.g., a dual- or quad-channel ADC), where the analog inputs of the ADC are each connected to the output a distinct mixer 2704 representing the mixed-down RF signal from a distinct port of the multi-port VNA or customized analyzer. The multi-channel ADC may have high inter-channel isolation to prevent signal contamination between ports.

Referring back to FIG. 24, the method 2400 includes synthesizing and distributing local oscillator (LO) signals at stage 2404. In an example, circuitry for synthesizing LO RF signals may comprise a synthesizer, an oscillator, a voltage-controlled oscillator (VCO), a voltage to frequency converter (VFC), a linear oscillator, a harmonic oscillator, a voltage-controlled crystal oscillator (VCXO), a temperature compensated crystal controlled oscillator (TCXO), a temperature-compensated VCXO (TCVCXO), a clock generator, and the like, and may comprise one or more phase-locked loops (PLLs). In an example, an LO RF circuit may comprise an external reference oscillator and loop filter to improve the performance of the synthesizer. The LO signal distributed at stage 2404 may be utilized by the RF measurement sampler 2700 as the LO signal 2712. Distributing the LO signals includes at least one RF coupler and/or splitter and/or tap and/or switch as is known in the art as a means for distributing the LO signals. In an example, at least one splitter and/or resistive splitter and/or passive splitter may be used to distribute the LO signals to two or more paths as shown in FIG. 29. In an example, at least one RF splitter or switch 2804*a* may be used to send an input LO signal to multiple output paths. In another example multiple splitters and/or switches may be cascaded to distribute the incoming LO RF signal to a larger number of output ports than could be achieved by a single device. For example, a first 1×2 splitter 2804*a* may split an input LO signal to one of two output ports. Each output port may then be coupled to the input port of another 1×2 splitter 2804*b*, 2804*c*. In this manner, 1×4 splitter functionality may be achieved using three 1×2 splitters. In an example, cascading multiple splitters and/or switches with smaller numbers of output ports to achieve the functionality of a larger splitter or switch may be advantageous if the performance specifications of the smaller splitters or switches are more attractive for the application. In an example, additional components such as attenuators and/or couplers and/or filters and/or amplifiers 2802*a*, 2802*b* and the like may be included on the input and/or output paths of the splitters or switches. In an example, commands and/or applied voltages for distributing the LO signals may be received from a computer 2000 and/or an apparatus capable of synthesizing RF signals such as a VNA and/or a customized analyzer 206. In an example, an LO signals may be distributed using passive couplers and may not require voltages or commands to distribute the signal.

In an example, the LO signals may be distributed by inputting the generated LO RF signals into the input port of a 1×2 passive resistive splitter 2804*a* as shown in FIG. 29. Each output port of the splitter may be coupled to an RF amplifier and/or a low noise amplifier (LNA) 2802*a*, 2802*b* and/or an RF attenuator to adjust the LO signal's power level and/or reduce inter-channel crosstalk. The output of each amplifier and/or LNA may be coupled to another 1×2 passive resistive splitter 2804*b*, 2804*c*.

Referring back to FIG. 24, the method 2400 includes synthesizing and distributing clock signals at stage 2404. The computer 2000 and/or an apparatus capable of synthesizing RF signals such as a VNA and/or a customized analyzer 206 and distributing RF signals such as a switching network 208 and/or a customized analyzer 206 are means for synthesizing and distributing clock signals. In operation, the clock signals may be configured to provide a timing reference to multiple chips, components, processors, circuits, and the like within a dielectric tomography system. In an example, the frequency of a clock signal may be in the MHz range and may be between 0.1 MHz and 100 MHz. In an example, clock signals may be distributed as described above for RF source signals and LO RF signals. In another example, clock signals may be distributed to multiple chips, components, processors, circuits and the like via a clock buffer, a clock divider, a clock demultiplexer, a fanout buffer and the like.

It should be noted that the descriptions of RF source, LO and clock signals above are meant only to provide generalized examples of various components and methods for synthesizing and distributing RF signals, any or all of which may be utilized as appropriate. The descriptions above therefore, broadly explain how individual systems, circuits, components, elements and the like may be implemented in a relatively separated or relatively more integrated manner. It is anticipated that any, some, or all of the functionalities described for use with the RF source signal may also be applied to the LO RF signals and/or to the clock signals. Likewise, functionalities described for use with the LO RF signals and clock signals may be used with the RF source and clock signals, and the RF source and LO RF signals respectively.

Figure 30:
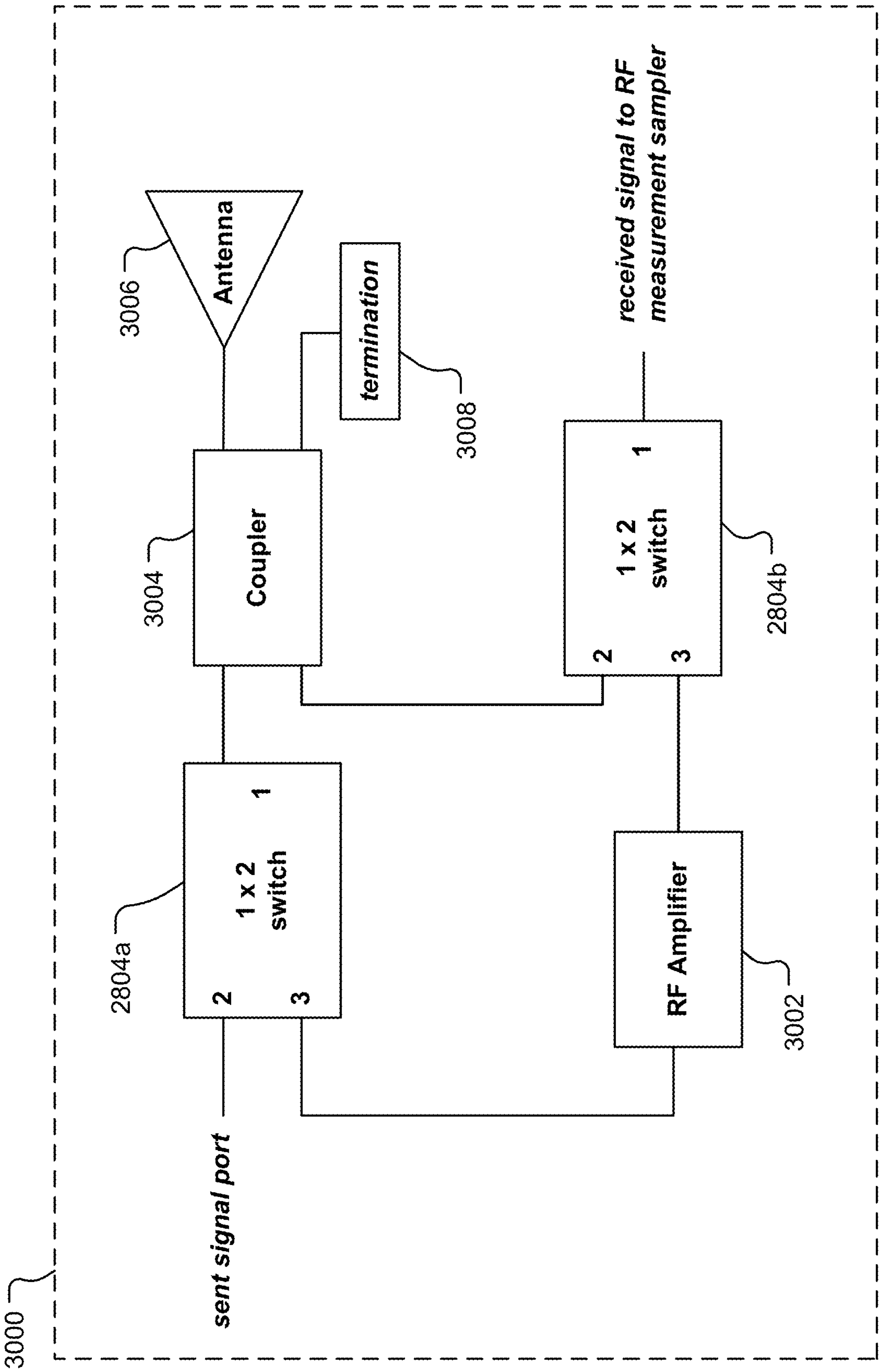
FIG. 30 shows example components in a dual-gain reflectometer in an example transceiver.

At stage 2406 the method 2400 includes configuring at least a portion of a transceiver to send and/or receive RF signals. The computer 2000 and/or an apparatus capable of synthesizing and/or analyzing RF signals such as a VNA and/or a customized analyzer 206 are means for configuring at least a portion of a transceiver to send and/or receive RF signals. Referring to FIG. 30, an example portion of a transceiver 3000 including a dual-gain reflectometer configured to send and/or receive RF signals is shown. In an example, port 2 (as shown in FIG. 30) of a 1×2 RF switch 2804*a* may be connected to one of the distribution ports of the RF source signal described above (and shown as output ports in FIGS. 26-29). If an RF source signal has been distributed to this portion of the transceiver 3000, and if this portion of a transceiver is configured to send and/or transmit an RF source signal, then the 1×2 switch 2804*a* may receive commands and/or applied voltages to route the RF source signal, also referred to as the "sent signal" to port 1 of the 1×2 switch 2804*a*. The sent signal may pass through a coupler 3004 and then arrive at an antenna 3006 where it may be radiated into the dielectric tomography system. In an example, the coupler 3004 may be a directional coupler and the sent signal may traverse the directional coupler 3004 so that most of the sent signal is transmitted to the antenna. In an example, if the directional coupler is a 20 dB coupler, then approximately 1% of the sent signal power will be coupled to a termination port 3008 and approximately 99% of the sent signal power will be coupled to the antenna 3006. In an example, the termination port 3008 may comprise a 50-ohm resistance and/or a terminating impedance.

In this example, where the transceiver has been configured to transmit an RF signal, the same transceiver may receive scattered signals before, during and/or after the transceiver transmits the RF signal. In this example, a portion of the RF signals received by the antenna 3006 may couple through the coupler 3004 to port two of the bottom 1×2 RF switch 2804*b*. Switch 2804*b* may be set to couple ports 2 and 1, which would send the received RF signals to the RF measurement sampler.

The dual-gain reflectometer components of the transceiver 3000 shown in FIG. 30 are configured to receive an RF signal, then scattered signals from the dielectric tomography system may be received by the antenna 3006 and some portion of the signal that passes through the coupler 3004 will be coupled to port 1 of the 1×2 RF switch 2804*a*. In example, if the directional coupler is a 20 dB coupler, approximately 99% of the received signal power will be coupled to port 1 of RF switch 2804*a*. In this configuration, the 1×2 RF switch 2804*a* may receive commands and/or applied voltages to route signals from port 1 to port 3. The received signal output from port 3 of the 1×2 RF switch 2804*a* may be coupled to the input port of an RF amplifier 3002 which may have fixed gain, controllable gain, adjustable gain, and the like. The output of the RF amplifier 3002 may be coupled to a port (port 3 in FIG. 30) of another 1×2 RF switch 2804*b* and the 1×2 RF switch 2804*b* may receive commands and/or applied voltages to route the received RF signal to port 1 of the other 1×2 RF switch 2804*b* as shown. The received RF signal may be communicably coupled to an RF measurement sampler 2700 as shown in FIG. 27 and described above.

In the configuration above, a small portion of the received signal is coupled to port 2 of the RF switch 2804*b*. However, because switch 2804*b* is configured to couple port 3 to port 1, that signal power is absorbed and/or terminated in the switch. In an example, if the directional coupler is a 20 dB coupler and the RF amplifier provides approximately 20 dB of gain then the received RF signal level sent to the RF measurement sampler may be approximately 20 dB higher than the RF received signal level directly after the antenna, and approximately 40 dB higher than the RF received signal level at port 2 of switch 2804*b*. In an example, this implementation may be referred to as a "dual-gain" architecture and/or a dual-gain partial reflectometer because the power level of the RF signal being sent to the RF measurement circuit is significantly higher than the signal level from a conventional partial reflectometer described below.

In an example, after being output by the 1×2 RF switch 2804*b*, the received RF signal may be input to an RF measurement sampler 2700. In an example, the RF signal 2714 to a RF measurement sampler 2700 is a received RF signal from at least a portion of a transceiver 3000 in a dielectric tomography system. In an example, an RF measurement sampler may be used to determine the amplitude and phase information of the received RF signals of a dielectric tomography system.

In another example, the dual-gain reflectometer components of the transceiver 3000 in FIG. 30 may be configured to receive scattered RF signals from a dielectric tomography system by coupling one port of the coupler 3004 to port 2 of the 1×2 RF switch 2804*b* as shown in FIG. 30. In this example, the 1×2 RF switch 2804*b* may receive commands and/or applied voltages to route signals on port 2 of the 1×2 RF switch 2804*b* to port 1. In an example, if the directional coupler is a 20 dB coupler, then the received RF signal level sent to the RF measurement sampler 2700 may be approximately 20 dB lower than the RF signal level directly after the antenna. In this example, approximately 99% of the received signal is coupled to port 1 of the 1×2 RF switch 2804*a*. This signal may be absorbed by switch 2804*a* and/or may be attenuated in RF amplifier 3002 if little or no power is applied to amplifier 3002 and/or may be absorbed by switch 2804*b*. In this configuration, a portion of a transceiver may not include, and/or may not utilize 1×2 RF switch 2804*a* and/or RF amplifier 3002. If a portion of a transceiver does not include 1×2 RF switch 2804*a*, then one port of the coupler 3004 may be connected to one of the distribution ports of the RF source signal described above (and shown as output ports in FIGS. 26-29). The received RF signal output from port 1 of the 1×2 RF switch 2804*b* may be communicably coupled to an RF measurement sampler 2700 as shown in FIG. 27 and described above. In an example, the RF signal 2714 input to an RF measurement sampler is a received RF signal from at least a portion of a transceiver 3000 in a dielectric tomography system. In an example, an RF measurement sampler may be used to determine the amplitude and phase information of a received RF signal of a dielectric tomography system.

In an example, the dual-gain reflectometer components of the transceiver 3000 shown in FIG. 30 may be configured to receive scattered RF signals from a dielectric tomography system by coupling one port of the coupler 3004 directly to the RF measurement sampler. In this example, the dual-gain reflectometer components of the transceiver 3000 shown in FIG. 30 does not include an/or utilize 1×2 RF switch 2804*b*. In this example, the partial reflectometer may be referred to as a conventional partial reflectometer, of the type described in the references included herein.

In an example, the dual-gain partial reflectometer may deliver a received RF signal to the RF measurement sampler that is (A+B) dB stronger than that delivered by the conventional partial reflectometer, where “A” dB is the coupling ratio of the directional coupler and “B” dB is the gain of the RF amplifier. For example, if coupler 3004 is a 20 dB coupler and RF amplifier 3002 has a gain of 12 dB, the received RF signal level input to the RF measurement sampler will be approximately 32 dB higher than that of a conventional partial reflectometer. A dual-gain partial reflectometer may be particularly advantageous in dielectric tomography systems where the received scattered signals may be orders of magnitude smaller than the transmit signal. A dual-gain partial reflectometer may be particularly advantageous in a customized analyzer 206 used to determine received signal amplitude and phase information and/or S-parameters in lossy signal environments.

At stage 2408, the method 2400 includes determining phase and amplitude information for one or more received RF signals. The computer 2000 and/or an apparatus capable of analyzing RF signals such as a VNA and/or a customized analyzer 206 are means for determining the phase and amplitude information for received RF signals. In an example, the VNA and/or customized analyzer 206 may be configured to operate at frequencies up to 10 GHz and higher to obtain magnitude and phase information and/or in-phase and quadrature (I/Q) information and/or scattering parameter measurements (i.e., S-parameter measurements). A customized analyzer may be configured to measure one frequency at a time and determine a subset of magnitude and phase information and/or in-phase and quadrature (I/Q) information S-parameter data at each frequency. The magnitude and phase data and/or in-phase and quadrature (I/Q) data and/or S-parameter data may include phase and magnitude information for the transmitted (incident) and received (reflected) signals. For example, since one port (e.g., one antenna) is transmitting at a time for each frequency, this enables the measurement of respective transmitted waves and the reflected waves at the receiving ports.

At stage 2410, the method 2400 includes applying correction information to the phase and amplitude information. The computer 2000 and/or an apparatus capable of analyzing RF signals such as a VNA and/or a customized analyzer 206 are means for applying correction information. The correction information may include error correction and/or calibration coefficients. Error correction and/or calibration coefficients for a sensor may be determined by comparing measured phases and/or magnitudes of transmitted and reflected waves to the predicted values for those same parameters determined by electromagnetic modeling of the physical and electrical properties of the sensor In an example, an electromagnetic scattering device may be used to calibrate and/or characterize the sensor before an object is measured. The electromagnetic scattering device may be an extended object and may be moved relative to the transmit and receive antennas through a combination of rotations and/or translations. Such a sensor may be modeled to solve for the predicted 3-D electromagnetic propagating and/or waveguide modes of the structure and the expected phase and magnitude measurements by multiple receiver antennas at different relative positions and orientations of a sensing domain and an object and while transmitting and receiving RF signals at a certain frequency. The error correction and/or calibration coefficients may be determined by comparing the measured and predicted values. These error correction and/or calibration coefficients may be applied to and/or corrected for and/or de-embedded from measured values of phase and magnitude determined at stage 2408.

In an example, error correction and/or calibration coefficients may depend on the properties of RF cables that communicably couple electronic circuits and antennas in the sensor. In an example, a customized analyzer realized using circuit boards that can be attached to the sensing domain, so that the analyzer moves along with the sensing domain, may improve the accuracy of the determined error coefficients at different relative positions and orientations between the sensing region and the object and or OUT.

Figure 31:
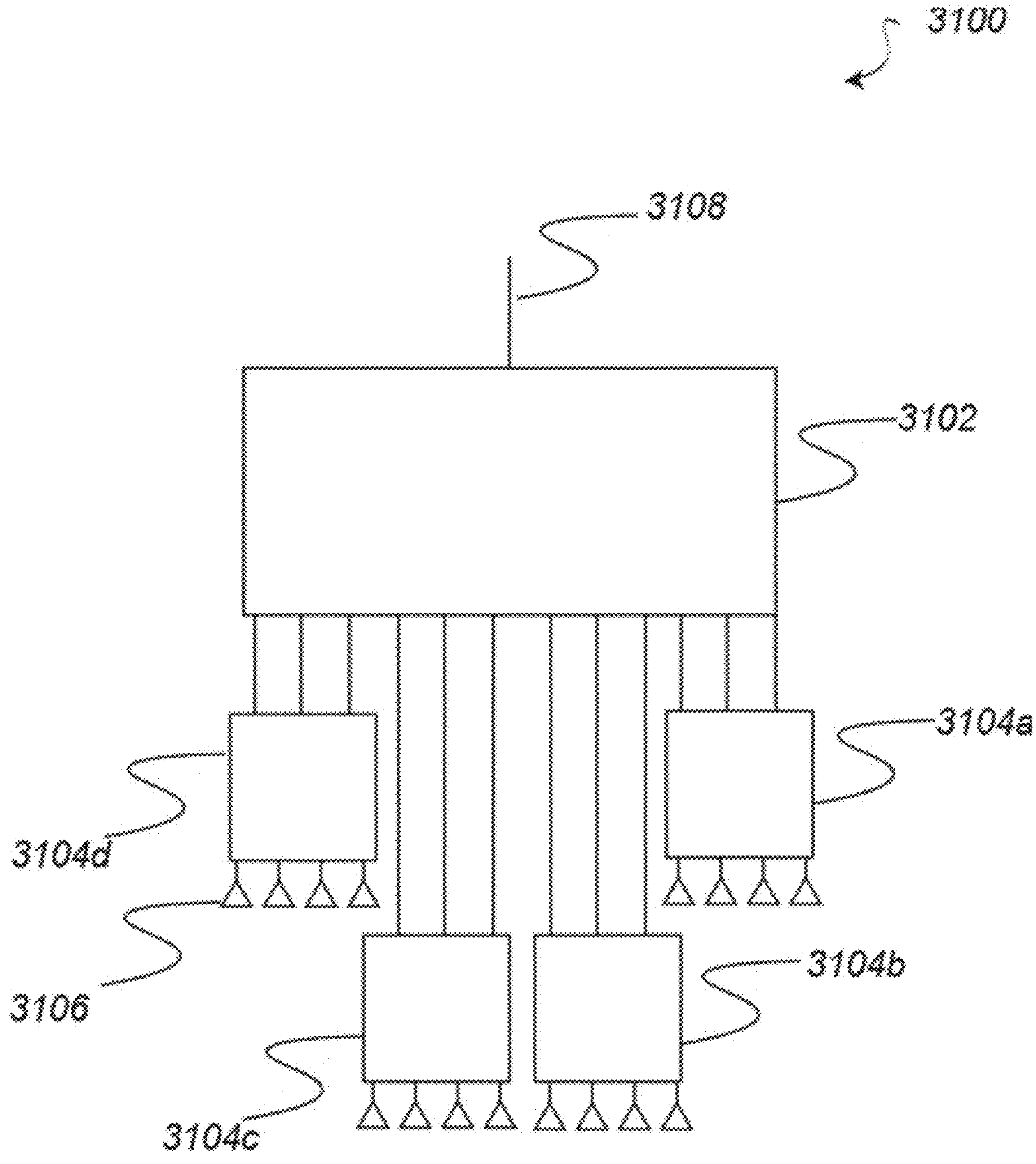
FIG. 31 shows an example of how circuit boards may be communicably coupled in the present disclosure.

Referring to FIG. 31, a block diagram of one example of circuit boards 3100 communicably coupled in a customized analyzer, such as the VNA and/or a customized analyzer 206. In an example, the circuit boards 3100 may comprise at least a first circuit board 3102 configured to receive at least one command from a processor or computer 2000 and/or user interface and/or control interface via an input 3108. The command may include instructions to generate an RF source signal, an LO RF signal and/or a clock signal (e.g., as described at stage 2404). The command may include instructions to configure transceivers. The command may include instructions related to which antennas 3106 of the sensor will transmit RF signals and which antennas 3106 will receive RF signals and which transceivers will implement dual-gain partial reflectometers. RF switches in the first circuit board 3102 may be configured to route at least one of the RF source, LO RF, and clock signals to a designated portion of a transceiver and/or antenna. In an example, an RF source signal may be routed via at least one RF switch to at least one antenna in the antennas 3106. In an example, an LO RF and/or a clock signal may be routed to portions of one, some or all the circuits in the transceiver 3000 associated with antennas 3106 via passive couplers, resistive couplers, splitters, buffers, dividers, fanouts, and the like. In an example, commands and/or applied voltages may include instructions related to which transceiver(s) and/or antenna(s) should transmit RF signals, which transceiver(s) and/or antenna(s) should receive RF signals, the frequency of the RF signals, the duration of the transmitted signals, the settings of switches, amplifiers, attenuators, filter banks, and the like.

In an example, the circuit boards 3100 may include at least a second circuit board 3104*a*, communicably coupled to the first circuit board 3102. The second circuit board 3104*a* may receive at least one command from a processor or computer 2000 and/or user interface and/or control interface and/or the first circuit board 3102. Additional circuit boards, such as a third circuit board 3104*b*, a fourth circuit board 3104*c*, and a fifth circuit board 3104*d* may be communicatively coupled to the first circuit board 3102 and/or to one another. The number of circuit boards and antennas are examples, and not limitations, as other circuit board and antenna configurations may be used. In an example, each of the circuit boards 3102, 3104*a-d* may include one or more RF measurement samplers 2700 and the dual-gain reflectometer components shown in FIG. 30. The command may include instructions to configure transceivers. The command may include instructions related to which antennas 3106 will transmit RF signals and which antennas 3106 will receive RF signals. RF switches in the circuit board 3102, 3104*a-d* may be configured to route at least one of the RF source, LO RF, and clock signals to a designated portion of a transceiver and/or antennas 3106. In an example, an RF source signal may be routed via at least one RF switch to at least one antenna of the antennas 3106. In an example, an LO RF and/or a clock signal may be routed to portions of one, some or all transceiver circuits 3000 associated with antennas 3106 via passive couplers, resistive couplers, splitters, buffers, dividers, fanouts, and the like. In an example, commands and/or applied voltages may include instructions related to which transceiver(s) and/or antenna(s) should transmit RF signals, which transceiver(s) and/or antenna(s) should receive RF signals, and the settings of switches, amplifiers, attenuators, and the like.

In an example, the RF sensing system 202 may comprise a customized analyzer and the circuit boards 3100 including sixteen (16) antennas 3106. In FIG. 31, only one of the antennas 3106 is labeled for clarity. One or more of the antennas 3106 may be configured to transmit incident RF signals towards an object and one or more antennas 3106 may be configured to receive scattered signals from the object. The receive antennas 3106 may be operably coupled to an apparatus capable of determining the magnitude and phase of the received signals such as the RF measurement sampler 2700 via at least one RF switch as shown in FIG. 30. An RF source generator may be operably coupled to an apparatus capable of determining the magnitude and phase information of the incident or transmitted or sent signal as shown in FIG. 28. One antenna of the antennas 3106 may be excited to transmit at a time while the other antennas are configured to receive. In an example, a transmit antenna may also receive scattered signals and deliver these signals to an RF measurement sampler 2700. In an example, a customized analyzer may be configured to operate at frequencies up to 10 GHz and higher to obtain magnitude and phase information and/or in-phase and quadrature (I/Q) information and/or scattering parameter measurements (i.e., S-parameter measurements). A customized analyzer may be configured to measure one frequency at a time and determine a subset of magnitude and phase information and/or in-phase and quadrature (I/Q) information S-parameter data at each frequency. The magnitude and phase data and/or in-phase and quadrature (I/Q) data and/or S-parameter data may include phase and magnitude information for the transmitted (incident) and received (reflected) signals. For example, since one port (e.g., one antenna of the antennas 3106) is transmitting at a time for each frequency, this enables the measurement of respective transmitted waves and the reflected waves at the receiving ports (e.g., the non-transmitting antennas 3106). In another example, the transmitted waves may be measured and/or characterized at a different position along the RF signal path, such as on the first circuit board 3102, than the reflected waves, which in an example may be determined in circuits positioned on at least one of the additional circuit board (e.g., 3104*a*, 3104*b*, 3104*c*, 3104*d*). After error correction and de-embedding, the scattering matrix (e.g., S-matrix) parameters may be determined at each frequency of operation of the customized analyzer and at each relative position of a sensing domain and an object and/or OUT. The customized analyzer and the circuit boards 3100 are an example, and not a limitation, as other analyzer configurations may be used.

In an example, a relative position and orientation of a sensing domain and an object and/or OUT may be set and the first circuit board 3102 may receive a command (e.g., via the input 3108) to generate an RF source signal at 1.5 GHz for a period of time, Ttx, that will be transmitted by the leftmost antenna 3106 attached to the fifth circuit board 3104*d*. Other antennas 3106 in the customized analyzer may be configured as receive antennas for a period of time, Trx. In an example, portions of the transceivers 3000 attached to the receive antennas will be configured to implement a dual-gain reflectometer. A circuit implementing the method 2400 including stage 2404 may generate an RF signal at 1.5 GHz, optionally filter that signal at stage 2504 by routing it through the appropriate RF filter, optionally control the power at stage 2506 of the 1.5 GHz signal, and then couple the 1.5 GHz signal to an RF measurement sampler 2700 which may determine the magnitude and phase of the 1.5 GHz signal, and to a 1×4 RF switch 2800, which may comprise three (3) 1×2 RF switches as described above. The each of the four output ports of the 1×4 switch may be communicably coupled to a separate one of the four (4) additional circuit boards 3104*a*, 3104*b*, 3104*c*, 3104*d*. In an example, a 1×4 RF switch on the first circuit board 3102 may route the 1.5 GHz signal to additional circuit boards (e.g., 3104*a-d*). The first circuit board 3102 may also generate an LO RF signal at 1.502 GHz and use passive splitters to send the LO signal to additional circuit boards 3104*a*, 3104*b*, 3104*c*, 3104*d*. The first circuit board 3102 may be configured to generate a clock signal at 40 MHz and use passive splitters to send the clock signal to additional circuit boards 3104*a*, 3104*b*, 3104*c*, 3104*d*. In an example, only one of the additional circuit boards 3104*a*, 3104*b*, 3104*c*, 3104*d* receives an RF source signal from the first circuit board 3102 while all four (4) of the additional circuit boards 3104*a*, 3104*b*, 3104*c*, 3104*d* receives LO RF signals and clock signals.

The fifth circuit board 3104*d* may comprise an additional 1×4 RF switch 2800, which may comprise three (3) 1×2 RF switches as described above and may route the RF signal to the left most antenna 3106 attached to it. The portion of the transceiver 3000 associated with the leftmost antenna 3106 of the fifth circuit board 3104*d* may be configured to transmit or send the 1.5 GHz RF signal into the sensor. All other portions of transceivers 3000 will be configured to receive scattered signals.

The additional circuit boards (e.g., 3104*a*, 3104*b*, 3104*c*, 3104*d*) may each comprise an additional 1×4 RF switch, which may comprise three (3) 1×2 RF switches 2800 as described above and may route the RF signal to any of the four (4) antennas 3106 attached to it. The additional circuit boards 3104*a*, 3104*b*, 3104*c*, 3104*d* may each comprise an additional 1×4 splitter, resistive splitter, coupler, divider, and the like, which may comprise three (3) 1×2 splitters, resistive splitters, couplers, dividers, and the like as describe above and may route LO RF signals to the portions of transceivers 3000 associated with the four (4) antennas 3106 attached to it. The additional circuit boards 3104*a*, 3104*b*, 3104*c*, 3104*d* may each comprise additional splitters, resistive splitters, couplers, buffers, dividers, and the like, to distribute clock signals to components and circuits residing on those additional circuit boards. In an example, while at a relative position and orientation of a sensing domain and an object and/or OUT, and while transmitting and receiving RF signals at a certain frequency, a customized analyzer may collect phase and magnitude information for the signal transmitted by one antenna 3106 and for signals received by the other fifteen (15) antennas 3106. In an example, the customized analyzer may also collect phase and magnitude information for signals received by the transmit antenna. This data may be stored and/or manipulated and may be characterized as representing the amplitude and phase information and/or the S-parameters for a dielectric tomography system at a certain frequency and for a certain relative position of a sensing domain and an object and/or OUT. In an example, amplitude and phase information and/or S-parameters may be determined using a customized analyzer at more than one frequency and/or at more than one relative position and orientation of a sensing domain and an object and/or out. In an example, amplitude and phase information and/or S-parameters may be determined for one, some or all of the ports and/or antennas and/or transceivers. In another example, a customized analyzer may directly record magnitude and phase information for one, some or all of the measured transmitted and reflected signals at more than one frequency and/or at more than one relative position and orientation of a sensing domain and an object and/or out. In an example, commands to change the relative position and/or orientation of a sensing domain and an object and/or OUT and/or commands to change a transmit frequency of transceivers may be received from a processor or computer 2000 and/or user interface and/or control interface and/or from circuit boards within the system.

In an example, determining the phases and/or magnitudes and/or S-parameters of a dielectric tomography system at relative positions and orientations of a sensing domain and a known scattering object for a range of transmission frequencies may be referred to as calibrating, characterizing, and/or analyzing the sensor, the RF sensing system, the system, the imager, and the like.

In an example, error coefficients and/or model parameters for a sensor may be determined by comparing measured phases and/or magnitudes of transmitted and reflected waves to the predicted values for those same parameters determined by electromagnetic modeling of the physical and electrical properties of the sensor. In an example, the outer wall 306, top wall 352*a*, and bottom wall 352*b* of a sensor may comprise a metal and/or a good conductor and may be accurately modeled using known electromagnetic techniques. In an example, the outer wall 306 may comprise a material that is nearly transparent to electromagnetic radiation and/or that transmit substantially more electromagnetic radiation than is absorbed and/or scattered by the material, such as acrylic, glass, plastic and the like. An interrogation chamber insert 622, also referred to as an object chamber insert 622, and/or as an object domain may comprise a metal and/or good conductor and may be configured to fit within the inner wall 312. In an example, the metal and/or good conductor may have one or more shapes and/or holes cut out of it. In an example, a known scattering object may be a metallic cylinder with a rectangular hole cut out of it. In an example, a rectangular hole may be approximately 1 in×2 in or 2 in×1 in. In another example, the scattering objects may have holes with different shapes and/or aspect ratios cut out at diametrically opposed locations on the metallic cylinder.

In an example, an insert 622, may be configured as an electromagnetic scattering device and may be used to calibrate and/or characterize the sensor before an object to be measured or an OUT is placed in the insert 622. The electromagnetic scattering device may be an extended object such as a cylinder or plane with electromagnetic features on its surface (such as a metallic cylinder with a hole of any shape and dimension, multiple holes of similar or different shapes and dimensions, and/or patterns of shapes of any size and dimension etched or cut into its surface). Such an extended object may be moved relative to the transmit and receive antennas through a combination of rotations and/or translations. Such a sensor may be modeled to solve for the predicted 3-D electromagnetic propagating and/or waveguide modes of the structure and the expected phase and magnitude measurements by multiple receiver antennas at different relative positions and orientations of a sensing domain and an object and while transmitting and receiving RF signals at a certain frequency. Comparing the measured and predicted values allows one to calculate the error coefficients and/or model parameters for the customized analyzer as it performs in a particular sensor. These error coefficients and/or model parameters may be applied to and/or corrected for and/or de-embedded from measured values of phase and magnitude taken when an object and/or OUT other than a calibration and/or characterization object is in the object domain.

Figure 32:
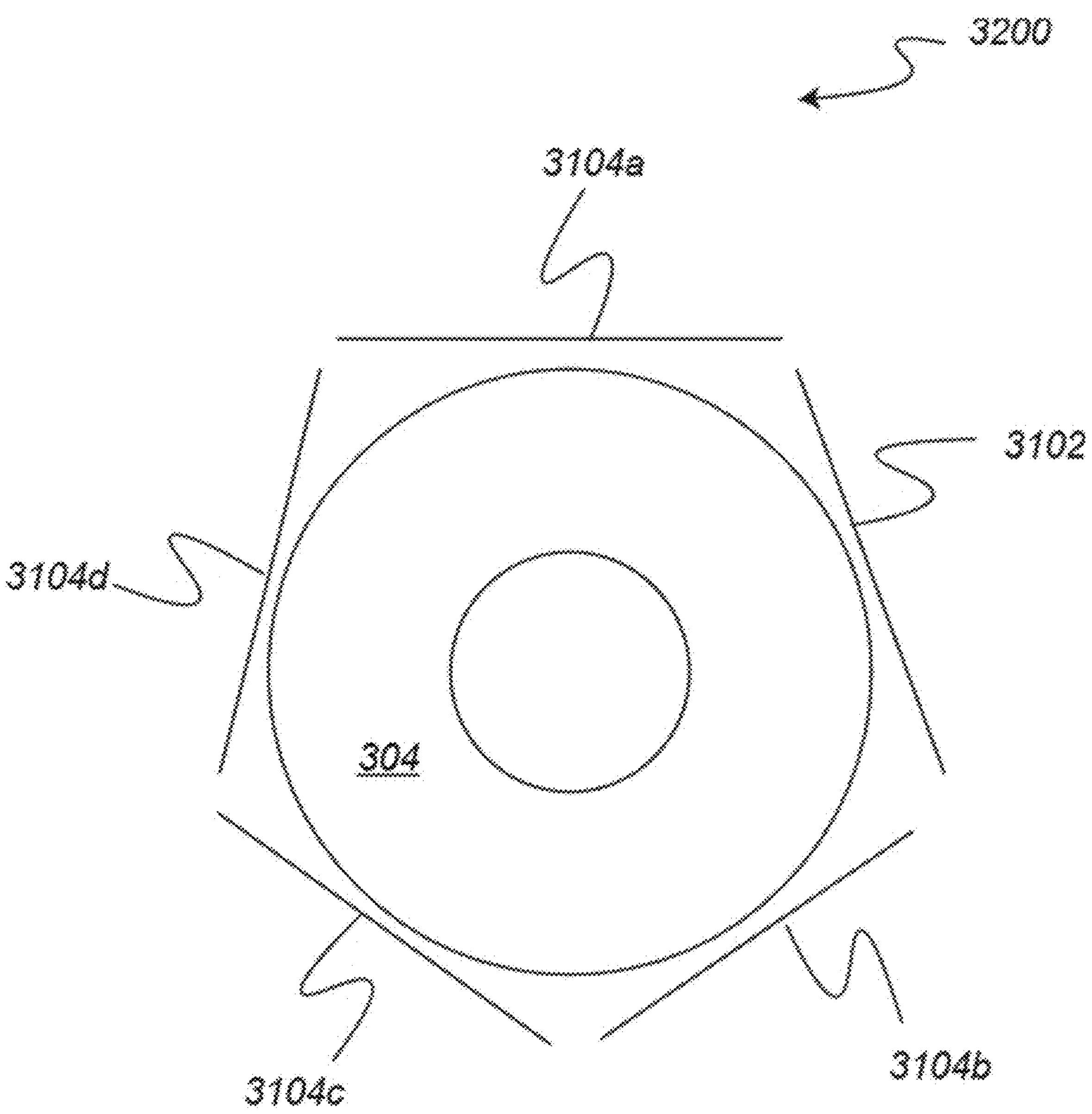
FIG. 32 shows a top view of an example of how circuit boards may be arranged relative to a sensor of the present disclosure.

In an example, error coefficients may depend on the properties of RF cables that communicably couple electronic circuits and antennas in the sensor. In an example, a customized analyzer realized using circuit boards that can be attached to the sensing domain, so that the analyzer moves along with the sensing domain, may improve the accuracy of the determined error coefficients at different relative positions and orientations between the sensing region and the object and or OUT. Referring to FIG. 31 and FIG. 32, a customized analyzer may comprise one or more circuit boards (e.g., 3102, 3104*a*-*d*) that may be communicably coupled using at least one RF cable to at least one antenna 3106. In an example, the first circuit board 3102 may be attached to the sensor using a variety of rigid and/or semi rigid attachment mechanisms (not shown) so that there is substantially no relative motion between the circuit board 3102 and the outer wall 306 of the sensor 310. In an embodiment, rigid and/or semi rigid cables may be used to communicably couple RF source and/or LO RF and/or clock signals attached to transceivers 308 in the system.

Referring again to FIG. 31 and FIG. 32, a customized analyzer may comprise the first circuit board 3102 and at least one additional circuit board 3104*a*, 3104*b*, 3104*c*, 3104*d* that may be communicably coupled using at least one RF cable to at least one antenna 3106. In an example, circuit boards 3102, 3104*a*, 3104*b*, 3104*c*, 3104*d* may be attached to the sensor using a variety of rigid and/or semi rigid attachment mechanisms (not shown) so that there is substantially no relative motion between the circuit boards 3102, 3104*a*, 3104*b*, 3104*c*, 3104*d* and the outer wall of the sensor. In an embodiment, rigid and/or semi rigid cables may be used to communicably couple RF source and/or LO RF and/or clock signals attached to transceivers 308 in the system.

In an example sensor, the sensing domain is an annular domain defined by a 12 in. diameter, 4 in. high outer wall 306 composed of acrylic and a 6 in. diameter, 4 in. high inner wall 312 also composed of acrylic. The acrylic cylinders that make up the outer wall 306 and inner wall 312 are glued in a concentric manner to an aluminum circular ring bottom plate 352*b* and top plate 352*a* with outer diameters of approximately 14 in. and inner diameters of approximately 6 in. The region between the outer wall 306 and inner wall 312 is filled with an emulsion comprising polysorbate, and canola oil and with a dielectric constant or relative permittivity of approximately 12.

Figure 33:
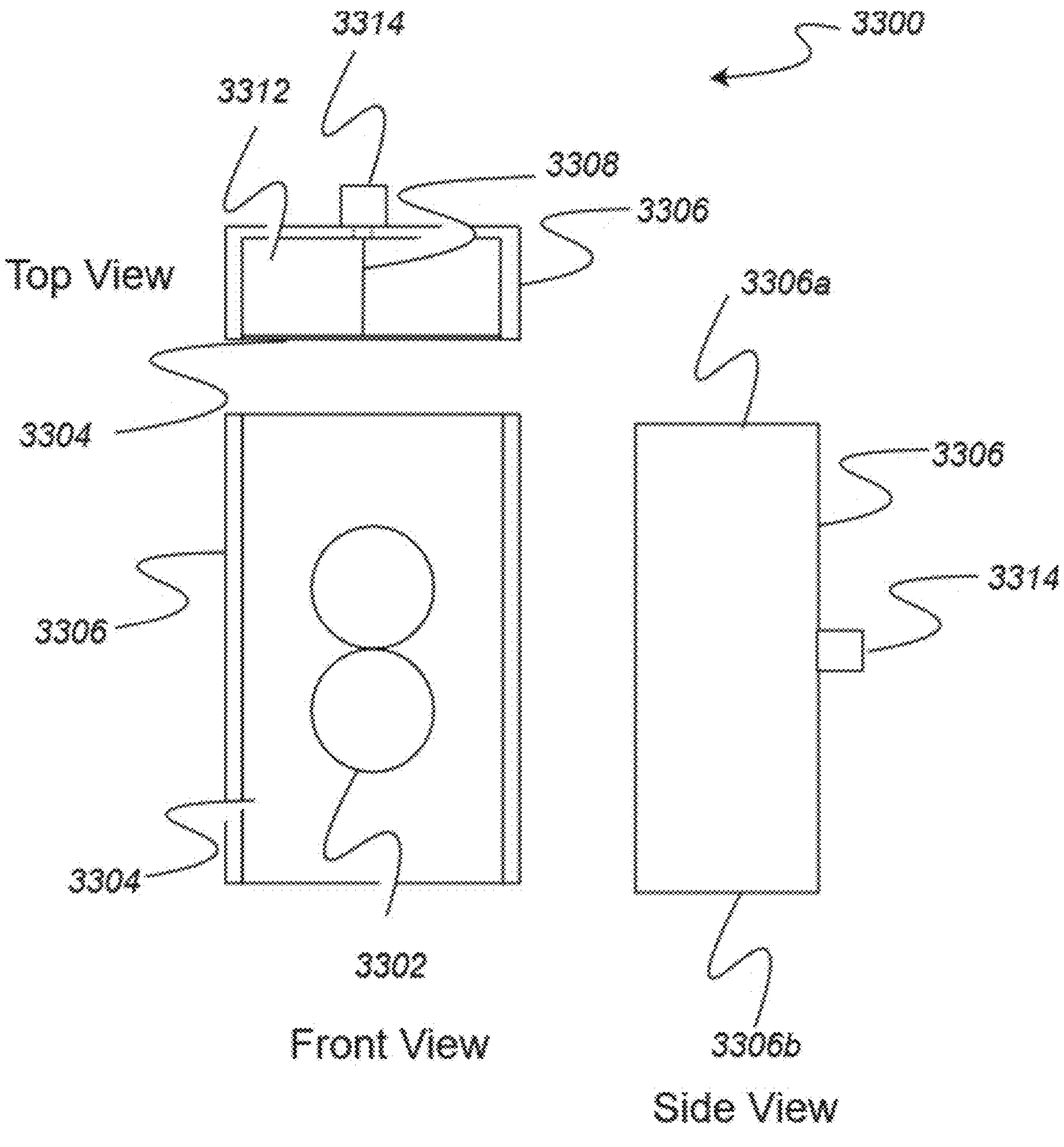
FIG. 33 shows a front, side, and top view of an example housing for a planar disk antenna of the present disclosure.

In this example, there are 16 planar disk antennas 308, 808, 3302 (see FIG. 35) distributed approximately evenly around and flush with the outside of the acrylic outer wall 306. The planar disk antennas may be mounted in a housing 3306 as shown in FIG. 33. The housing 3306 may comprise a conductor and/or a metal and/or may be made of aluminum. In an embodiment, the dimensions of the housing may be approximately 4 inches tall (top to bottom in FIG. 33), 2 inches wide (side to side in FIG. 33) and 1 in deep (front to back in FIG. 33). In an example, the height of the housing may be similar to the height, "h", of the annular sensing region. The metal housing may comprise two side walls and a back, and the front, top and bottom of the housing may not comprise a metal and may be described as being "open". The region within the housing 3312 may comprise air and/or may be filled with a material that substantially transmits electromagnetic radiation. In an example, the region within the housing 3312 may comprise RF absorbing and/or shielding materials.

A planar disk antenna 3302 may be formed on and/or attached to plastic and/or circuit board materials and/or on flexible materials with and without adhesive backing 3304. The material to which the planar disk antenna is attached may form a front wall of the housing 3306. In an example, a plastic insert may be formed to which the planar disk antenna 3302 may be attached and which may slide into the 3-sided metal housing 3306 so that the planar disk 3302 antenna is exposed and positioned to radiate signals away from the back wall of the housing 3306 and ultimately into the sensor domain (see FIG. 35). The metal housing 3306 may also comprise a microwave connector 3314 such as, but not limited to, an SMA connector. The center pin of the microwave connector 3314 may be electrically connected to the drive port of the planar disk antenna 3302 by a wire and/or a cable, and/or a trace and/or a conductor 3308. The microwave connector 3314 may be used to connect the antenna to transmitter circuitry, receiver circuitry, transceiver circuitry, portions of transceiver circuitry 3104 *a-d*, 3012, 3000, 2900, and the like as described throughout this disclosure.

Figure 34:
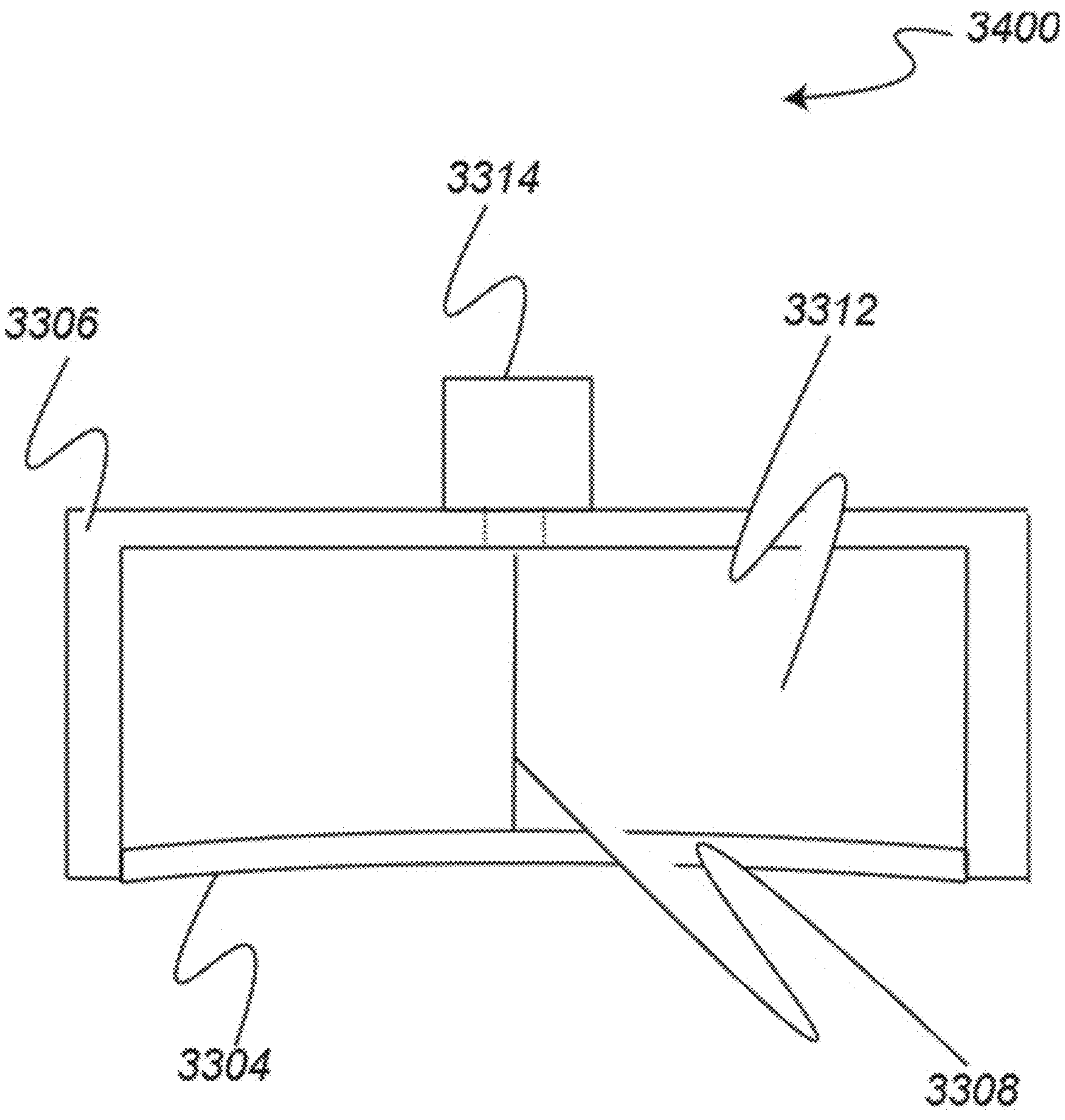
FIG. 34 shows a top view of another example housing for a planar disk antenna of the present disclosure.

FIG. 34 shows an example of a planar disk antenna 3302 mounted to a curved material (e.g., an adhesive backing 3304 that is curved). The curved material may allow the planar disk antenna to be mounted substantially flush against the curved outside wall 306 of the sensor domain. The top 3306*a* and/or bottom 3306*b* surfaces of the metal housing 3306 may include RF shielding and/or RF absorbing materials that may formed and/or attached and/or glued and/or adhered to their surface.

Figure 35:
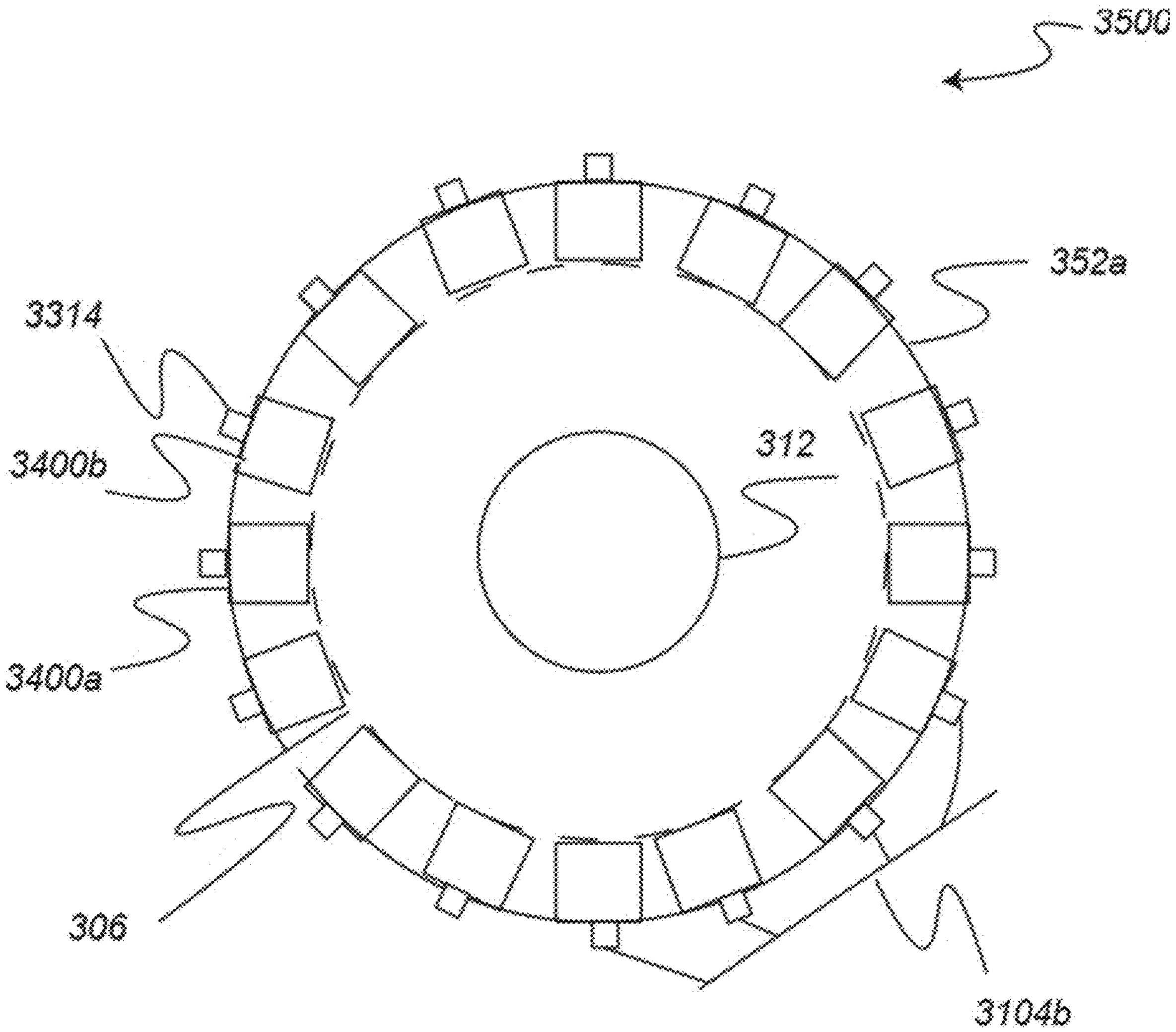
FIG. 35 shows a top view of a sensor of the present invention with sixteen antenna housings arrange to transmit and receive electromagnetic radiation to a sensor domain and/or an image domain.

FIG. 35 shows a top view of an example sensor 3500 with 16 antennas in their housings 3400*a*, 3400*b* (only two of the sixteen are labeled for clarity) arranged around the outside wall 306 of the sensor domain. In this example, a top plate 352*a* has a larger diameter that the outside wall 306 of the sensor. The 16 antennas and their housings 3400 are approximately equally distributed around the outer wall of the sensor 3500. The antennas and their housings may be held in place by a band and/or a strap and/or by an attachment mechanism and/or by glue and/or by being press fit in between the upper 352*a* and lower 352*b* plates. Four antenna housings may be attached to a circuit board 3104*b* as described previously and the system may comprise four circuit boards 3104*a-d* to that every antenna may be configured as a transmit and/or receive antenna. The circuit boards 3104*a-d* may be attached to the sensor domain so that RF cables are not moved when the sensor is translated and/or rotated.

In an example, a known scattering object may be a conducting cylinder with a diameter very close to 6 inches so that it may pass through but may be proximate to the inner wall 312 of the sensor. The conducting cylinder may comprise a rectangular hole that is approximately 1 in. by 2 in. and/or 2 in.×1 in. The conducting cylinder may have a length that is longer than the height of the sensor. The conducting cylinder may have a length of approximately 4 inches, 8 inches, 12 inches and the like. The cut outs may be closed to one end of the cylinder than the other. The cut outs may be closer to the center of the cylinder than to the ends. The cylinder may comprise aluminum.

In an example, the sensor may be calibrated by placing the conducting cylinder inside the inner wall 312 of the sensor. The sensor may transmit and receive RF signals at least one frequency and at least one relative orientation of the sensor and the conducting cylinder (specified by the position of the at least one cut-out in the cylinder for example). The sensor may transmit and receive RF signals at more than one frequency and/or at more than one relative orientation of the sensor and the cylinder. The sensor may rotate around the cylinder and may move up and down along the length of the cylinder. The cylinder may rotate within the sensor and may move up and down through the inner wall 312 of the sensor. Both the sensor and the cylinder may rotate and/or translate relative to each other. The rotations and translations may be in discrete steps and/or the movements may be continuous. Data collected while the conducting cylinder is within the inner wall 312 of the sensor 310 may be used to determine coefficients for the electromagnetic model of the sensor that may be used in future image reconstructions of other objects and/or OUTs in the sensor. Data collected while the conducting cylinder is within the inner wall of the sensor 310 may be used to determine error coefficients for a VNA and/or customized analyzer 206 of the sensor system.

Other examples and implementations are within the scope of the disclosure and the claims. For example, due to the nature of software and computers, functions described above can be implemented using software executed by a processor, hardware, firmware, hardwiring, or a combination of any of these. Features implementing functions may also be physically located at various positions, including being distributed such that portions of functions are implemented at different physical locations.

Also, as used herein, "or" as used in a list of items prefaced by "at least one of" or prefaced by "one or more of" indicates a disjunctive list such that, for example, a list of "at least one of A, B, or C," or a list of "one or more of A, B, or C," or "A, B, or C, or a combination thereof" means A or B or C or AB or AC or BC or ABC (i.e., A and B and C), or combinations with more than one feature (e.g., AA, AAB, ABBC, etc.).

As used herein, unless otherwise stated, a statement that a function or operation is "based on" an item or condition means that the function or operation is based on the stated item or condition and may be based on one or more items and/or conditions in addition to the stated item or condition.

Further, an indication that information is sent or transmitted, or a statement of sending or transmitting information, "to" an entity does not require completion of the communication. Such indications or statements include situations where the information is conveyed from a sending entity but does not reach an intended recipient of the information. The intended recipient, even if not actually receiving the information, may still be referred to as a receiving entity, e.g., a receiving execution environment. Further, an entity that is configured to send or transmit information "to" an intended recipient is not required to be configured to complete the delivery of the information to the intended recipient. For example, the entity may provide the information, with an indication of the intended recipient, to another entity that is capable of forwarding the information along with an indication of the intended recipient.

A wireless communication system is one in which at least some communications are conveyed wirelessly, e.g., by electromagnetic and/or acoustic waves propagating through atmospheric space rather than through a wire or other physical connection. A wireless communication network may not have all communications transmitted wirelessly but is configured to have at least some communications transmitted wirelessly. Further, the term "wireless communication device," or similar term, does not require that the functionality of the device is exclusively, or evenly primarily, for communication, or that the device be a mobile device, but indicates that the device includes wireless communication capability (one-way or two-way), e.g., includes at least one radio (each radio being part of a transmitter, receiver, or transceiver) for wireless communication.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, some operations may be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a storage medium. Processors may perform one or more of the described tasks.

Components, functional or otherwise, shown in the figures and/or discussed herein as being connected, coupled (e.g., communicatively coupled), or communicating with each other are operably coupled. That is, they may be directly or indirectly, wired and/or wirelessly, connected to enable signal transmission between them.

Having described several example configurations, various modifications, alternative constructions, and equivalents may be used without departing from the scope of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

"About" and/or "approximately" as used herein when referring to a measurable value such as an amount, a temporal duration, and the like, encompasses variations of ±20% or ±10%, ±5%, or +0.1% from the specified value, as appropriate in the context of the systems, devices, circuits, methods, and other implementations described herein. "Substantially" as used herein when referring to a measurable value such as an amount, a temporal duration, a physical attribute (such as frequency), and the like, also encompasses variations of 20% or +10%, ±5%, or +0.1% from the specified value, as appropriate in the context of the systems, devices, circuits, methods, and other implementations described herein.

A statement that a value exceeds (or is more than or above) a first threshold value is equivalent to a statement that the value meets or exceeds a second threshold value that is slightly greater than the first threshold value, e.g., the second threshold value being one value higher than the first threshold value in the resolution of a computing system. A statement that a value is less than (or is within or below) a first threshold value is equivalent to a statement that the value is less than or equal to a second threshold value that is slightly lower than the first threshold value, e.g., the second threshold value being one value lower than the first threshold value in the resolution of a computing system.

Further, more than one invention may be disclosed.

The invention claimed is:

1. A method for obtaining permittivity information of an object, comprising:

positioning the object in at least a portion of an electromagnetic field of a characterized sensor including at least one transmit antenna configured to transmit a radio frequency signal at one or more frequencies within the range of 10 MHz and 300 GHz, inclusive;

receiving, by one or more receive antennas one or more radio frequency signals produced in response to interaction of the radio frequency signal transmitted by the transmit antenna with the object; and determining permittivity information associated with the object based at least in part on phase and magnitude measurements of the one or more radio frequency signals received by the one or more receive antennas using a dual-gain reflectometer, wherein the dual-gain reflectometer is configured so that the received one or more radio frequency signals are selectively routable to measurement circuitry through either a first path having a first gain or a second path having a second gain, the second gain being different from the first gain.

2. The method of claim 1, wherein the characterized sensor is annular shaped sensor and positioning the object in at least the portion of the electromagnetic field includes positioning the object in a cylinder shaped volume formed by an inner wall of the annular shaped sensor.

3. The method of claim 2, wherein the annular shaped sensor further comprises a disk shaped conductive bottom surface.

4. The method of claim 2, wherein the annular shaped sensor further comprises a disk shaped conductive top surface including an opening disposed over the cylinder shaped volume.

5. The method of claim 4, wherein positioning the object in at least the portion of the electromagnetic field includes positioning the object in a removable object container configured to be disposed in the cylinder shaped volume.

6. The method of claim 1 further comprising computing one or more images based at least in part on the permittivity information.

7. A method for operating and calibrating a dielectric tomography system, comprising:

receiving one or more control signals to generate radio frequency signals and to configure one or more transceivers;

synthesizing and distributing the radio frequency signals, the radio frequency signals including radio frequency source signals, local oscillator signals, and clock signals;

configuring at least a portion of a transceiver to send or receive radio frequency signals;

determining phase and amplitude information for one or more received radio frequency signals; and applying correction information to the phase and the amplitude information, wherein the correction information is determined based at least in part on a comparison between measured radio frequency signals and expected radio frequency responses.

8. The method of claim 7 wherein the radio frequency source signals are configured as a carrier free waveform, a stepped frequency continuous wave (SFCW), a frequency modulated continuous wave (FMCW), a frequency modulated interrupted continuous wave (FMICW), a noise modulated continuous wave (NMCW), or combinations thereof.

9. The method of claim 7 wherein the radio frequency source signals include a set of simultaneous continuous wave tones distributed within a frequency band around a center frequency in a range of 10 MHz to 300 GHz.

10. The method of claim 7 wherein synthesizing and distributing the radio frequency signals includes filtering the radio frequency source signals.

11. The method of claim 7 wherein synthesizing and distributing the radio frequency signals includes controlling a power of the radio frequency source signals.

12. The method of claim 7 wherein synthesizing and distributing the radio frequency signals includes providing the radio frequency source signals and the local oscillator signals to a radio frequency sampler configured to determine amplitude and phase information for the radio frequency source signals.

13. The method of claim 12 wherein the radio frequency sampler is configured to output a digital indication of the amplitude and the phase information for the radio frequency source signals.

14. The method of claim 7 wherein the clock signals are in a range between 0.1 MHz and 100 MHz.

15. The method of claim 7 wherein the transceiver includes a dual-gain reflectometer configured to receive the radio frequency source signals through a switch and scattered radio frequency signals via an antenna.

16. The method of claim 7 wherein expected radio frequency responses comprise predicted radio frequency responses.

17. A transceiver in a dielectric tomography system, comprising:

at least one memory;

at least one oscillator;

a dual-gain reflectometer including an antenna;

a radio frequency measurement sampler;

at least one processor communicatively coupled to the at least one memory, the at least one oscillator, the dual-gain reflectometer, and the radio frequency measurement sampler, and configured to:

distribute radio frequency signals including radio frequency source signals, local oscillator signals, and clock signals;

determine phase and amplitude information for one or more received radio frequency signals; and apply correction information to the phase and the amplitude information.

18. The transceiver of claim 17 wherein the dual-gain reflectometer is configured to receive a radio frequency source signal via a switch and a scattered radio frequency signal via the antenna, and output a signal to the radio frequency measurement sampler.

19. The transceiver of claim 17 wherein the radio frequency measurement sampler comprises a mixer configured to receive a local oscillator signal and an output from the dual-gain reflectometer.

20. The transceiver of claim 19 wherein the radio frequency measurement sampler further comprises at least one attenuator and at least one amplifier configured to attenuate and amplify the local oscillator signal prior to the mixer.

21. The transceiver of claim 19 wherein the radio frequency measurement sampler further comprises at least one balun to enable a differential signal in the mixer.

22. A dielectric tomography system comprising:

a radio frequency signal source configured to provide a radio frequency source signal at one or more frequencies within the range of 10 MHz and 300 GHz, inclusive;

one or more antennas coupled to the radio frequency signal source and configured to transmit outgoing radio frequency signals based at least in part on the radio frequency source signal, and to receive incoming radio frequency signals responsive to interaction of the outgoing radio frequency signals with an object disposed in an electromagnetic field generated by the one or more antennas;

a dual-gain reflectometer coupled to the one or more antennas, the dual-gain reflectometer including a first signal path and a second signal path, the first signal path having a first gain and the second signal path having a second gain different from the first gain, wherein an incoming radio frequency signal is selectively routable through either the first signal path or the second signal path; and measurement circuitry configured to determine phase and amplitude information for the incoming radio frequency signal based at least in part on a signal output from the dual-gain reflectometer, the phase and amplitude information usable to determine permittivity information associated with the object.

23. The system of claim 22, wherein the radio frequency signal source comprises an input configured to receive the radio frequency source signal from an external source.

24. The system of claim 22, wherein the incoming radio frequency signals comprise radio frequency signals scattered by the object.

25. The system of claim 22, wherein the one or more antennas are disposed in an annular compartment comprising an outer wall, an inner wall disposed within the outer wall, and a coupling medium disposed between the outer wall and the inner wall, the inner wall defining a volume configured to receive the object.

26. The system of claim 22, wherein the measurement circuitry comprises a radio frequency measurement sampler including a mixer configured to receive a local oscillator signal and the signal output from the dual-gain reflectometer.

27. The system of claim 22, further comprising at least one processor and at least one memory communicatively coupled to the measurement circuitry, the at least one processor configured to determine the permittivity information associated with the object based at least in part on the phase and amplitude information.

28. The system of claim 22, further comprising an output configured to forward the phase and amplitude information to external circuitry configured to determine the permittivity information associated with the object.

29. The system of claim 22, further comprising a transceiver including the one or more antennas, the dual gain reflectometer, and the measurement circuitry.

* * * * *